US008575188B2

(12) United States Patent
Cai et al.

(10) Patent No.: US 8,575,188 B2
(45) Date of Patent: Nov. 5, 2013

(54) CAMPTOTHECIN DERIVATIVES

(75) Inventors: Xiaohong Cai, Redwood City, CA (US); Jian-Xin Duan, Redwood City, CA (US); Mark Matteucci, Redwood City, CA (US); Yeyu Cao, Redwood City, CA (US); Hailong Jiao, Redwood City, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/378,662

(22) PCT Filed: Jun. 16, 2010

(86) PCT No.: PCT/US2010/038890
§ 371 (c)(1),
(2), (4) Date: Mar. 2, 2012

(87) PCT Pub. No.: WO2010/148138
PCT Pub. Date: Dec. 23, 2010

(65) Prior Publication Data
US 2012/0165522 A1    Jun. 28, 2012

Related U.S. Application Data

(60) Provisional application No. 61/218,043, filed on Jun. 17, 2009, provisional application No. 61/325,223, filed on Apr. 16, 2010.

(51) Int. Cl.
*A61K 31/4745* (2006.01)
*C07D 491/22* (2006.01)
(52) U.S. Cl.
USPC ............... 514/283; 546/48; 546/14; 544/125; 514/233.2
(58) Field of Classification Search
USPC ............. 514/283, 233.2; 546/48, 14; 544/125
See application file for complete search history.

(56) References Cited

U.S. PATENT DOCUMENTS

| 5,459,269 A | 10/1995 | Comins |
| 6,403,604 B1 | 6/2002 | Yang et al. |
| 2007/0093432 A1 | 4/2007 | Yang |

FOREIGN PATENT DOCUMENTS

WO    WO-94/11376 A1    5/1994

OTHER PUBLICATIONS

Extended European Search Report for Application No. 10790151.4 dated Nov. 8, 2012.
Cao, "Preparation of 14-nitrocamptothecin derivatives by reactions of camptothecin with nitronium tetrafluoroborate in acidic solvents," J. Chem. Soc., Perkin Trans. 1, 21: 2629-2632 (1996).
Cheng et al., "14-azacamptothecin: a potent water-soluble topoisomerase I poison," J. Am. Chem. Soc. 127(3) 838-839 (2005).
Database Registry [Online], Database accession No. 1026010-90-1 (2008).
Ferrer et al., "Studies on the reductively triggered release of heterocyclic and steroid drugs from 5-nitrothien-2-ylmethyl prodrugs," Tetrahedron 59(19):3437-3444 (2003).
Sawada et al., "Synthesis and antitumor activity of 20(S)-camptothecin derivatives: A-ring modified and 7,10-disubstituted camptothecins," Chemical & Pharmaceutical Bulletin 39(12):3183-3188 (1991).
Vadwai et al., "Insilico analysis of homocamptothecin (hCPT) analogues for anti-tumour activity", International Journal of Bioinformatics Research and Applications 5(6):603-615 (2009).
Verma et al., "Camptothecins: a SAR/QSAR study," Chemical Reviews 109(1) 213-235 (2009).
International Search Report and Written Opinion for PCT/US2010/038890, dated Mar. 28, 2011, 10 pages.

*Primary Examiner* — Charanjit Aulakh
(74) *Attorney, Agent, or Firm* — Foley & Lardner LLP; Antoinette F. Konski; Photon Rao

(57) ABSTRACT

Various 14-nitro, 14-amino, and 14-substituted amino camptothecin derivatives are useful in the treatment of cancer and other hyperproliferative diseases. 14-Nitro camptothecin derivatives are conveniently prepared by reacting a camptothecin derivative with fuming nitric acid, optionally employing acetic anhydride as a solvent.

17 Claims, No Drawings

CAMPTOTHECIN DERIVATIVES

CROSS-REFERENCE TO RELATED PATENT APPLICATIONS

This application is a national stage entry under 37 U.S.C. §371 of International Patent Application No. PCT/US2010/038890, filed Jun. 16, 2010, which in turn claims priority under 37 U.S.C. §119(e) to U.S. Patent Application No. 61/218,043, filed Jun. 17, 2009, and U.S. Patent Application No. 61/325,223, filed Apr. 16, 2010, each of which are incorporated herein by reference in their entireties.

FIELD OF THE INVENTION

The present invention provides compounds useful in the treatment of cancer and other hyperproliferative diseases, and so relates to the fields of chemistry, biology, medicinal chemistry, pharmacology, and medicine.

BACKGROUND OF THE INVENTION

Camptothecin is a cytotoxin that inhibits topoisomerase I, an enzyme essential for DNA synthesis, and was first isolated from the leaves of the *Camptotheca acuminata* tree. Camptothecin showed anti-cancer activity in clinical trials but was poorly soluble and generated adverse drug reactions. Topotecan (Hycamtin, GlaxoSmithKline) and irinotecan (Campto, Yakult Honsha, and Camptosar, Pfizer) are semisynthetic derivatives of camptothecin, with the former approved by the U.S. FDA for the treatment of ovarian, cervical, and small cell lung cancer, and the latter approved for the treatment of colon cancer. Irinotecan is activated by hydrolysis to SN-38. The structures of these compounds are shown below along with the numbering used herein for the camptothecin ring.

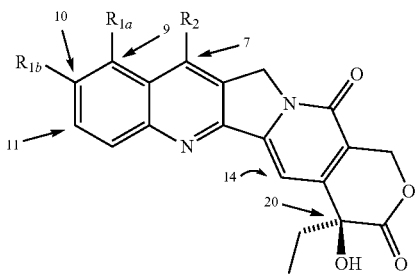

Camptothecin: $R_{1a}=R_{1b}=R_2=H$;
Topotecan: $R_{1a}=$—$CH_2NMe_2$, $R_{1b}=OH$, and $R_2=H$;
Irinotecan: $R_{1a}=H$, $R_{1b}=$

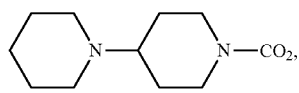

and $R_2=Et$; and
SN-38: $R_{1a}=H$, $R_{1b}=OH$, $R_2=Et$.

The camptothecin derivatives approved for anti-cancer use are susceptible to one or more of the several mechanisms by which cancer cells can become resistant to chemotherapy. There remains a need for new camptothecin derivatives, particularly derivatives that are more potent anti-cancer agents, can be used to treat cancers resistant to treatment with the approved derivatives, and/or exhibit fewer or less severe adverse side effects. The present invention meets this need.

SUMMARY OF THE INVENTION

In one aspect, the present invention provides compounds of Formula I:

Formula I

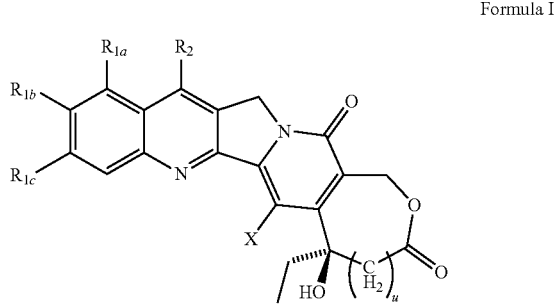

wherein u is 0 or 1;

$R_{1a}$, $R_{1b}$, and $R_{1c}$ each independently are H, halogen, hydroxyl, nitrile, amino, substituted amino, nitro, carboxyl ester, aminocarbonyl, substituted sulfonyl, aminosulfonyl, substituted or unsubstituted $C_1$-$C_6$ alkyl, substituted or unsubstituted $C_2$-$C_6$ alkynyl, substituted or unsubstituted $C_2$-$C_6$ alkenyl, substituted or unsubstituted aryl, substituted or unsubstituted heteroaryl, substituted or unsubstituted cycloalkyl, substituted or unsubstituted heterocycloalkyl, or a substituted or unsubstituted $C_1$-$C_6$alkoxy group, or $R_{1a}$ and $R_{1b}$ together with the carbon atoms to which they are bonded form a 5-7 membered heterocycle, or $R_{1b}$ and $R_{1c}$ together with the carbon atoms to which they are bonded form a 5-7 membered heterocycle;

$R_2$ is H, halogen, nitrile, formyl, oxime, hydrazone, imine, substituted or unsubstituted $C_1$-$C_6$ alkyl, substituted or unsubstituted aryl, substituted or unsubstituted heteroaryl, substituted or unsubstituted heterocyclyl, substituted or unsubstituted $C_2$-$C_6$ alkenyl, or substituted or unsubstituted $C_2$-$C_6$ alkynyl group; or $R_2$ and $R_{1a}$ together with the carbon atoms to which they are attached form a 5-7 membered substituted cycloalkyl ring;

X is nitro or —$NR_3R_4$;

$R_3$ and $R_4$ each independently are H, $C_1$-$C_6$ alkyl, —$CO_2R_5$, or —$COR_6$;

$R_5$ is substituted or unsubstituted $C_1$-$C_6$ alkyl, substituted or unsubstituted aryl, or substituted or unsubstituted heteroaryl;

$R_6$ is H, substituted or unsubstituted $C_1$-$C_6$ alkyl, substituted or unsubstituted aryl, or substituted or unsubstituted heteroaryl;

or an ester or salt, including a pharmaceutically acceptable salt, thereof, provided however that the compound excludes 14-nitro-20-acetoxycamptothecin.

In another aspect, the present invention provides compounds prepared by the process comprising, consisting essentially, or consisting of contacting a compound of Formula IX or a salt or ester thereof:

Formula IX

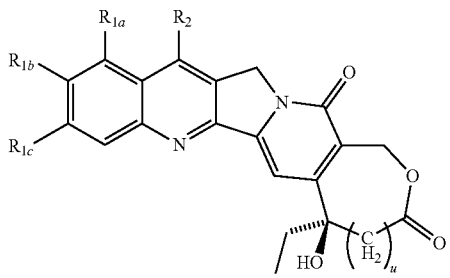

wherein u, $R_{1a}$, $R_{1b}$, $R_2$ are as defined in Formula I above, with fuming nitric acid, provided however that the compound prepared excludes 14-nitro-20-acetoxycamptothecin.

In another aspect, the present invention provides methods for synthesizing the compounds of the present invention comprising, consisting essentially, or consisting of contacting a compound of Formula IX as shown above, or a salt or ester thereof, wherein u $R_{1a}$, $R_{1b}$, $R_2$ are as defined in Formula I above, with fuming nitric acid to provide a compound of Formula IXA:

Formula IXA

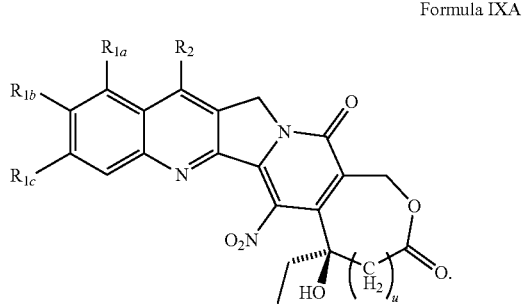

In one embodiment of this method, the compound synthesized is a compound of Formula IXA in which u is 0. In another embodiment, the contacting with nitric acid is performed in acetic anhydride.

In another aspect, the present invention provides pharmaceutical compositions comprising, consisting essentially, or consisting of a compound of the present invention or 14-nitro-20-acetoxycamptothecin or a salt of either, and a pharmaceutically acceptable carrier, excipient, or diluent.

In another aspect, the present invention provides a method of inhibiting growth of a cancer cell or another hyperproliferative cell comprising, consisting essentially, or consisting of contacting the cancer cell with an effective amount of a compound of the present invention, 14-nitro-20-acetoxycamptothecin, or a salt of either, or with a pharmaceutical composition of the present invention.

In another aspect, the present invention provides a method of treating cancer or another hyperproliferative disease comprising, consisting essentially, or consisting of administering a therapeutically effective amount of a compound of the present invention, 14-nitro-20-acetoxycamptothecin, or a salt of either, or administering a pharmaceutical composition of the present invention to a patient in need of such treatment, thereby treating the cancer or other hyperproliferative disease.

In another aspect, the present invention provides a use of a compound of the present invention, 14-nitro-20-acetoxycamptothecin, or a salt of either for the manufacture of a medicament for the treatment of cancer or another hyperproliferative disease.

DETAILED DESCRIPTION OF THE INVENTION

Definitions

It is to be understood that the terminology used herein is for the purpose of describing particular embodiments and/or aspects only and is not intended to limit the scope of this invention. In this specification and in the claims that follow, reference will be made to a number of terms that shall be defined to have the meanings below.

All numerical designations, e.g., pH, temperature, time, concentration, and weight, including ranges, are approximations that typically may be varied (+) or (−) by increments of 0.1, 1.0, or 10.0, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an", and "the" includes plural references unless the context clearly dictates otherwise.

As used herein, the term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

"$C_x$-$C_y$" (or "$C_{x\text{-}y}$") before a group refers to a range of the number of carbon atoms that are present in that group. For example, $C_1$-$C_6$ alkyl refers to an alkyl group having at least 1 and up to 6 carbon atoms.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Alkyl" refers to monovalent saturated aliphatic hydrocarbyl groups having from 1 to 10 carbon atoms and, in some embodiments, from 1 to 6 carbon atoms. "$C_{x\text{-}y}$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" refers to an alkyl group having at least 1 and, in some embodiments, 2, 3, or more non-alkyl substituents, which may be selected from, without limitation, the group consisting of vinyl and other alkenyl, substituted alkenyl, ethynyl and other alkynyl, substituted alkynyl, alkoxy, substituted alkoxy, acyl, acylamino, acyloxy, amino, substituted amino, —CONH$_2$ and other aminocarbonyl, aminothiocarbonyl, aminocarbonylamino, aminothiocarbonylamino, aminocarbonyloxy, —SO$_2$NH$_2$ and other aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, oxirane

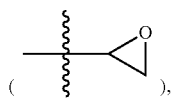

nitro, -nitrate (—ONO$_2$), spirocycloalkyl, SO$_3$H, substituted sulfonyl, sulfonyloxy, thioacyl, thiocyanate, thiol, trimethylsilyl and other trialkylsilyl, dimethylhydroxysilyl, alkylthio, and substituted alkylthio. Substituted alkyl includes geminally substituted alkyl such as a substituted or unsubstituted —CH(O-alkyl)$_2$ or —CH(O-aryl)$_2$ moiety, and wherein the two O-alkyl groups, together, can form a ring structure.

"Alkylidene" or "alkylene" refers to divalent saturated aliphatic hydrocarbyl groups having from 1 to 10 carbon atoms and, in some embodiments, from 1 to 6 carbon atoms. "$C_{u-v}$alkylene" refers to alkylene groups having from u to v carbon atoms. The alkylidene and alkylene groups include branched and straight chain hydrocarbyl groups. For example, "$C_{1-6}$ alkylene" includes methylene, ethylene, propylene, 2-methypropylene, pentylene, and the like.

"Substituted alkylidene" or "substituted alkylene" refers to an alkylidene or alkylene group having at least 1 and, in some embodiments, 2, 3, or more substituents, which may be selected from, without limitation the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, SO$_3$H, substituted sulfonyl, sulfonyloxy, thioacyl, thiocyanate, thiol, alkylthio, and substituted alkylthio.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $C_{x-y}$ alkenyl refers to alkenyl groups having from x to y carbon atoms and is meant to include, for example, ethenyl, propenyl, 1,3-butadienyl, and the like.

"Substituted alkenyl" refers to alkenyl groups having at least 1 and, in some embodiments, 2, 3, or more substituents, which may be selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, with the proviso that any hydroxy or thiol substitution is not attached to a vinyl (unsaturated) carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $C_{2-6}$ alkynyl includes ethynyl, propynyl, and the like.

"Substituted alkynyl" refers to alkynyl groups having at least 1 and, in some embodiments, 2, 3, or more substituents, which may be selected from, without limitation, the group consisting of alkoxy, substituted alkoxy, acyl, acylamino, acyloxy, alkyl, substituted alkyl, alkenyl, substituted alkenyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, with the proviso that any hydroxy or thiol substitution is not attached to an acetylenic carbon atom.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl).

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—. Acyl includes the "acetyl" group CH$_3$C(O)—.

"Acylamino" refers to the groups —NR$^{20}$C(O)alkyl, —NR$^{20}$C(O)substituted alkyl, —NR$^{20}$C(O)cycloalkyl, —NR$^{20}$C(O)substituted cycloalkyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic wherein R$^{20}$ is hydrogen or alkyl.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Amino" refers to the group —NH$_2$.

"Substituted amino" refers to the group —NR$^{21}$R$^{22}$ where R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{21}$ and R$^{22}$ are optionally joined together with the nitrogen bound thereto to form a heterocyclic or substituted heterocyclic group, provided that R$^{21}$ and R$^{22}$ are both not hydrogen. When R$^{21}$ is hydrogen and R$^{22}$ is alkyl, the substituted amino group is sometimes referred to herein as alkylamino. When R$^{21}$ and R$^{22}$ are alkyl, the substituted amino group is sometimes referred to herein as dialkylamino. When referring to a monosubstituted amino, either R$^{21}$ or R$^{22}$ is hydrogen, but both are not hydrogen. When referring to a disubstituted amino, neither R$^{21}$ nor R$^{22}$ are hydrogen.

"Hydroxyamino" refers to the group —NHOH.

"Alkoxyamino" refers to the group —NHO-alkyl.

"Aminocarbonyl" refers to the group —C(O)NR$^{23}$R$^{24}$, wherein R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, substituted alkoxy, amino, substituted amino, and acylamino, and where R$^{23}$ and R$^{24}$ are optionally joined together with the nitrogen bound thereto to form a heterocyclic or substituted heterocyclic group.

"Aminocarbonylamino" refers to the group —NR$^{20}$C(O)NR$^{23}$R$^{24}$, wherein R$^{20}$ is hydrogen or alkyl, and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminothiocarbonylamino" refers to the group —NR$^{20}$C(S)NR$^{23}$R$^{24}$, wherein R$^{20}$ is hydrogen or alkyl, and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminocarbonyloxy" refers to the group —O—C(O)NR$^{23}$R$^{24}$, wherein R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminosulfonyl" refers to the group —SO$_2$NR$^{23}$R$^{24}$, wherein R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminosulfonyloxy" refers to the group —O—SO$_2$NR$^{23}$R$^{24}$, wherein R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminosulfonylamino" refers to the group —NR$^{20}$—SO$_2$NR$^{23}$R$^{24}$, wherein R$^{20}$ is hydrogen or alkyl, and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aminothiocarbonyl" refers to the group —C(S)NR$^{23}$R$^{24}$, wherein R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Amidino" refers to the group —C(=NR$^{25}$)NR$^{23}$R$^{24}$, wherein R$^{23}$, R$^{24}$, and R$^{25}$ each independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and wherein R$^{23}$ and R$^{24}$ are optionally joined together with the nitrogen bound thereto to form a heterocyclic or substituted heterocyclic group.

"Aryl" or "Ar" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8tetrahydronaphthalene-2-yl is an aryl group as its point of attachment is at the 2-position of the aromatic phenyl ring).

"Substituted aryl" refers to aryl groups which are substituted with at least 1 and, in some embodiments, 2, 3, or more substituents, which may be selected from, without limitation, the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio.

"Aryloxy" refers to the group —O-aryl, and includes, by way of example, phenoxy and naphthyloxy.

"Substituted aryloxy" refers to the group —O-(substituted aryl).

"Arylthio" refers to the group —S-aryl.

"Substituted arylthio" refers to the group —S-(substituted aryl).

"Azido" refers to the group —$N_3$.

"Cancer" refers to solid tumors and leukemias, lymphomas, and malignant tumors of potentially unlimited growth that can expand locally by invasion and systemically by metastasis. Examples of cancers include, but are not limited to cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Cyano" or "nitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic.

"(Carboxyl ester)amino" refers to the group —$NR^{20}$—C(O)O-alkyl, —$NR^{20}$—C(O)O-substituted alkyl, —$NR^{20}$—C(O)O-alkenyl, —$NR^{20}$—C(O)O-substituted alkenyl, —$NR^{20}$—C(O)O-alkynyl, —$NR^{20}$—C(O)O-substituted alkynyl, —$NR^{20}$—C(O)O-aryl, —$NR^{20}$—C(O)O-substituted aryl, —$NR^{20}$—C(O)O-cycloalkyl, —$NR^{20}$—C(O)O-substituted cycloalkyl, —$NR^{20}$—C(O)O-heteroaryl, —$NR^{20}$—C(O)O-substituted heteroaryl, —$NR^{20}$—C(O)O-heterocyclic, and —$NR^{20}$—C(O)O-substituted heterocyclic, wherein $R^{20}$ is alkyl or hydrogen.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic.

"Compound" and "compounds" as used herein refer to a compound encompassed by the generic formulae disclosed herein, any subgenus of those generic formulae, and any forms of the compounds within the generic and subgeneric formulae, including the racemates, stereoisomers, and tautomers of the compound or compounds. Compound and compounds of the invention include the 14-nitro, 14-amino, or 14-substituted amino camptothecin derivatives disclosed herein and their salts, including pharmaceutically acceptable salts, and esters provided however that the compounds of the invention do not include 14-nitro-20-acetoxy camptothecin.

"Combination treatment" and grammatical equivalents thereof as used herein refer to coadministration of a compound of the present invention or a pharmaceutical formulation of 14-nitro-20-acetoxy camptothecin of the invention with one or more of another agent, radiation therapy, and/or surgery. Coadministration of two or more therapeutic agents can be practiced prior to, contemporaneously with, or after radiation therapy or surgery.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"Cycloalkenyl" refers to a partially saturated cycloalkyl ring having at least one site of >C=C< ring unsaturation.

"Substituted cycloalkyl" refers to a cycloalkyl group, as defined herein, having at least one and, in some embodiments, 2, 3, or more substituents, which may be selected from, without limitation, the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Fuming nitric acid" refers to concentrated aqueous nitric acid containing at least about 85% nitric acid.

"Guanidino" or guanidine refers to the group —NHC(=NH)NH$_2$.

"Substituted guanidino" refers to —NR$^{29}$C(=NR$^{29}$)N(R$^{29}$)$_2$, wherein each R$^{29}$ is independently selected from the group consisting of hydrogen, alkyl, substituted alkyl, aryl, substituted aryl, heteroaryl, substituted heteroaryl, heterocyclyl, and substituted heterocyclyl and two R$^{29}$ groups attached to a common guanidino nitrogen atom may optionally be joined together with the nitrogen bound thereto to form a heterocyclic or substituted heterocyclic group, provided that at least one R$^{29}$ is not hydrogen.

"Halo" or "halogen" refers to fluoro, chloro, bromo, and iodo.

"Haloalkyl" refers to substitution of alkyl groups with at least one and, in some embodiments, 2, 3, or more halo groups.

"Haloalkoxy" refers to substitution of alkoxy groups with at least one and, in some embodiments, 2, 3, or more halo groups.

"Hydroxy" or "hydroxyl" refers to the group —OH.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl-2-yl and imidazol5-yl) and multiple ring systems (e.g. imidazopyridyl, benzotriazolyl, benzimidazol-2-yl and benzimidazol-6-yl). For multiple ring systems, including fused, bridged, and spiro ring systems having aromatic and non-aromatic rings, the term "heteroaryl" applies if there is at least one ring heteroatom, and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. The term heteroaryl includes, but is not limited to, acridinyl, azocinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzothienyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazopyridyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isoquinolyl, isothiazolyl, isoxazolyl, naphthyridinyl, octahydroisoquinolinyl, oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl.

"Substituted heteroaryl" refers to heteroaryl groups that are substituted with at least 1 and, in some embodiments, 2, 3, or more substituents. Illustrative substituents include those provided in the definition of substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom, and the point of attachment is at an atom of a non-aromatic ring (e.g. 1,2,3,4-tetrahydroquinolin-3-yl, 5,6,7,8-tetrahydroquinoline-6-yl, and decahydroquinolin-6-yl). In some embodiment, the heterocyclic groups herein are 3-15 membered, 4-14 membered, 5-13 membered, 7-12, or 5-7 membered heterocycles. In some other embodiment, the heterocycles contain 4 heteroatoms. In some other embodiment, the heterocycles contain 3 heteroatoms. In another embodiment, the heterocycles contain up to 2 heteroatoms. In some embodiments, the nitrogen and/or sulfur atom(s) of the heterocyclic group are optionally oxidized to provide for the N-oxide, sulfinyl, sulfonyl moieties. Heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_{3-10}$) refers to the total number of carbon atoms in the portion of the heterocyclyl group exclusive of the number of heteroatoms.

"Substituted heterocyclic" or "substituted heterocycle" or "substituted heterocycloalkyl" or "substituted heterocyclyl" refers to heterocyclic groups, as defined herein, that are substituted with at least one and, in some embodiments, 2, 3, or more substituents. Illustrative substituents include those provided in the definition of substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

"Hydrazino" refers to the group —NHNH$_2$.

"Substituted hydrazino" refers to the group —NR$^{26}$NR$^{27}$R$^{28}$, wherein R$^{26}$, R$^{27}$, and R$^{28}$ are each independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, or wherein R$^{27}$ and R$^{28}$ are optionally joined, together with the nitrogen bound thereto to form a heterocyclic or substituted heterocyclic group, provided that $R^{27}$ and $R^{28}$ are both not hydrogen.

"Hydrazone" refers to —C=N-amino or —C=N-substituted amino.

"Hyperproliferative disease" refers to a disease characterized by cellular hyperproliferation (e.g., an abnormally increased rate or amount of cellular proliferation). Cancer is a hyperproliferative disease. Examples of hyperproliferative diseases other than cancer include, but are not limited to, allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

"Imine" refers to —C=N—$R^{30}$, wherein $R^{30}$ is alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, or substituted heterocyclyl.

"Leaving group" refers to a moiety that can be replaced by a nucleophile. Examples of leaving groups include but are not limited to halo and sulfonate.

"Nitro" refers to the group —$NO_2$.

"Oxo" refers to the atom (=O).

"Oxide" refers to products resulting from the oxidation of one or more heteroatoms. Examples include N-oxides, sulfoxides, and sulfones.

"Oxime" refers to —C=N—O—$R^{31}$, wherein $R^{31}$ is alkyl, substituted alky, alkenyl, substituted alkenyl, alkynyl, substituted alkynyl, aryl, substituted aryl, heteroaryl, substituted heteroaryl, cycloalkyl, substituted cycloalkyl, heterocyclyl, or substituted heterocyclyl.

"Patient" refers to mammals, including humans and veterinary animals, such as cattle, horses, dogs, and cats, suffering from cancer or another hyperproliferative disease.

"Pharmaceutically acceptable carrier, excipient, or diluent" refers to a carrier, excipient, or diluent that is useful in preparing a pharmaceutical composition that is generally safe, non-toxic and neither biologically nor otherwise undesirable, and includes a carrier, excipient, or diluent that is acceptable for veterinary use as well as human pharmaceutical use. A "pharmaceutically acceptable carrier, excipient, or diluent" may include only one or more than one such carrier, excipient, and/or diluent.

"Pharmaceutically acceptable salt" refers to pharmaceutically acceptable salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

QnD or qnd refers to drug administration once every n days. For example, QD (or qd) refers to once every day or once daily dosing, Q2D (or q2d) refers to a dosing once every two days, Q7D refers to a dosing once every 7 days or once a week, Q5D refers to dosing once every 5 days.

"Reduction" of a symptom or symptoms (and grammatical equivalents of this phrase) refers to decreasing the severity or frequency of the symptom(s), or elimination of the symptom(s).

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown here attached to bonds marked with wavy lines is substituted with a spirocycloalkyl group:

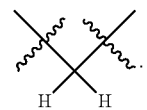 [SMILES: *C*]

"Sulfonyl" refers to the divalent group —$S(O)_2$—.

"Substituted sulfonyl" refers to the group —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-cycloalkyl, —$SO_2$-substituted cylcoalkyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic. Substituted sulfonyl includes, for example and without limitation, groups such as methyl-$SO_2$—, phenyl-$SO_2$—, and 4-methylphenyl-$SO_2$—.

"Sulfonyloxy" or "sulfonate" refers to the groups —$OSO_2$-alkyl, —$OSO_2$-substituted alkyl, —$OSO_2$-alkenyl, —$OSO_2$-substituted alkenyl, —$OSO_2$-cycloalkyl, —$OSO_2$-substituted cylcoalkyl, —$OSO_2$-aryl, —$OSO_2$-substituted aryl, —$OSO_2$-heteroaryl, —$OSO_2$-substituted heteroaryl, —$OSO_2$-heterocyclic, and —$OSO_2$-substituted heterocyclic.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S).

"Thiol" refers to the group —SH.

"Alkylthio" refers to the group —S-alkyl.

"Substituted alkylthio" refers to the group —S-(substituted alkyl).

"Thiocarbonyl" refers to the divalent group —C(S)— which is equivalent to —C(=S)—.

"Thione" refers to the doubly bonded atom (=S).

"Thiocyanate" refers to the group —SCN.

"Therapeutically effective amount" of a drug refers to an amount of a drug that, when administered to a patient with cancer or another hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or another hyperproliferative disease; diminishment of extent of disease; delay or slowing of disease progression; amelioration, palliation, or stabilization of the disease state; or other beneficial results.

The following disclosure is organized into sections only for the convenience of the reader, and disclosure found in any section is applicable to disclosure elsewhere in the specification.

Compounds of the Invention

In one aspect, the present invention provides compounds of Formula I or a salt thereof:

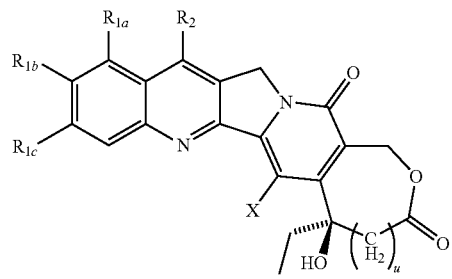

Formula I wherein u, $R_{1a}$, $R_{1b}$, $R_{1c}$, $R_2$, X, $R_3$, $R_4$, $R_5$, and $R_6$ are as defined in Formula I in the Summary of the Invention above.

In one embodiment, the salt is a pharmaceutically acceptable salt of a compound of Formula I. In another embodiment, the present invention provides esters of the compounds of Formula I other than 14-nitro-20-acetoxycamptothecin.

In one embodiment, the compound of the invention is a compound of Formula IA, IB, IC, ID, IE, or IF:

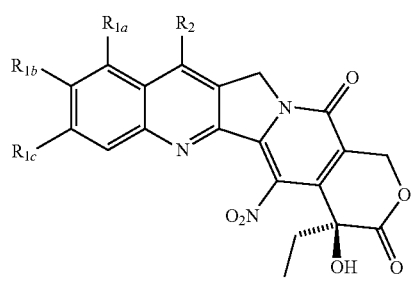

Formula IA

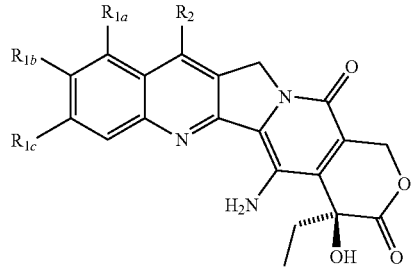

Formula IB

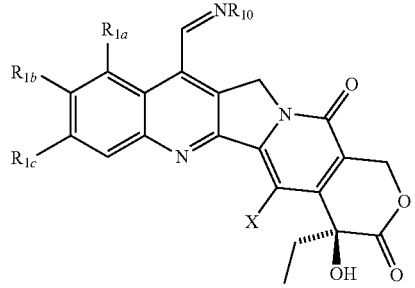

Formula IC

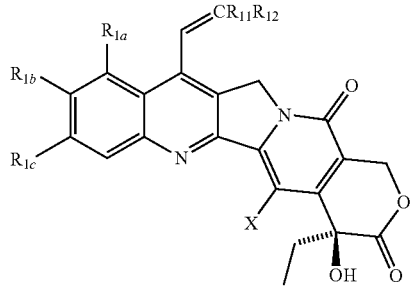

Formula ID

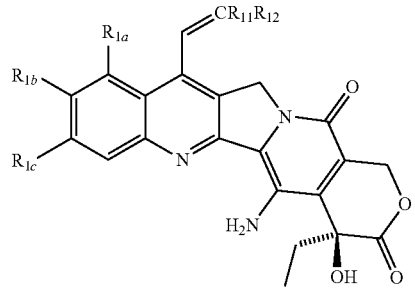

Formula IE

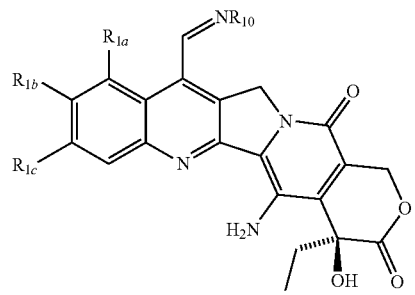

Formula IF wherein
$R_{1a}$, $R_{1b}$, $R_{1c}$, $R_2$, and X are as defined in Formula I above;
$R_{10}$ is —$OR_{13}$, $NR_{14}R_{15}$, or a substituted or unsubstituted aryl or heteroaryl group;
$R_{11}$ is H or $C_1$-$C_3$ alkyl;
$R_{12}$ is H, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, substituted or unsubstituted heteroaryl group, or —COR$_{16}$;

R$_{13}$ is H, or substituted or unsubstituted C$_1$-C$_6$ alkyl, substituted or unsubstituted C$_1$-C$_6$ alkenyl, substituted or unsubstituted C$_3$-C$_8$ cycloalkyl, substituted or unsubstituted heterocyclyl, substituted or unsubstituted aryl, or substituted or unsubstituted heteroaryl group;

R$_{14}$ and R$_{15}$ independently are H, SO$_2$R$_{17}$, —COR$_{18}$, substituted or unsubstituted C$_1$-C$_6$ alkyl, substituted or unsubstituted C$_3$-C$_8$ cycloalkyl, substituted or unsubstituted heterocyclyl, substituted or unsubstituted aryl, substituted or unsubstituted heteroaryl group, or —COR$_{16}$, or R$_{14}$ and R$_{15}$ together with the nitrogen atom to which they are bonded form a 5-7 membered heterocycle;

R$_{16}$ is —OH, —OR$_{19}$, —NR$_{26}$R$_{27}$, or substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group;

R$_{17}$ is substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group;

R$_{18}$ is H or substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group; and R$_{19}$ is substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group; and R$_{26}$ and R$_{27}$ independently are H, or substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group.

In another embodiment, R$_{1a}$, R$_{1b}$, and R$_{1c}$ independently are H, OH, methyl, fluoro, dimethylaminomethyl, —NH$_2$, —NO$_2$,

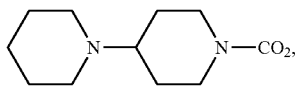

or R$_2$ and R$_{1a}$ together are

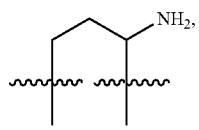 [SMILES: *CCC(*)N]

or R$_{1b}$ and R$_{1c}$ together are

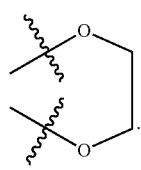

In another embodiment, the compound of the invention is a compound of Formula III:

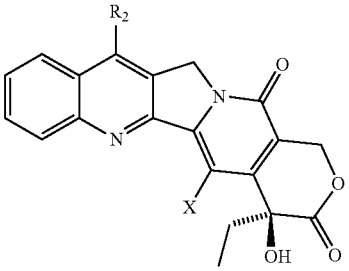

Formula III wherein

R$_2$ is halo, cyano, —CH=Y$_1$, substituted or unsubstituted C$_1$-C$_6$ alkyl, substituted or unsubstituted heteroaryl, or substituted or unsubstituted heterocyclyl group;

X is as defined in Formula I above;

Y$_1$ is O, N—R$_{10}$, or CR$_{11}$R$_{12}$;

R$_{10}$ is —OR$_{13}$, —NR$_{14}$R$_{15}$, substituted or unsubstituted C$_1$-C$_6$ alkyl, substituted or unsubstituted aryl, or substituted or unsubstituted heteroaryl group;

R$_{11}$ is H or substituted or unsubstituted C$_1$-C$_3$ alkyl;

R$_{12}$ is H, substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group, or —COR$_{16}$;

R$_{13}$ is H, substituted or unsubstituted C$_1$-C$_6$ alkyl, substituted or unsubstituted C$_1$-C$_6$ alkenyl, substituted or unsubstituted C$_3$-C$_8$ cycloalkyl, substituted or unsubstituted heterocyclyl, substituted or unsubstituted aryl, or substituted or unsubstituted heteroaryl group;

R$_{14}$ and R$_{15}$ each independently are H, —SO$_2$R$_{17}$, —COR$_{18}$, substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group, or R$_{14}$ and R$_{15}$ together with the nitrogen atom to which they are bonded form a 5-7 membered heterocycle;

R$_{16}$ is —OH, —OR$_{19}$, —NR$_{26}$R$_{27}$, substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group;

R$_{17}$ is substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group;

R$_{18}$ is H or substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group;

R$_{19}$ is substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group; and R$_{26}$ and R$_{27}$ each independently are H, substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group, or R$_{26}$ and R$_{27}$ together with the carbon atom to which they are bonded form a 5-7 membered heterocycle.

In another embodiment, R$_2$ is unsubstituted C$_1$-C$_6$ alkyl.

In another embodiment, the compound of the invention is a compound of Formula IIIA or IIIB, wherein R$_{10}$-R$_{12}$ and X are as defined in Formula III above:

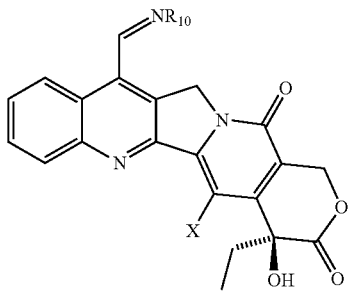

Formula IIIA

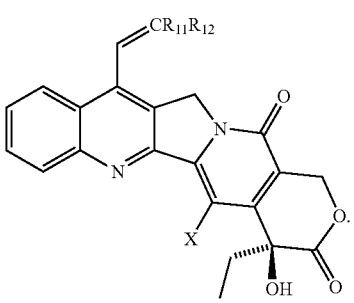

Formula IIIB

In another embodiment, $R_2$ is $-L_1-Z_1$ wherein
$L_1$ is substituted or unsubstituted $C_1-C_6$ alkylene;
$Z_1$ is H, —OH, —ONO$_2$, —Si(R$_{21}$)$_{3}$, —NR$_{22}$R$_{23}$, or —COR$_{24}$;
each $R_{21}$ independently is $C_1-C_3$ alkyl or OH;
$R_{22}$ and $R_{23}$ independently are H, or substituted or unsubstituted $C_1-C_6$ alkyl, substituted or unsubstituted $C_3-C_8$ cycloalkyl, substituted or unsubstituted heterocyclyl, substituted or unsubstituted aryl, or substituted or unsubstituted heteroaryl group, or $R_{22}$ and $R_{23}$ together with the nitrogen atom to which they are bonded form a 5-7 membered heterocycle;
$R_{24}$ is —OH, —OR$_{25}$, substituted or unsubstituted $C_1-C_6$ alkyl, substituted or unsubstituted $C_3-C_8$ cycloalkyl, substituted or unsubstituted heterocyclyl, substituted or unsubstituted aryl, or substituted or unsubstituted heteroaryl group;
$R_{25}$ is substituted or unsubstituted $C_1-C_6$ alkyl, substituted or unsubstituted $C_3-C_8$ cycloalkyl, substituted or unsubstituted heterocyclyl, substituted or unsubstituted aryl, or substituted or unsubstituted heteroaryl group;
and X is as defined in Formula I above.

In another embodiment, $L_1$ is —(CH$_2$)$_n$— wherein n is 1 or 2.

In another embodiment, the compound of the invention is a compound of Formula IVA:

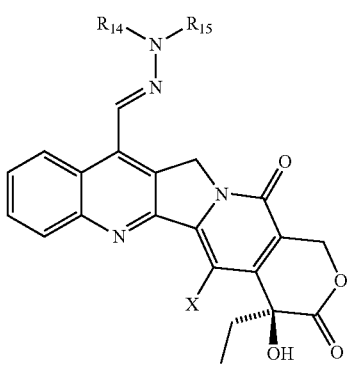

Formula IVA wherein
$R_{14}$ is H, SO$_2$R$_{17}$, or COR$_{18}$, wherein $R_{17}$ and $R_{18}$ are as defined in Formula III above;
$R_{15}$ is -L$_2$-Z$_2$; or $R_{14}$ and $R_{15}$ together with the nitrogen atom to which they are bonded form a 5-7 membered heterocycle;
$L_2$ is substituted or unsubstituted $C_1-C_6$ alkylene;
$Z_2$ is H, —OH, —NR$_{22}$R$_{23}$, or a leaving group; and
$R_{22}$ and $R_{23}$ each independently are H, substituted or unsubstituted $C_1-C_6$ alkyl, substituted or unsubstituted $C_3-C_8$ cycloalkyl, substituted or unsubstituted heterocyclyl, substituted or unsubstituted aryl, or substituted or unsubstituted heteroaryl group, or $R_{22}$ and $R_{23}$ together with the nitrogen atom to which they are bonded form a 5-7 membered heterocycle; and
and X is as defined in Formula I above.

In another embodiment, $L_2$ is —(CH$_2$)$_2$—.

In another embodiment, the compound of the invention is a compound of Formula IVB:

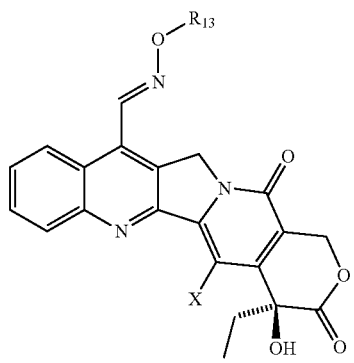

Formula IVB wherein $R_{13}$ is H, or substituted or unsubstituted $C_1-C_6$ alkyl, substituted or unsubstituted $C_1-C_6$ alkenyl, substituted or unsubstituted $C_3-C_8$ cycloalkyl, substituted or unsubstituted heterocyclyl, substituted or unsubstituted aryl, or substituted or unsubstituted heteroaryl group; and X is as defined in Formula I above.

Within the various embodiments hereinabove, $R_{14}$ and $R_{15}$ together with the nitrogen atom to which they are bonded form, in some embodiments, a heterocycle selected from the group consisting of:

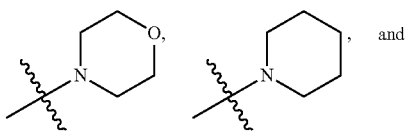

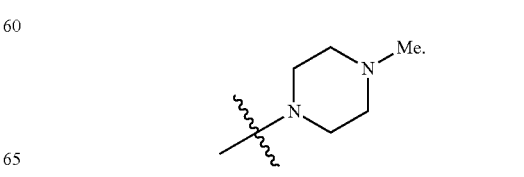

In another embodiment, $R_{13}$ is -$L_3$-$Z_3$ wherein $L_3$ is substituted or unsubstituted $C_1$-$C_6$ alkylene; $Z_3$ is H, OH, $NR_{22}R_{23}$, or a leaving group; and $R_{22}$ and $R_{23}$ independently are H, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group, or $R_{22}$ and $R_{23}$ together with the nitrogen atom to which they are bonded form a 5-7 membered heterocycle. In another embodiment, $L_3$ is —(CH$_2$)$_2$—.

In another embodiment, the compound of the invention is a compound of Formula IVC:

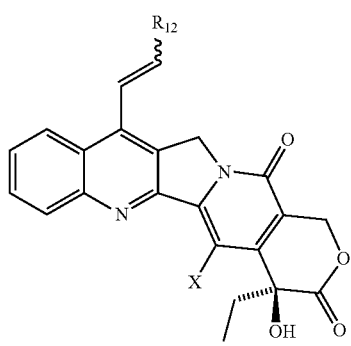

Formula IVC wherein $R_{12}$ is H, —$COR_{16}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; $R_{16}$ is —OH, —$OR_{19}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; and $R_{19}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; and X is as defined in Formula I above.

Within the various embodiments herein, $R_{22}$ and $R_{23}$ each independently are H or methyl, or $R_{22}$ and $R_{23}$ together with the nitrogen atom to which they are bonded form, in some embodiments, a heterocycle selected from the group consisting of:

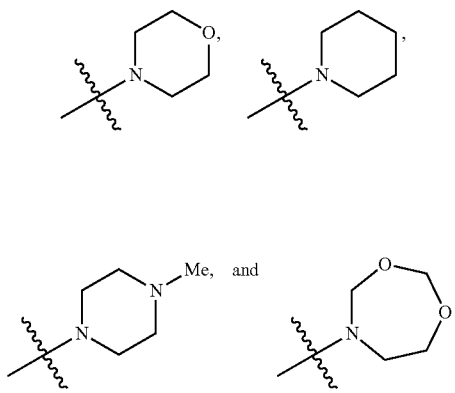

In another embodiment, the compound of the invention is a compound of Formula IVD:

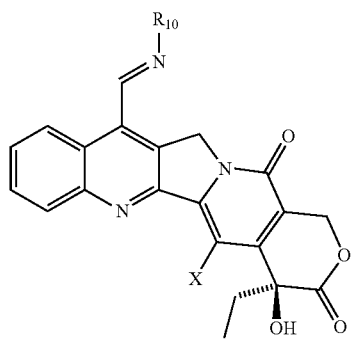

Formula IVD wherein $R_{10}$ is a substituted or unsubstituted aryl or heteroaryl group and X is as defined in Formula I above.

In another embodiment, $R_{10}$ is unsubstituted phenyl or phenyl substituted with one or more (up to 5) substituents selected from the group consisting of halo, hydroxy, or substituted or unsubstituted $C_1$-$C_6$ alkyl.

In another embodiment, the compound of the invention is a compound of Formula V, VA, or VB:

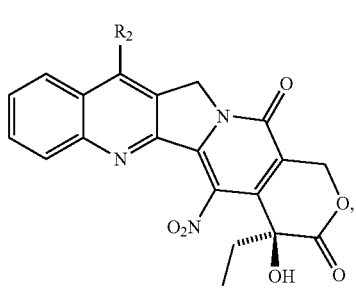

Formula V

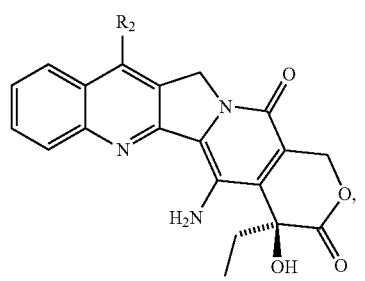

Formula VA

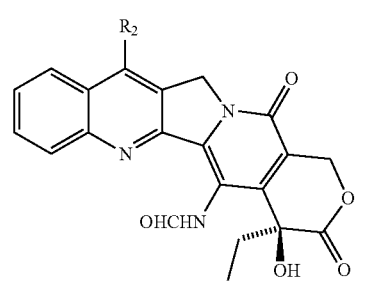

Formula VB wherein $R_2$ is H, substituted or unsubstituted $C_1$-$C_6$ alkyl, halo, or —CH=O. In another embodiment, $R_2$ is not H.

In another embodiment, the compound of the invention is a compound of Formula VI:

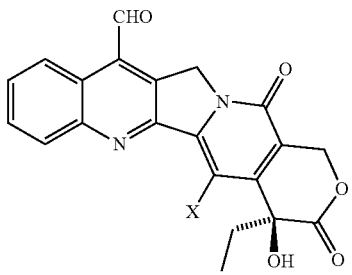

Formula VI wherein X is —NO$_2$, —NH$_2$, —NHCHO, or another substituted amino group as defined in any embodiment herein.

In another embodiment, R$_2$ is —CH(OR$_{20}$)$_2$ or —CHO wherein each R$_{20}$ is independently substituted or unsubstituted C$_1$-C$_6$ alkyl, substituted or unsubstituted C$_3$-C$_8$ cycloalkyl, substituted or unsubstituted heterocyclyl, substituted or unsubstituted aryl, or substituted or unsubstituted heteroaryl group, or the two R$_{20}$ groups together with the oxygen atoms to which they are attached form a 5-6 membered heterocycle. In another embodiment, R$_{20}$ is methyl, ethyl or propyl. In another embodiment, —CH(OR$_{20}$)$_2$ is:

In another embodiment, R$_2$ is substituted or unsubstituted heterocyclyl. In another embodiment, R$_2$ is substituted or unsubstituted aryl. In another embodiment, R$_2$ is substituted or unsubstituted heteroaryl. In another embodiment, R$_2$ is substituted or unsubstituted C$_2$-C$_6$ alkynyl.

In another embodiment, the compound of the invention is a compound of Formula II:

Formula II wherein R$_{1a}$ is H, NO$_2$, or NR$_8$R$_9$
X is nitro or —NR$_3$R$_4$;
R$_3$ and R$_4$ each independently are H, C$_1$-C$_3$ alkyl or COR$_6$;
R$_6$ is H or C$_1$-C$_3$ alkyl;
R$_8$ and R$_9$ each independently are H, C$_1$-C$_3$ alkyl, SO$_2$R$_{31}$, or COR$_{34}$;
R$_{31}$ is substituted or unsubstituted C$_1$-C$_6$ alkyl, substituted or unsubstituted aryl, substituted or unsubstituted heteroaryl, substituted or unsubstituted C$_3$-C$_8$ cycloalkyl, or substituted or unsubstituted heterocycloalkyl; and
R$_{34}$ is H, substituted or unsubstituted C$_1$-C$_6$ alkyl, substituted or unsubstituted aryl, substituted or unsubstituted heteroaryl, substituted or unsubstituted C$_3$-C$_8$ cycloalkyl, or substituted or unsubstituted heterocycloalkyl.

In another embodiment, the present invention provides a compound of Formula I, wherein u=0, and wherein the compound is selected from the group consisting of the compounds wherein:
R$_{1a}$=—CH$_2$NMe$_2$, R$_{1b}$=OH, R$_{1c}$=H; and R$_2$=H (a topotecan derivative);
R$_{1a}$=H, R$_{1b}$=

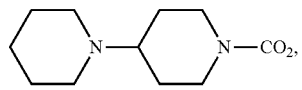

R$_{1c}$=H; and R$_2$=Et (an irinotecan derivative);
R$_{1a}$=H, R$_{1b}$=OH, R$_{1c}$=H; and R$_2$=Et (an SN-38 derivative);
R$_{1a}$=H, R$_{1b}$=OH, R$_{1c}$=H; and R$_2$=—SiMe$_2$CMe$_3$ (a DB 67 derivative);
R$_{1a}$=H, R$_{1b}$=H, R$_{1c}$=H; and R$_2$=—CH$_2$CH$_2$SiMe$_3$ (a BNP 1350 derivative);
R$_2$ and R$_{1a}$=

R$_{1b}$=Me, R$_{1c}$=F (an exatecan derivative);
R$_{1a}$=H, R$_{1b}$ and R$_{1c}$=

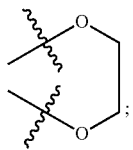 [SMILES: *OCCO*]

and R$_2$=

(a lurtotecan derivative);
R$_{1a}$=R$_{1b}$=R$_{1c}$=H and R$_2$=—CH=N—O—CMe$_3$ (an ST 1481 derivative); and
R$_{1a}$=R$_{1b}$=R$_{1c}$=H and R$_2$=—CH$_2$CH$_2$NHCHMe$_2$ (a CKD 602 derivative).

In another embodiment, the compound of the invention is a compound of any one of the Formulae describing compounds of the invention in which X=—NO$_2$, —NH$_2$, or —NHCHO.

In another embodiment, the present invention provides a compound of Formula I (and any of the other Formulae describing compounds of the invention) wherein u=0, X=NH$_2$ or —NHCHO, and R$_{1a}$=R$_{1b}$=R$_{1c}$=R$_2$=H. In another embodiment, the present invention provides a compound of Formula I (and any of the other Formulae describing compounds of the invention), wherein u=0, X=NO$_2$ and R$_{1a}$=R$_{1b}$=R$_{1c}$=R$_2$=H.

In another embodiment, the present invention provides a compound of Formula I (and any of the other Formulae describing compounds of the invention), wherein $R_2$ is H.

In another embodiment, the present invention provides a compound of Formula I (and any of the other Formulae describing compounds of the invention), wherein $R_2$ is unsubstituted $C_1$-$C_6$ alkyl that is methyl, ethyl, propyl, butyl, pentyl, or neopentyl. In another embodiment, the present invention provides a compound of Formula I (and any of the other Formulae describing compounds of the invention), wherein $R_2$ is substituted $C_1$-$C_6$ alkyl that is —CH(OMe)$_2$, —CH$_2$OH, —CH$_2$ONO$_2$, —CH$_2$CH$_2$CH$_2$SiMe$_3$, —CH$_2$CH$_2$SiMe$_3$, —SiMe$_2$CMe$_3$, —CH$_2$CH$_2$CH$_2$SiMe$_2$OH, —CH$_2$NH$_2$, —CH$_2$NHCH$_2$CMe$_3$, —CH$_2$CH$_2$NHCHMe$_2$, —CH$_2$CH$_2$CO$_2$Me, —CH$_2$CH$_2$CO$_2$CMe$_3$, or —CH$_2$CH$_2$COMe.

In another embodiment, the present invention provides a compound of Formula I (and any of the other Formulae describing compounds of the invention), wherein $R_2$ is —CHO, CN, or halo. In another embodiment, halo is bromo.

In another embodiment, the present invention provides a compound of Formula I (and any of the other Formulae describing compounds of the invention), wherein $R_2$ is —CH=N—O—R$_{13}$, wherein $R_{1a}$ is —CMe$_3$, —CH$_2$CH$_2$NMe$_2$, —CH$_2$CH=CH$_2$,

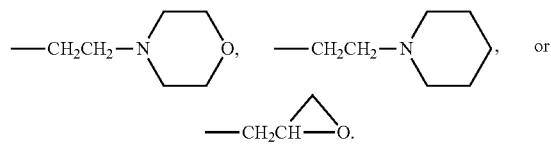

In another embodiment, the present invention provides a compound of Formula I (and any of the other Formulae describing compounds of the invention), wherein $R_2$ is —CH=N—NR$_{14}$R$_{15}$ wherein —NR$_{14}$R$_{15}$ is: —CH=N—NHCH$_2$CH$_2$OH, —CH=N—N(COCH$_3$)CH$_2$CH$_2$OH, —CH=N—N(COCHMe$_2$)CH$_2$CH$_2$OH, —CH=N—N(COCMe$_3$)CH$_2$CH$_2$OH, —CH=N—N(COPh)CH$_2$CH$_2$OH, —CH=N—N(SO$_2$CH$_3$)CH$_2$CH$_2$OSO$_2$Me,

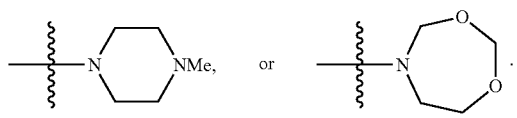

In another embodiment, the present invention provides a compound of Formula I (and any of the other Formulae describing compounds of the invention), wherein $R_2$ is —CH=NR$_{10}$, wherein $R_{10}$ is

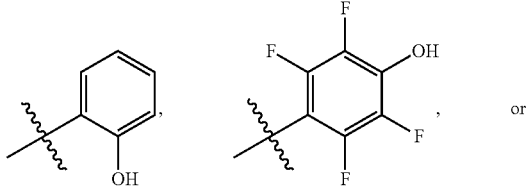

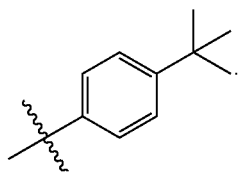

In another embodiment, the present invention provides a compound of Formula I (and any of the other Formulae describing compounds of the invention), wherein $R_2$ is —CH=CHCOR$_{16}$, wherein $R_{16}$ is methyl, —OEt, or —OCMe$_3$.

In another embodiment, the present invention provides a compound of Formula I (and any of the other Formulae provided herein), wherein u is 0. In another embodiment, the present invention provides a compound of Formula I (and any of the other Formulae describing compounds of the invention), wherein u is 1.

Within any of the various embodiments disclosed herein, X can be —NO$_2$, NH$_2$, or —NHCHO.

In another embodiment, the compound is selected from the group of compounds shown in Table 1 below:

TABLE 1

| Structure | TH number |
|---|---|
| ![structure] | TH1317 |
| ![structure] | TH1320 |
| ![structure] | TH1446 |

TABLE 1-continued
| Structure | TH number |
|---|---|
| 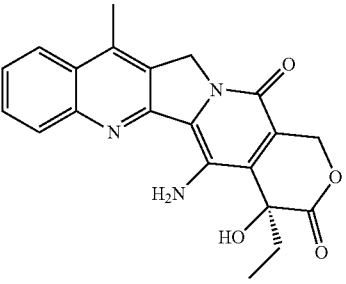 | TH1339 |
| 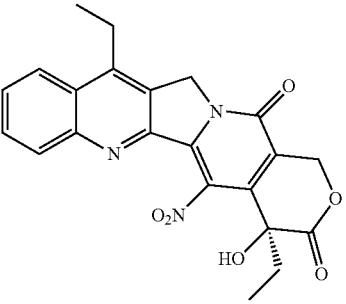 | TH1332 |
| 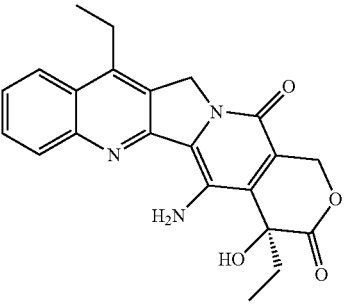 | TH1338 |
| 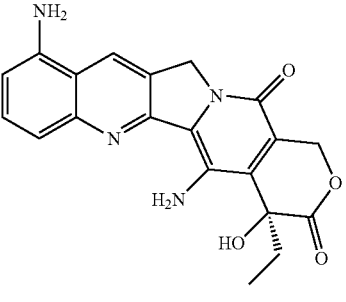 | TH1386 |
| 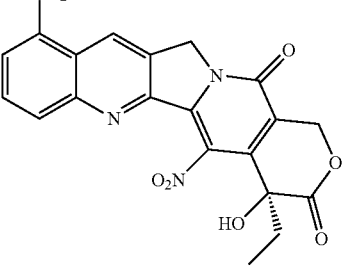 | TH1385 |
| 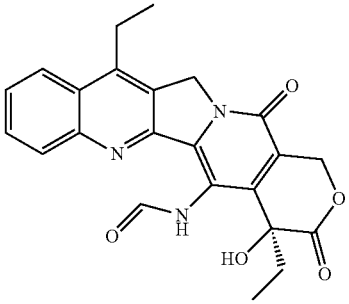 | TH1408 |
| 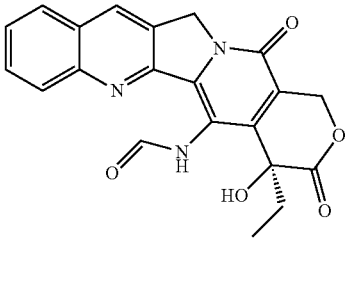 | TH1589 |
| 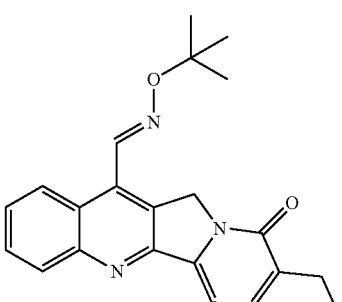 | TH1431 |
| 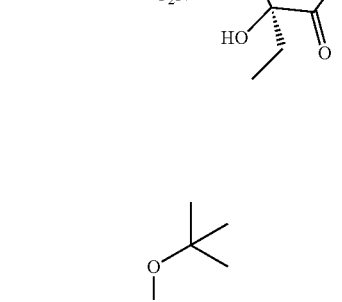 | TH1499 |
| 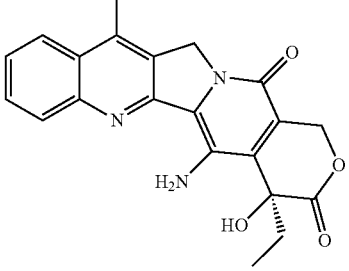 | |

TABLE 1-continued
| Structure | TH number |
|---|---|
| 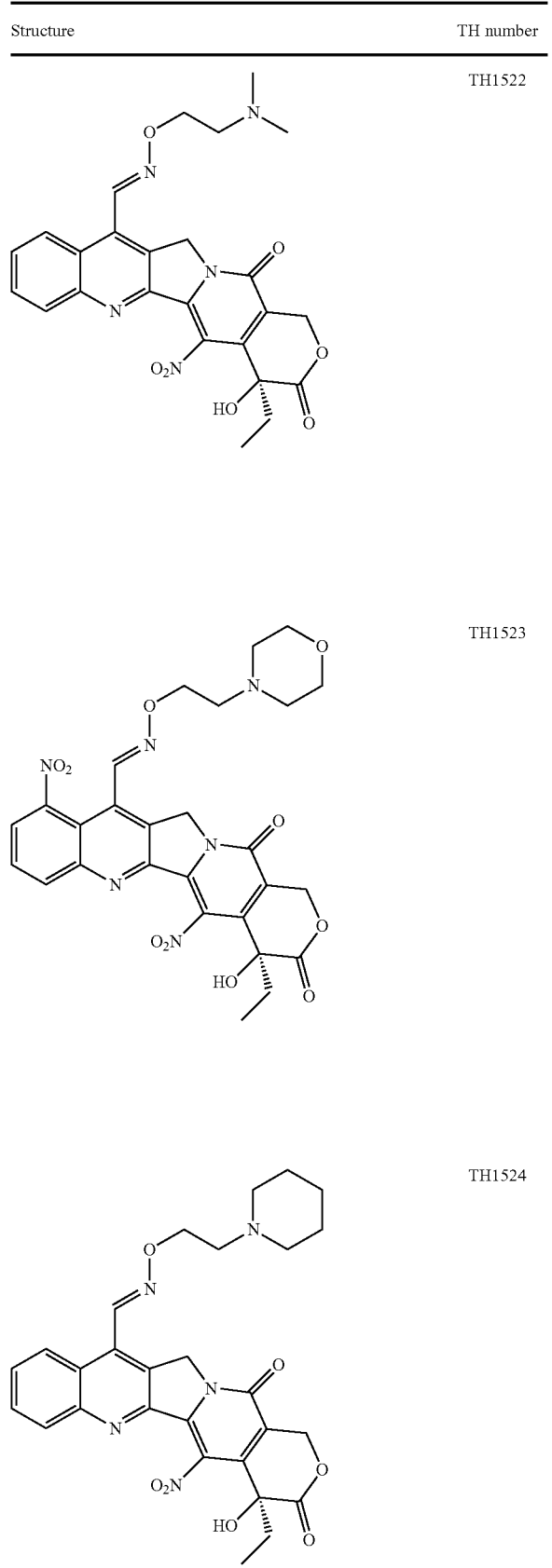 | TH1522 |
| 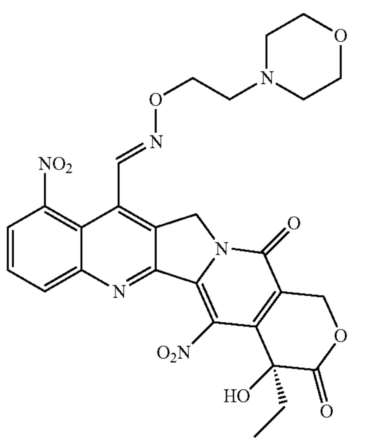 | TH1523 |
| 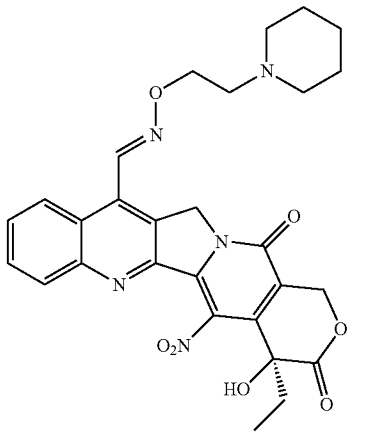 | TH1524 |
TABLE 1-continued
| Structure | TH number |
|---|---|
| 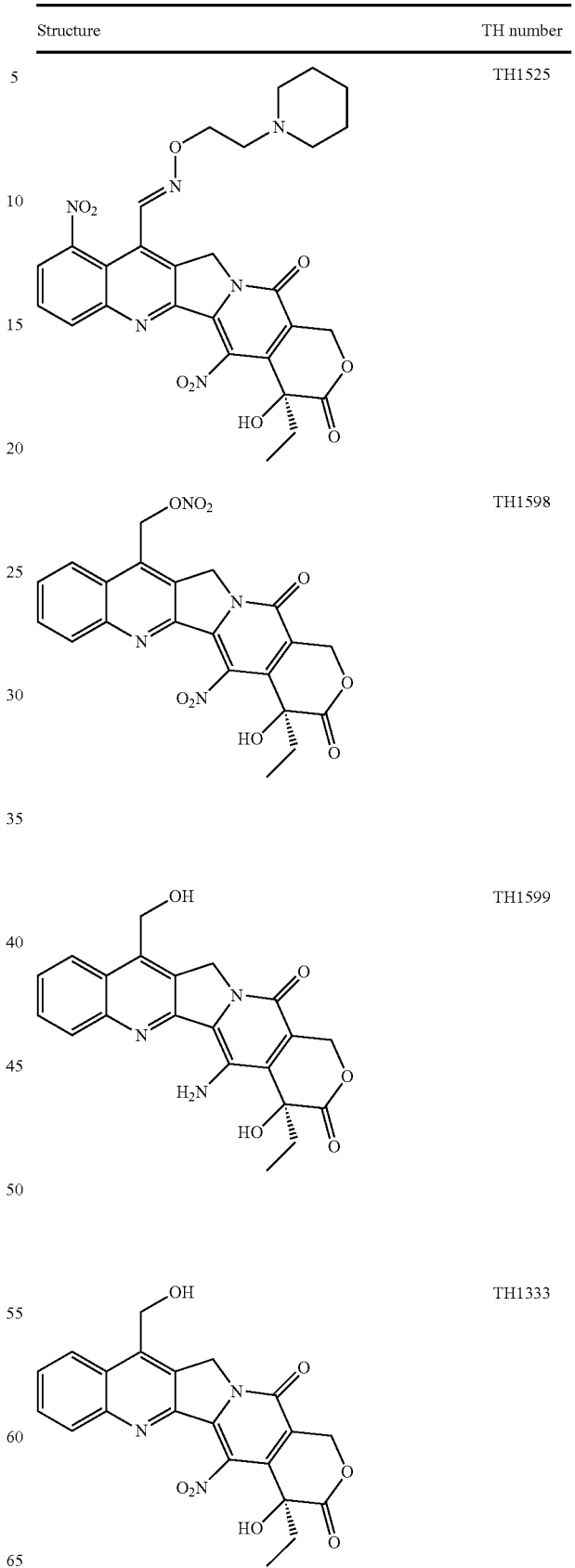 | TH1525 |
| 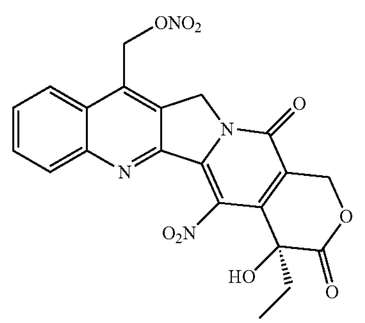 | TH1598 |
| 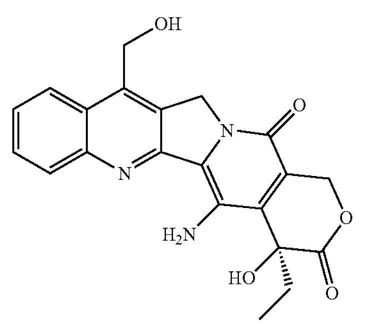 | TH1599 |
| 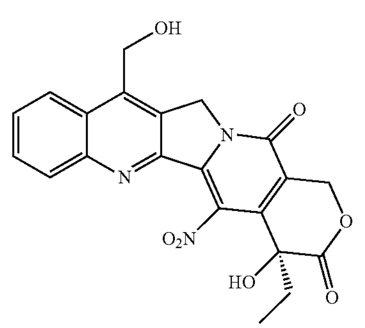 | TH1333 |

TABLE 1-continued

| Structure | TH number |
|---|---|
| (structure) | TH1626 |
| (structure) | TH1627 |
| (structure) | TH1628 |
| (structure) | TH1631 |
| (structure) | TH1636 |
| (structure) | TH1643 |
| (structure) | TH1644 |
| (structure) | TH1650 |
| (structure) | TH1651 |
| (structure) | TH1762 |
| (structure) | TH1766 |

TABLE 1-continued
| Structure | TH number |
|---|---|
| 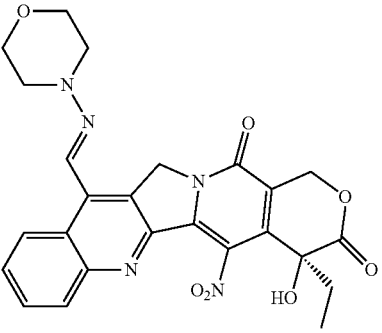 | TH1767 |
| 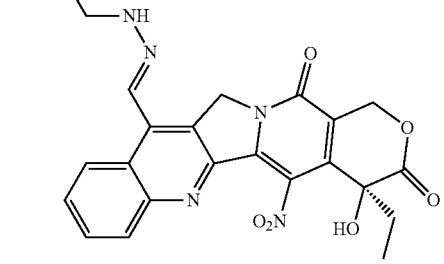 | TH1768 |
| 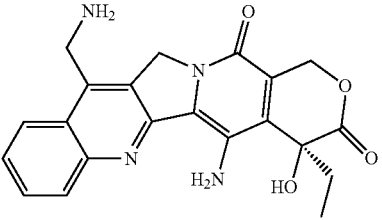 | TH1769 |
| 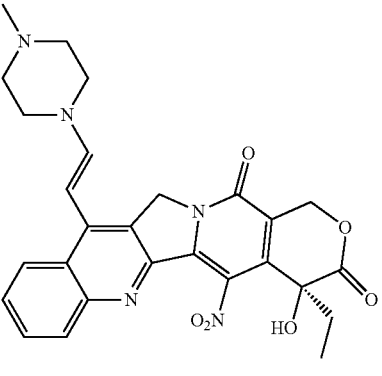 | TH1770 |
| 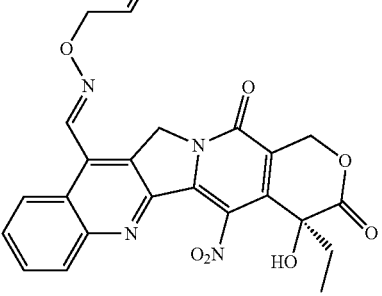 | TH1771 |
TABLE 1-continued
| Structure | TH number |
|---|---|
| 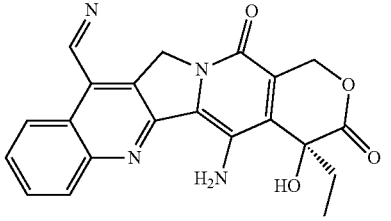 | TH1775 |
| 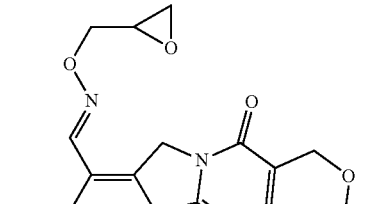 | TH1776 |
| 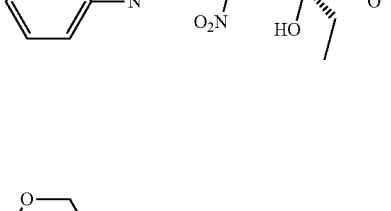 | TH1777 |
| 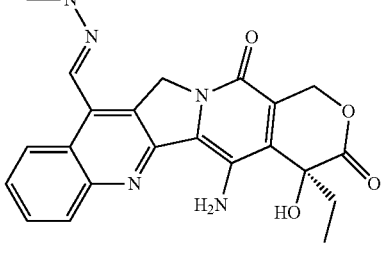 | TH1778 |

TABLE 1-continued
| Structure | TH number |
|---|---|
| 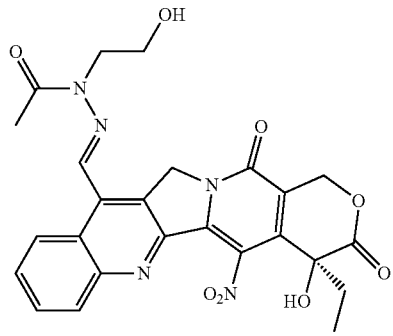 | TH1780 |
| 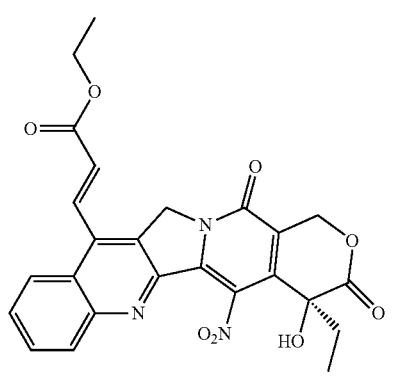 | TH1781 |
| 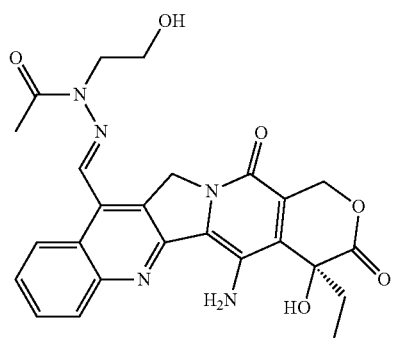 | TH1783 |
| 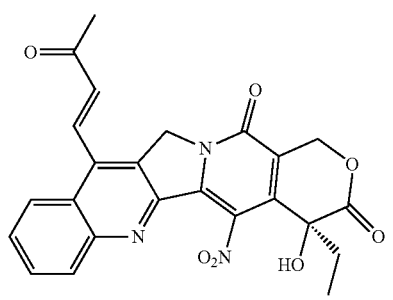 | TH1784 |
| 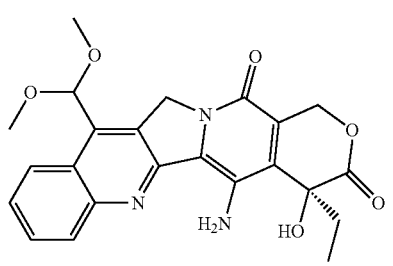 | TH1785 |
TABLE 1-continued
| Structure | TH number |
|---|---|
| 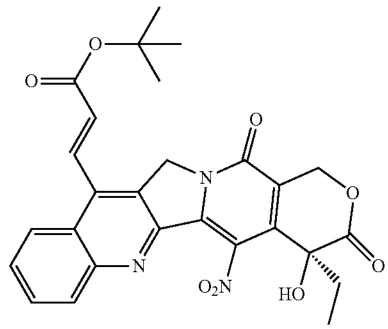 | TH1786 |
| 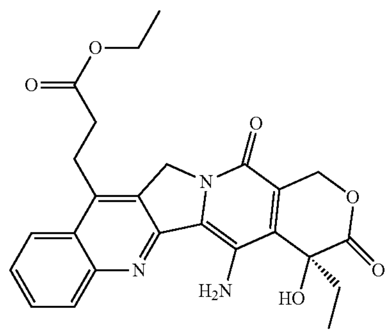 | TH1787 |
| 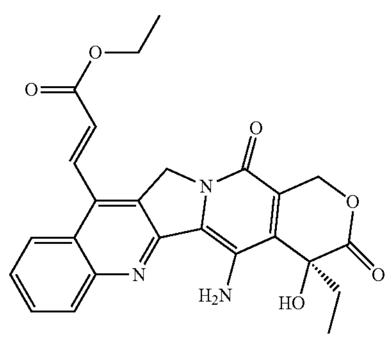 | TH1789 |
| 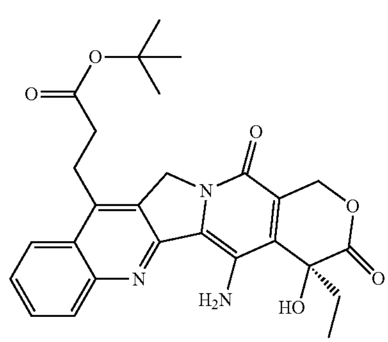 | TH1790 |

TABLE 1-continued
| Structure | TH number |
|---|---|
| 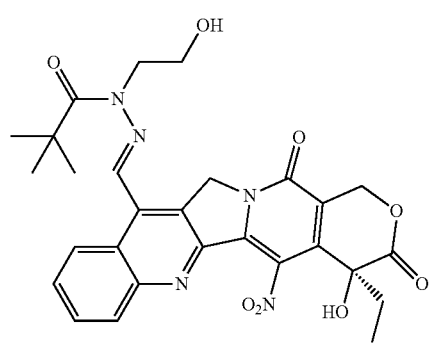 | TH1791 |
| 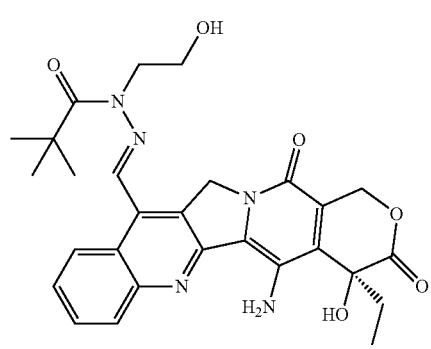 | TH1793 |
| 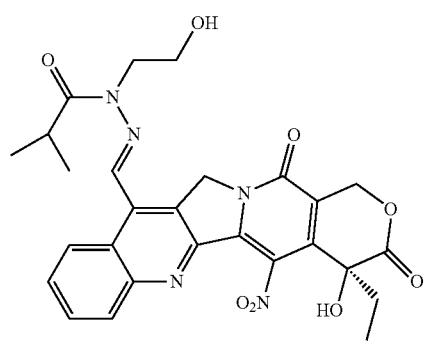 | TH1794 |
| 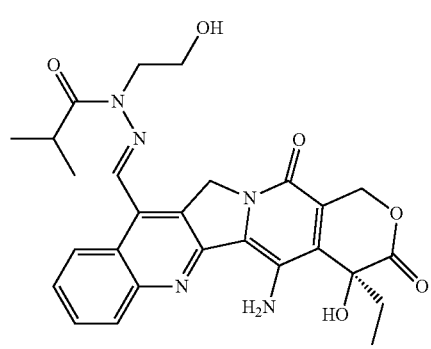 | TH1796 |
TABLE 1-continued
| Structure | TH number |
|---|---|
| 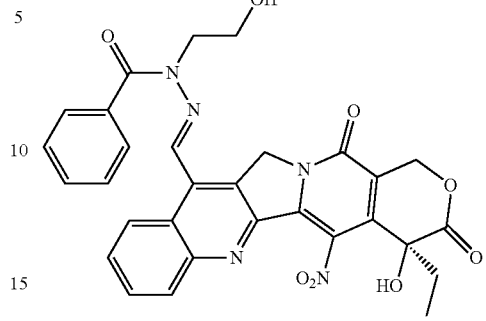 | TH1797 |
| 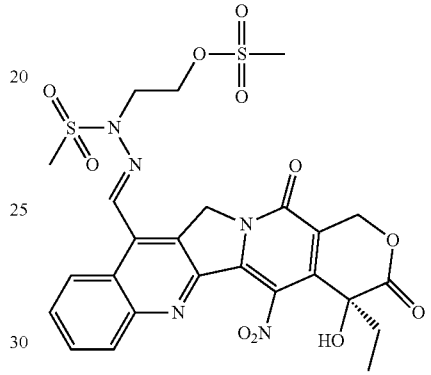 | TH1798 |
| 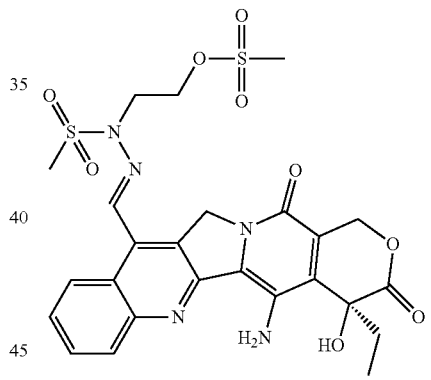 | TH1799 |
| 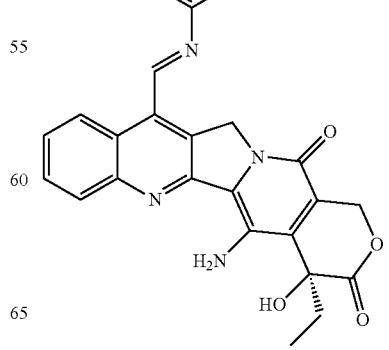 | TH1809 |

TABLE 1-continued
| Structure | TH number |
|---|---|
| 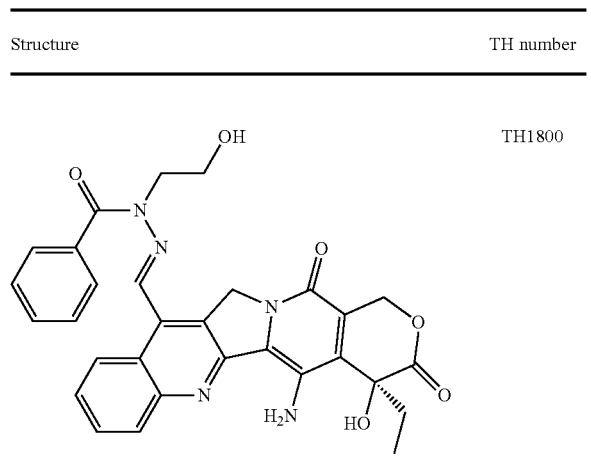 | TH1800 |
| 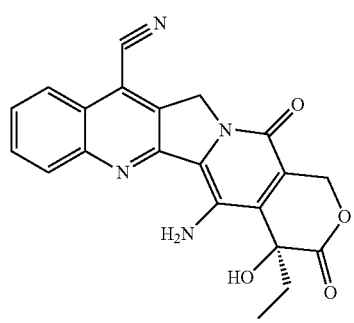 | TH1801 |
| 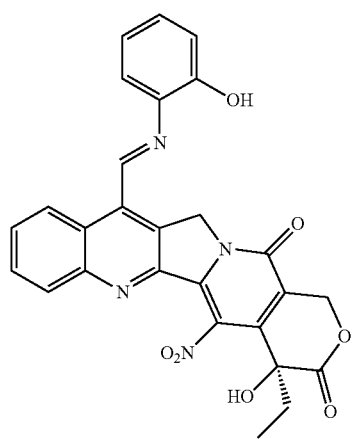 | TH1803 |
| 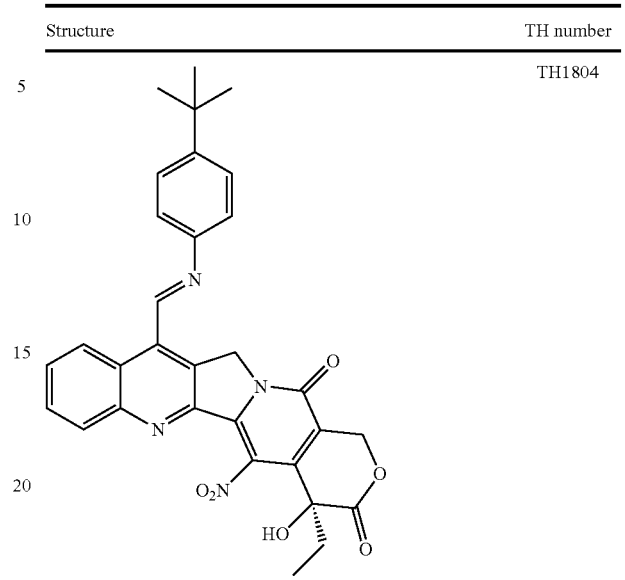 | TH1804 |
| 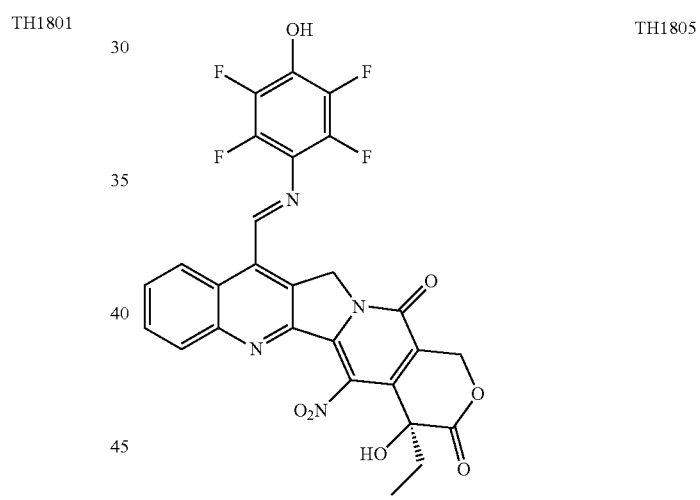 | TH1805 |
| 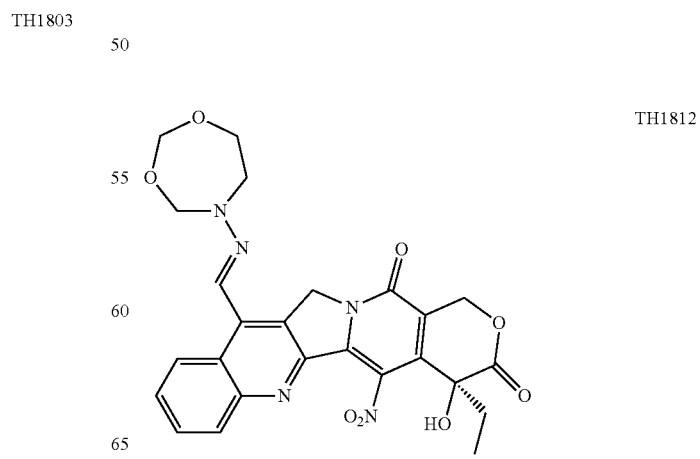 | TH1812 |

TABLE 1-continued

| Structure | TH number |
|---|---|
| 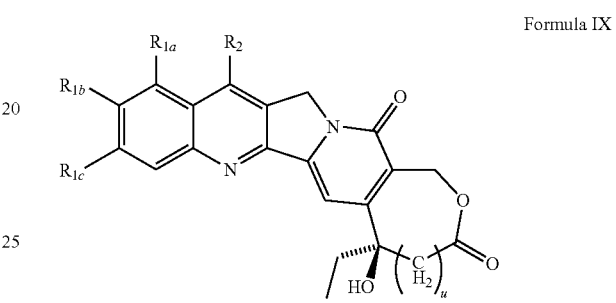 | TH1811 |
| 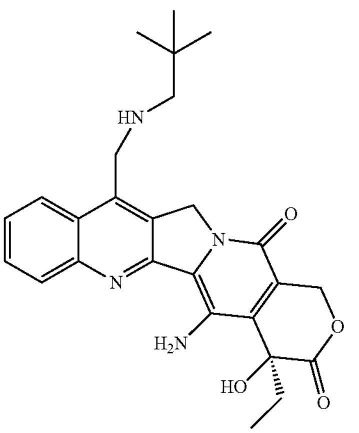 | TH1814 |
| 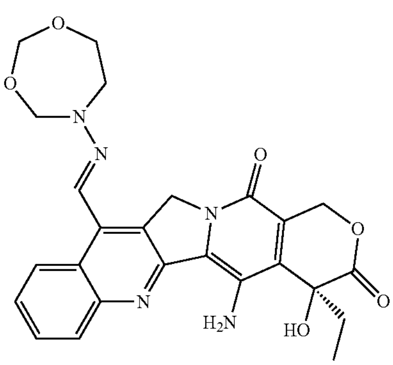 | TH1816 |

In another embodiment, the present invention provides the compounds of the present invention in a substantially pure form. In various embodiments, the compounds of the present invention are provided in a form that is at least 80%, at least 90%, at least 95%, or >99% pure. As used herein, purity refers to the amount of a compound in a composition containing that compound. For example, and without limitation, if x mg of a composition containing a compound of the present invention contains x mg of the compound, then the compound is 100% pure. If x mg of the composition contains y mg of the compound, and (x-y) mg of one or more other compounds, then the purity of the compound is 100(y/x)%. In another embodiment, the present invention provides isolated and substantially pure forms of the compounds. In one embodiment, the substantially pure form of a compound of the invention is prepared under GMP conditions and so is suitable for use in pharmaceutical compositions. Methods of isolating the compounds of the present invention in substantially pure form are provided in the Examples below; moreover, methods for purifying the compounds of the invention can be adapted by one of skill in the art, in view of this disclosure, from known procedures.

In another aspect, the present invention provides compounds prepared by the process comprising, consisting essentially, or consisting of contacting a compound of Formula IX or a salt of ester thereof:

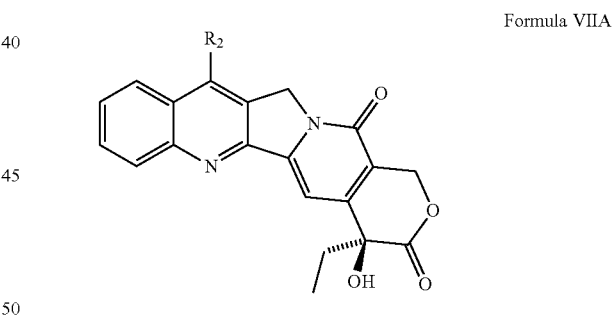

Formula IX wherein u, $R_{1a}$, $R_{1b}$, $R_{1c}$, and $R_2$ are as defined in Formula IX in the Summary of the Invention above, with fuming nitric acid, provided however that the compound prepared excludes 14-nitro-20-acetoxycamptothecin. In one embodiment, u is 0. In another embodiment, u is 1.

In another embodiment, the compound contacted is of Formula VIIA:

Formula VIIA wherein $R_2$ is H, substituted or unsubstituted $C_1$-$C_6$ alkyl, halo, —CH=O or —CH(OR$_{20}$)$_2$ wherein $R_{20}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group.

In one embodiment, $R_2$ is not H. In one embodiment, the contacting is performed in acetic anhydride. In one embodiment, $R_2$ is —CHO or —CH(OR$_{20}$)$_2$. In one embodiment, $R_2$ is H.

Methods of Synthesis

In another aspect, the present invention provides methods for synthesizing the compounds of the present invention comprising, consisting essentially, or consisting of, contacting a compound of Formula IX or a salt or ester thereof:

Formula IX

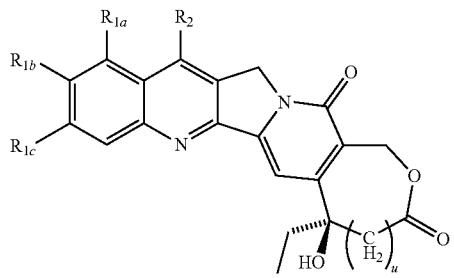

wherein
wherein u, $R_{1a}$, $R_{1b}$, $R_{1c}$, and $R_2$ are as defined in Formula IX in the Summary of the Invention above;
with fuming nitric acid to provide a compound of Formula IXA:

Formula IXA

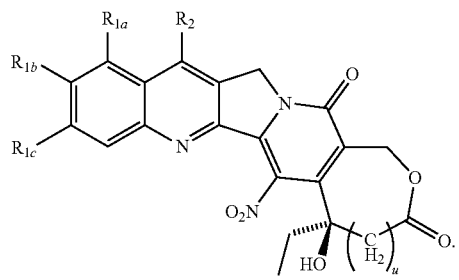

In one embodiment, u=0, and the compound provided is therefore a compound of Formula IA. In another embodiment, u is 1.

In another embodiment, the compound contacted is a compound of Formula VII (u=0) that is selected from the group of compounds wherein:
$R_{1a}$=—CH$_2$NMe$_2$, $R_{1b}$=OH, $R_{1c}$=H; and $R_2$=H (topotecan);
$R_{1a}$=H, $R_{1b}$=

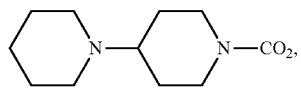

$R_{1c}$=H; and $R_2$=Et (irinotecan);
$R_{1a}$=H, $R_{1b}$=OH, $R_{1c}$=H; and $R_2$=Et (SN-38);
$R_{1a}$=H, $R_{1b}$=OH, $R_{1c}$=H; and $R_2$=—SiMe$_2$CMe$_3$ (DB67);
$R_{1a}$=H, $R_{1b}$=H, $R_{1c}$=H; and $R_2$=—CH$_2$CH$_2$SiMe$_3$ (BNP 1350);
$R_2$ and $R_{1a}$=

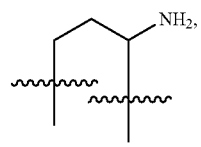

$R_{1b}$=Me, $R_{1c}$=F (Exatecan);

$R_{1a}$=H, $R_{1b}$ and $R_{1c}$=

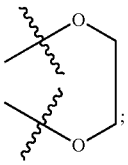

and $R_2$=

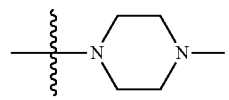 [SMILES: *N1CCN(C)CC1]

(Lurtotecan);
$R_{1a}$=$R_{1b}$=$R_{1c}$=H and $R_2$=—CH=N—O—CMe$_3$ (ST 1481); and
$R_{1a}$=$R_{1b}$=$R_{1c}$=H and $R_2$=—CH$_2$CH$_2$NHCHMe$_2$ (CKD 602).

In another embodiment, the compound contacted is camptothecin.

In one embodiment, the compound contacted is of Formula VIIA:

Formula VIIA

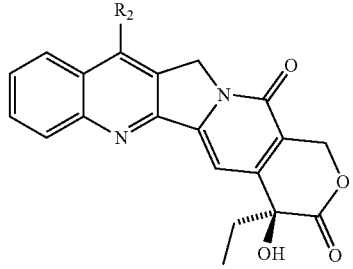

wherein $R_2$ is H, substituted or unsubstituted $C_1$-$C_6$ alkyl, halo, or —CH=O to provide a compound of the invention of Formula V:

Formula V

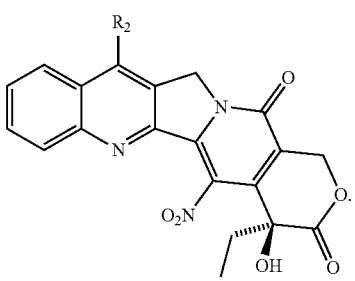

In another embodiment, $R_2$ is H, —CHO, or —CH(OR$_{20}$)$_2$, wherein $R_{20}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group. In another embodiment, $R_2$ is bromo. In another embodiment, $R_2$ is methyl, ethyl, propyl, butyl, pentyl, or hexyl. In one embodiment, the camptothecin derivative contacted is 7-ethyl camptothecin or 7-hydroxymethyl camptothecin. In another embodiment, the contacting is performed in acetic anhydride.

In another embodiment, $R_2$ is —$CH_2$—OH or —$CH_2$—O—$R_{32}$ wherein $R_{32}$ is a hydroxyl protecting group. Various hydroxyl protecting groups useful for this purpose are well known to one of skill in the art. In another embodiment, the method further comprises contacting a compound of Formula IA wherein $R_2$ is —$CH_2$—OH, with an oxidizing agent to provide a compound of Formula IA, wherein $R_2$ is —CHO, or contacting a compound of Formula V wherein $R_2$ is —$CH_2$—OH, with an oxidizing agent to provide a compound of Formula V, wherein $R_2$ is —CHO. A variety of oxidizing agents for converting an alcohol to a formyl group and known to one of skill in the art, including without limitation $MnO_2$, hypervalent iodine reagents, and various chromium based reagents, may be used for this purpose.

In one embodiment, $R_2$ is or —$CH(OR_{20})_2$. In one embodiment, $R_{20}$ is methyl, ethyl or propyl. Within this embodiment, the contacting is, in one embodiment, performed in acetic anhydride. In one embodiment, the method further comprises contacting the compound of Formula IA wherein $R_2$ is —$CH(OR_{20})_2$, with an aqueous acid to provide a compound of Formula IA, wherein $R_2$ is —CHO, and in another embodiment, the method comprises contacting a compound of Formula V wherein $R_2$ is —$CH(OR_{20})_2$, with an aqueous acid to provide a compound of Formula V, wherein $R_2$ is —CHO.

In any of the foregoing embodiments of the synthetic methods of the present invention, in one embodiment, $R_2$ is —CHO. In another embodiment, the contacting can be performed in acetic anhydride.

In another embodiment, the method further comprises contacting the compound of Formula V, wherein $R_2$ is —CHO, with a compound of Formula $H_2N$—$R_{10}$ wherein
$R_{10}$ is —$OR_{13}$, $NR_{14}R_{15}$, or substituted or unsubstituted $C_1$-$C_6$ alkyl, substituted or unsubstituted aryl or substituted or unsubstituted heteroaryl group;
$R_{13}$ is H, or substituted or unsubstituted $C_1$-$C_6$ alkyl, substituted or unsubstituted $C_1$-$C_6$ alkenyl, substituted or unsubstituted $C_3$-$C_8$ cycloalkyl, substituted or unsubstituted heterocyclyl, substituted or unsubstituted aryl, or substituted or unsubstituted heteroaryl group;
$R_{14}$ and $R_{15}$ each independently are H, $SO_2R_{17}$, —$COR_{18}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or unsubstituted heteroaryl group, or $R_{14}$ and $R_{15}$ together with the nitrogen atom to which they are bonded form a 5-7 membered heterocycle;
$R_{17}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;
$R_{18}$ is H or substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group
to provide a compound of Formula IIIA wherein X is —$NO_2$:

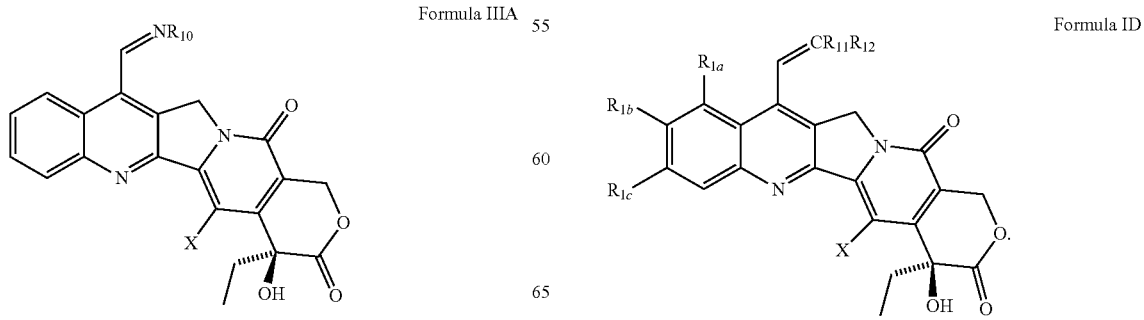

Formula IIIA or, contacting a compound of Formula IA, wherein $R_2$ is —CHO, with a compound of Formula $H_2N$—$R_{10}$, wherein $R_{10}$ is as defined above, to provide a compound of Formula IC wherein X is —$NO_2$:

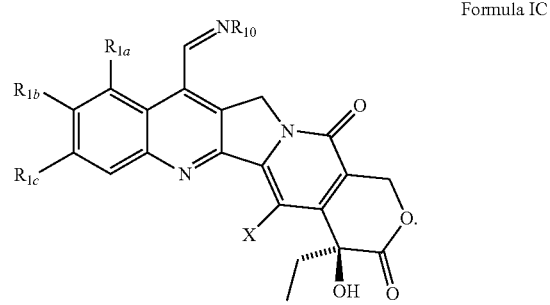

Formula IC

In another embodiment, the method further comprises contacting the compound of Formula V, wherein $R_2$ is —CHO, with a compound of formula $(R_{30})_3P{=}CR_{11}R_{12}$, wherein $R_{11}$ is H or $C_1$-$C_3$ alkyl; $R_{12}$ is H, —$COR_{16}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl; $R_{16}$ is —$OR_{19}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; $R_{19}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; and each $R_{30}$ independently is substituted or unsubstituted $C_1$-$C_6$ alkyl or aryl, to provide a compound of Formula IIIB wherein X is —$NO_2$:

Formula IIIB or, contacting a compound of Formula IA, wherein $R_2$ is —CHO, with a compound of formula $(R_{30})_3P{=}CR_{11}R_{12}$, wherein $R_{11}$, $R_{12}$, and $R_{30}$, are as defined above, to provide a compound of Formula ID wherein X is —$NO_2$:

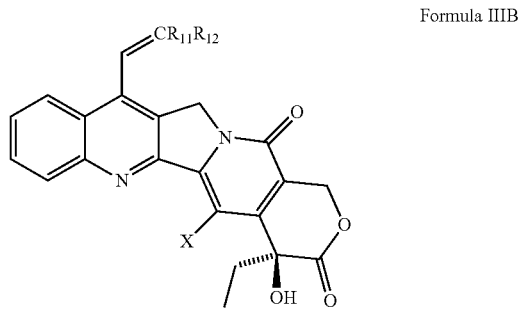

Formula ID

In another embodiment, the method further comprises contacting the compounds provided hereinabove with a reducing agent. A variety of reducing agents may be used in accordance with the present synthetic methods, including, without limitation, Pd/C, Pt/C, PtO$_2$/C, and other heavy metals adsorbed on carbon or other supports, various borohydrides, metal acid reagents, and SnCl$_2$.

In another embodiment, the method further comprises contacting the compounds provided hereinabove, wherein X is —NH$_2$, with HCO$_2$R$_{33}$, R$_5$CO$_2$L, R$_6$COL, or R$_{18}$COL, wherein R$_{33}$ is C$_1$-C$_6$ alkyl, L is a leaving group, and R$_5$, R$_6$, R$_{17}$, and R$_{18}$ are as defined in Formula I and/or III above. A variety of leaving groups can be used in the present synthetic methods, including, without limitation, halo and sulfonates.

In accordance with the present synthetic methods, the compounds contacted with fuming nitric acid can be so contacted in a variety of ways. In one embodiment, the compounds contacted can be added as solids to the fuming nitric acid. In another embodiment, fuming nitric acid can be added to the compounds in acetic anhydride. The contacting can be performed at a variety of temperatures ranging, e.g., from about −10° C. to about 30° C., depending on the nature of the substituents R$_2$ and R$_{1a}$-R$_{1c}$. For example, if the substituent is acid sensitive, a lower temperature may be used. In another embodiment, the compound contacted has a concentration of about 0.01 g/mL to about 1 g/mL. In another embodiment, the compound contacted has a concentration of about 0.01 g/mL to about 0.1 g/mL. In another embodiment, the compound contacted has a concentration of about 0.05 g/mL to about 0.3 g/mL. In another embodiment, the compound contacted has a concentration of about 0.06 g/mL.

One of skill in the art will appreciate that routine steps such as aqueous work-ups and separation of compounds using various known techniques may further be used with the methods of the present invention. One of skill in the art will also appreciate that, for certain chemical transformations, amino, hydroxyl, carboxyl and such other groups may be protected using suitable protecting groups and subsequently deprotected. Suitable protecting groups, and methods of protecting and deprotecting a functional group are well known to one of skill in the art.

The present invention also provides convenient methods for making nitro-camptothecin derivatives specifically and in high yield, for example in yields greater than about 30%, 40%, 50%, and higher yields. Prior methods for making nitro-camptothecin derivatives (such as the 9-nitro and 12-nitro derivatives) used a mixture of nitric and sulfuric acids (see Wani et al., J. Med. Chem. 1986, 29, 2358-2363) that results in low yields. Another method (see Cao, J. Chem. Soc., Perkin Trans. 1, 1996, 2629-32, incorporated herein by reference) used nitronium tetrafluoroborate, an expensive reagent, in acetic anhydride to make (20S)-14-nitro-20-acetoxy-camptothecin, but the reported yield was low.

The syntheses of various compounds of the present invention are schematically shown below:

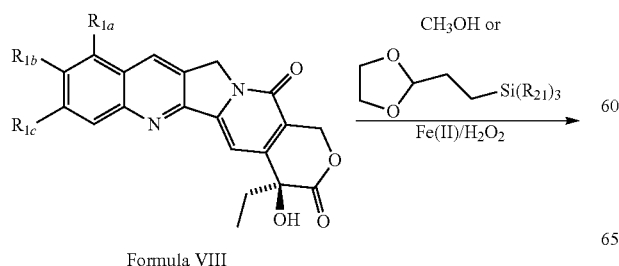

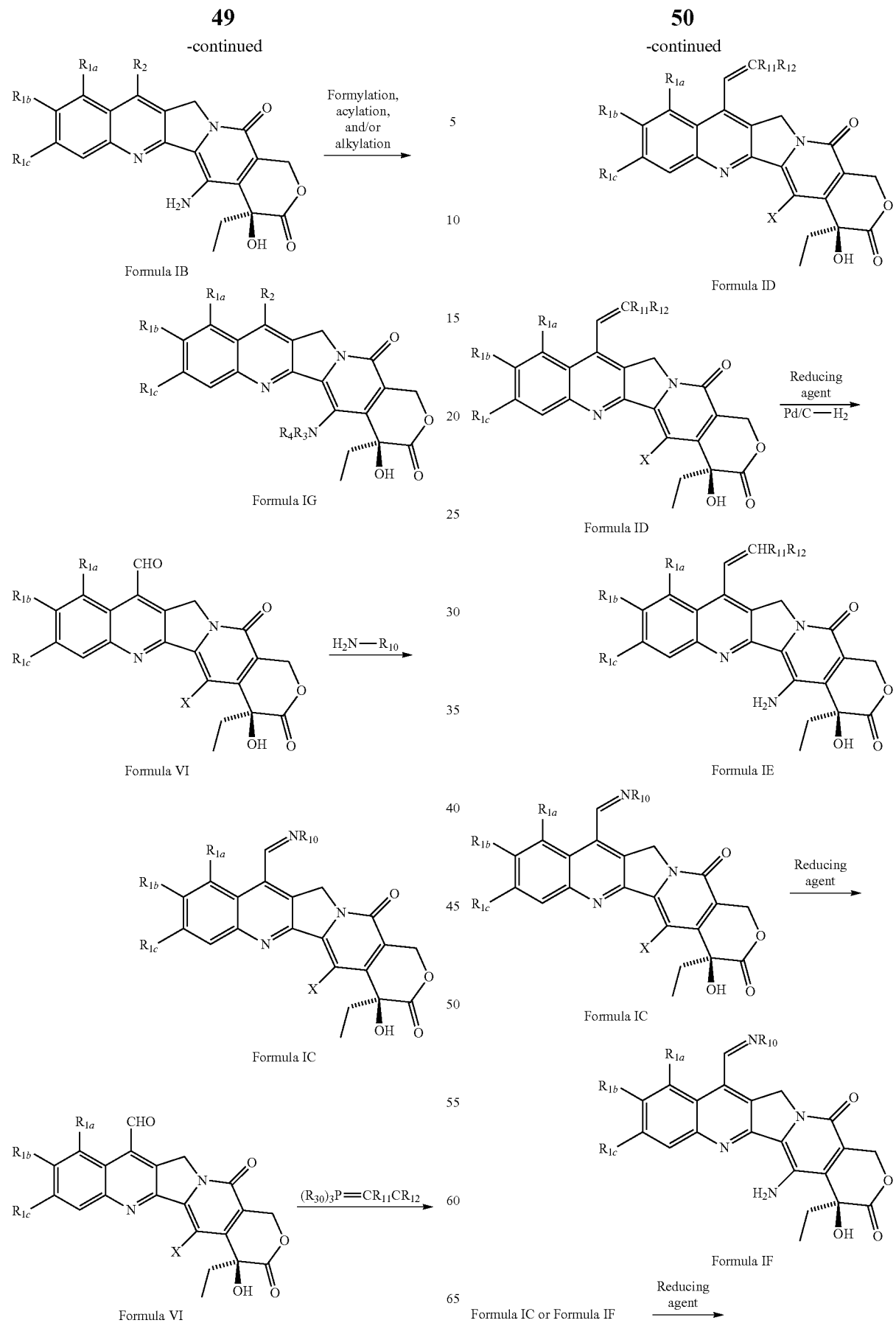

-continued

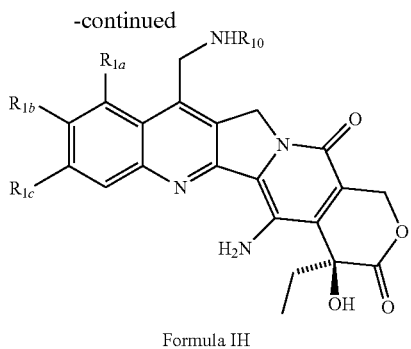

Formula IH

Other compounds of the present invention of Formula I, where u is 1, can be synthesized starting with the higher homolog of a compound of Formula VIII or a compound of Formula IX, using the methods disclosed herein. A useful starting material for synthesizing such other compounds is shown below and can be synthesized as described in Layergne, O. et al., Bioorganic & Medicinal Chemistry Letters, 1997, 7 (17): 2235-38 (incorporated herein by reference):

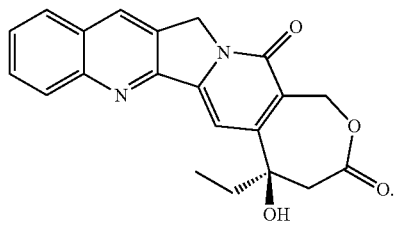

The present synthetic methods of nitration of the camptothecin nucleus, using fuming nitric acid, is an improvement, in terms of regioselectivity and yield, and cost of nitration, over known methods. These synthetic methods of the invention include a milder synthetic method for 14-nitration to yield compounds of Formula I. This milder method of the present invention uses nitric acid as the nitrating agent and is performed in acetic anhydride as the solvent. This method uses relatively small equivalents of fuming nitric acid, and, thus, does not require disposing large amounts of nitric acid.

As described, schematically above and in the examples below, the method using fuming nitric acid and acetic anhydride can be used to synthesize 7-formyl-14-nitrocamptothecin, which is an important compound of the present invention and an important intermediate for synthesizing other compounds of the present invention. For example and without limitation, starting from 7-formyl-14-nitrocamptothecin (TH1672), the 7-cyano derivatives (TH1766 and TH1801) of the invention can be synthesized in good yield. Oxime derivatives of the invention (TH1431, TH1522, and TH1524) can be synthesized by condensation of the aldehyde with the corresponding alkoxyamine. The unsaturated (or alkenyl) ester derivatives of the present invention (TH1781, TH1786, TH1787, TH1789, and TH1790) and unsaturated ketone derivatives of the present invention (TH1784) can be synthesized by Wittig reactions. The hydrazone derivatives of the invention (TH1767, TH1768, TH1770, TH1775, TH1777, and TH1778) and imine derivatives of the present invention (TH1803, TH1804, TH1805, and TH1809) can be synthesized by condensation of the aldehyde with the corresponding hydrazine and anilines in good yields. The methylene amine derivatives (TH1814) can be synthesized by condensation of the aldehyde with the corresponding amine followed by dual reduction of the imine to the amine and the 14-nitro group to the 14 amino group with hydrogen using palladium on carbon as a catalyst. Alternatively the imine can be reduced with sodium borohydride without reduction of the 14-nitro group.

Starting from a compound of the present invention wherein $R_2$ is halo, formyl, or CN, a variety of other compounds of the present invention, wherein $R_2$ is, for example, and without limitation, substituted and unsubstituted aryl, substituted and unsubstituted heteroaryl, or substituted and unsubstituted heterocyclyl can be synthesized using methods known to one of skill in the art in view of the teachings herein. The synthesis of yet other compounds of the present invention will be apparent to one of skill in the art upon reading this disclosure.

Pharmaceutical Compositions and Methods of Use

In another aspect, the present invention provides pharmaceutical compositions comprising, consisting essentially, or consisting of a compound of the present invention or 14-nitro-20-acetoxycamptothecin and a pharmaceutically acceptable carrier, excipient, or diluent. In various embodiments, the pharmaceutical composition further comprises at least another agent (including, but not limited to, an approved cancer drug). Non-limiting examples of the various other agents that can be useful in the pharmaceutical compositions of the present invention are provided hereinbelow. In one embodiment, the pharmaceutical compositions are provided in suitable unit dosage forms appropriate for the particular route of administration to be employed.

In another aspect, the present invention provides a method of inhibiting growth of a cancer or another hyperproliferative cell comprising, consisting essentially, or consisting of contacting the cancer cell or the other hyperproliferative cell with an effective amount of a compound of the present invention, 14-nitro-20-acetoxycamptothecin, or a pharmaceutical composition of the present invention.

In another embodiment, the cancer cells are brain, breast, colon, lung, ovarian, pancreatic or prostate cancer or melanoma cells. In one embodiment, the cancer cells are resistant to another chemotherapy, i.e., the cancer cells are in a patient that has been treated with a prior chemotherapy to which the cancer has become resistant. The contacting can be performed in vitro, as in an in vitro screen or test, or in vivo, as in an animal model, human clinical trial, or treatment of cancer in a human patient.

In various embodiments, the cancer cells sucsceptible to treatment with a compound or pharmaceutical composition of the invention over-express a drug resistance efflux pump, such as MDR1 (Multi drug resistance 1). Examples of such cells include but are not limited to certain breast cancer cells and certain brain cancer cells (e.g., glioblastomas).

In another aspect, the present invention provides a method of treating cancer or another hyperproliferative disease comprising, consisting essentially, or consisting of administering a therapeutically effective amount of a compound of the present invention, 14-nitro-20-acetoxycamptothecin, or a pharmaceutical composition of the present invention to a patient in need of such treatment, thereby treating cancer or the other hyperproliferative disease.

Certain of the 14-nitro camptothecin compounds of the invention are drugs that are converted, under hypoxic conditions, to far more potent anti-cancer drugs that are 14-amino derivatives. In other words, certain 14-nitro compounds of the invention may act as prodrugs. Because fast-growing, malignant tumors often contain poorly-vascularized regions, those regions become hypoxic, and cancer therapies that target the hypoxic regions of tumors are in clinical development (see, for example, PCT Pat. Pub. Nos. 2007/002931, 2008/083101, and 2010/048330, each of which is incorporated herein by reference). Accordingly, the hypoxically-activated 14-nitro compounds of the invention can be particularly useful in methods of treating diseases in which the diseased tissue contains hypoxic areas, regions, or zones. Such diseases include, for example, cancer and other hyperproliferative diseases. TH1332 and TH1431 are 14-nitrocamptothecin derivative compounds of the invention that are drugs activated by hypoxia. As shown in the examples below, these compounds are reduced to the corresponding 14-aminocamptothecin derivatives of the invention TH1338 and TH1499, respectively, under hypoxic conditions. TH1338 is much more potent, or cytotoxic, than TH1332 in killing cancer cells in vitro. The potency of TH1338 and other 14-amino camptothecin derivatives of the present invention was unanticipated and surprising, given that the known 14-chloro camptothecin has greatly reduced potency relative to camptothecin. See, Sawada, S. et al. Chemical & Pharmaceutical Bulletin, 1991, vol. 39, #12, p. 3183-88).

Various compounds and pharmaceutical compositions of the present invention have been demonstrated to be effective in treating cancer as demonstrated by treating xenograft tumors in mice. These in vivo results are described in the Examples below.

Therapeutically effective amounts of the compounds and pharmaceutical compositions of the present invention can be administered in one or more administrations, applications, or dosages. The mode of administration selected will depend on a number of variables, including dosage unit selected, the time period for which treatment is to be continued, the bioavailability of the compound, the route of administration, and other factors known to those of skill in the art. Such factors include the activity of the specific compound employed, the age, body weight, general health, sex, and diet of the subject, the time of administration, the rate of excretion of the drug, whether a drug combination is administered, and the severity of the particular disorder being treated. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art.

The compounds and pharmaceutical formulations of the invention can be administered by any route. Thus, in one embodiment, administration is by the oral route. Certain compounds of the invention suitable for oral administration include: TH1320, TH1332, TH1338, TH1339, TH1346, TH1431. In other embodiments, administration by parenteral (e.g., intramuscular, intraperitoneal, intravenous, ICV, intracisternal injection or infusion, subcutaneous injection, or implant), by inhalation spray nasal, and by vaginal, rectal, sublingual, urethral (e.g., urethral suppository) or topical (e.g., gel, ointment, cream, aerosol, etc.) routes is provided by the invention. Certain compounds of the invention suitable for parenteral administration include: TH1320, TH1338, TH1767, and TH1766.

Compounds of the invention are administered in therapeutically effective doses. In one embodiment, the therapeutically effective dose or amount of the compound administered is a daily dose in the range of 0.01 mg/m$^2$-10,000 mg/m$^2$, 0.1 mg/m$^2$-5000 mg/m$^2$, 1 mg/m$^2$-3000 mg/m$^2$, 10 mg/m$^2$-2000 mg/m$^2$, 100 mg/m$^2$-1000 mg/m$^2$, and 400 mg/m$^2$-800 mg/m$^2$. For an adult human patient, 1 mg/m$^2$ is equal to about 1.7 mg/kg.

In various embodiments, the compounds of the present invention are administered qd, bid, tid, qid, qod, q2d, twice weekly, q7d, or qweek, and treatment is continued for a period ranging from three days to the longer periods.

In certain embodiments, the compounds of the present invention can be administered daily, or once every other day, or once a week to the patient. Multiple daily administrations of a compound of the present invention can also be employed in the methods of the invention. Depending on the dose selected by the practitioner and the convenience of the patient, the entire daily dose may be administered once daily or the daily dose may be administered in multiple smaller doses throughout the course of a day. The compounds of the present invention need not, however, be administered daily; for example a daily dose used for some patients or indications may be, in other patients or for other indications, given every other day, or even less frequently. For example, cancer drugs are often given once a week or even less frequently.

In one embodiment, the daily (or weekly) dose is repeatedly administered over a period of time. In this embodiment, the administration of the therapeutically effective daily dose is continued for multiple days (typically for at least three consecutive days, or for at least a week), or for multiple weeks for several weeks, or for several months, or for several years, or until cancer (or another hyperproliferative disease) or one or more of its symptoms disappears or substantially abates, or up to the rest of the patient's life. As is well understood in the field of medicine, treatment can be suspended temporarily if toxicity is observed or for the convenience of the patient without departing from the scope of the invention.

The methods of cancer treatment employing certain compounds of the present invention, e.g., those, where X is a nitro group, may be more effective in treating cancers with significant hypoxic zones or areas, as these compounds are activated to their more potent derivatives in the hypoxic regions of a tumor or other cancer. Normoxic cancer cells are likewise killed by those activated compounds of this invention (where for example, and without limitation, X is —NH$_2$ or —NH-CHO, or another non-nitro functional group as disclosed herein), but administering the nitro-derivative may be especially efficacious when treating cancers associated with hypoxic cells, tissues, regions, or zones. Any of the compounds of the present invention can be administered in combination with other anticancer agents (including other compounds of the invention) or other anticancer therapies.

Thus, in another embodiment, the present invention provides a method of treating cancer and other hyperproliferative diseases comprising, consisting essentially, or consisting of administering a therapeutically effective amount of a compound or pharmaceutical composition of the present invention in combination with another anticancer agent or anticancer therapy to a patient in need of such treatment. The other agents can be administered as the same or as a different formulation and can be administered via the same or a different route of administration. In another embodiment, this invention provides the use of a compound of this invention in the manufacture of a medicament for treating cancer or another hyperproliferative disease in a patient, wherein the medicament is for use in combination with the administration of another anticancer agent or anticancer therapy.

Thus, in accordance with the methods of the invention, a compound of the present invention can be coadministered in combination with other anticancer agents. As used herein, a compound of the present invention is coadministered with another anticancer agent (also referred to herein as, "the other agent") when a compound of the present invention and the other agent are administered as part of the same course of therapy. The coadministration of a compound of the present invention may increase the sensitivity of cancer cells to the other anticancer agent, allowing lower doses of the anticancer agent to be administered to the patient, or allowing an anticancer agent to be used for treatment of cells otherwise resistant to the anticancer agent or otherwise refractory to treatment.

Without intending to be bound by any particular mechanism or effect, such coadministration can in some cases provide one or more of several advantages over known cancer therapies. For example, coadministration of a compound of the present invention and another anticancer agent may have a synergistic effect on induction of cancer cell death. Two drugs can be said to possess therapeutic synergy if a combination dose regimen of the two drugs produces a better tumor cell kill than the sum of the constituent single agents at optimal or maximum tolerated doses.

Coadministration of anti cancer agents in accordance with the present treatment methods may provide a better therapeutic result than administration of either of the coadministered anticancer agents alone. Such coadministration can provide greater alleviation or amelioration of one or more symptoms of the cancer, diminishment of extent of disease, delay or slowing of disease progression, amelioration, palliation or stabilization of the disease state, reduced toxicity, partial or complete remission, prolonged survival or other beneficial therapeutic results.

In one embodiment, a compound of the present invention is first administered prior to administration of the other agent, (i.e., the initiation of the other cancer therapy), and treatment with a compound of the present invention is continued throughout the course of administration of the other agent (i.e., the course of the other therapy). In another embodiment, a compound of the present invention is administered after the initiation or completion of the other cancer therapy. In other embodiments, a compound of the present invention is administered contemporaneously with the initiation of the other cancer therapy. Therefore, when a compound of the present invention is used in combination with one or more of the additional therapies, a compound of the present invention and additional therapy can be administered at the same time or can be administered separately. For hypoxia-activated anti-cancer prodrugs, the order of administration of a combination drug therapy can have important effects on efficacy and safety. See PCT Pub. No. 2010/048330, incorporated herein by reference.

In one embodiment, a compound of the present invention is first administered prior to administration of the other agent, and treatment with a compound of the present invention is continued after the cessation of administration of the other agent. In one embodiment, a compound of the present invention is first administered prior to administration of the other agent, and treatment with a compound of the present invention is continued during part of the period of administration of the other agent. For certain drugs, such as certain topoisomerase inhibitors, therapy with a compound of the present invention can be initiated and completed prior to the administration of the second drug.

Anticancer drug therapy typically involves multiple rounds, or cycles, of administration of the anti-cancer drug. In the context of coadministering a compound of the present invention, each cycle of administration (as well as a complete set of cycles) of a first cancer drug can be viewed as an opportunity for coadministration of a second anti-cancer drug. In other words, a compound of the present invention can be administered in any or all of the multiple cycles of treatment with another drug or agent. In general, a compound or composition of the present invention may be administered on a daily basis for a day, or two or more days, during each cycle. In one embodiment of the invention, a compound or composition of the present invention is coadministered with the other agent according to a schedule repeated during each cycle.

These methods can be used to improve patient outcomes over currently practiced therapies by more effectively killing cancer or other hyperproliferative cells or by stopping growth of cancer cell as well as diminishing unwanted side effects of the other therapy. When employed in combination with a compound of the present invention, the additional anti-cancer agent(s) may be dosed using the standard dosages employed for those other agents (i.e., when used without a compound of the present invention) or may be less than those standard dosages.

In some embodiments, the other agent coadministered with a compound or composition of the present invention will be delivered at a lower dose, and optionally for longer periods, than would be the case in the absence of administering the compound of the present invention. Such "low dose" therapies can involve, for example, administering an anti cancer drug, at a lower than the approved dose and/or for a longer period of time together with a compound of the present invention administered in accordance with the methods described herein.

Specific dose regimens for known and approved chemotherapeutic agents or antineoplastic agents (i.e., the recommended effective dose) are known to physicians and are given, for example, in the product descriptions found in the current edition of the Physician's Desk Reference, Medical Economics Company, Inc., Oradell, N.J.; Goodman and Gilman's The pharmacological basis of therapeutics. Eds. Hardman et al., McGraw-Hill. New York. (US) 1996, 9th Ed., and/or are available from the Federal Drug Administration. Illustrative dosage regimens for certain anti cancer drugs are also provided below.

Other anti-cancer agents useful in combination therapies with the compounds and compositions of the present invention can generally be classified as alkylators, anthracyclines, antibiotics, aromatase inhibitors, bisphosphonates, cyclooxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase or other kinase inhibitors. In accordance with the methods described herein, a compound or composition of the present invention can be coadministered with any anti cancer drug from any of these classes or can be administered prior to or after treatment with any such drug or combination of such drugs. In addition, a compound or composition of the present invention can be administered in combination with a biologic therapy (e.g., treatment with interferons, interleukins, colony stimulating factors and monoclonal antibodies). Biologics used for treatment of cancer are known in the art and include, without limitation, avastin, trastuzumab (Herceptin), cetuximab (Erbitux) tositumomab $^{131}$I (Bexxar), and rituximab (Rituxan).

In one embodiment, the other agent is a chemotherapeutic agent that can be used in combination with the compound of the present invention of the invention. Such chemotherapeutic agents include, but are not limited to, busulfan, improsulfan, piposulfan, benzodepa, carboquone, 2-deoxy-D-glucose, lonidamine and analogs thereof, glufosfamide, gemcitibine, erlotinib, meturedepa, uredepa, altretamine, imatinib, triethylenemelamine, triethylenephosphoramide, triethylenethiophosphoramide, trimethylolomelamine, chlorambucil, chlornaphazine, estramustine, ifosfamide, gefitinib, mechlorethamine, mechlorethamine oxide hydrochloride, melphalan, novembichin, phenesterine, prednimustine, trofosfamide, uracil mustard, carmustine, chlorozotocin, fotemustine, nimustine, ranimustine, dacarbazine, mannomustine, mitobronitol, mitolactol, pipobroman, aclacinomycins, actinomycin, anthramycin, azaserine, bleomycin, cactinomycin, carubicin, carzinophilin, chromomycin, dactinomycin, daunorubicin, daunomycin, 6-diazo-5-oxo-1-norleucine, mycophenolic acid, nogalamycin, olivomycin, peplomycin, plicamycin, porfiromycin, puromycin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, 5-fluorouracil, tegafur, L-asparaginase, pulmozyme, aceglatone, aldophosphamide glycoside, aminolevulinic acid, amsacrine, bestrabucil, bisantrene, cisplatin, oxoplatin, carboplatin, defofamide, demecolcine, diaziquone, elformithine, elliptinium acetate, etoglucid, flutamide, gallium nitrate, hydroxyurea, interferon-alpha, interferon-beta, interferon-gamma, interleukin-2, lentinan, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, erlotonib, teniposide, tenuazonic acid, triaziquone, 2,2',2"-trichlorotriethylamine, urethan, vinblastine, cyclophosphamide, and vincristine. Combination treatment including various compounds or compositions of the present invention and the other agents are further disclosed below.

In one embodiment, a compound or composition of the present invention can be used in combination with an angiogenesis inhibitor (anti-angiogenic agent) including, but not limited to, avastin and similar therapeutics. In one embodiment of the combination treatment methods, a subject is treated with an angiogenesis inhibitor and subsequently treated with a compound or composition of the present invention. In one embodiment of the combination treatment methods, a subject is treated with an angiogenesis inhibitor and subsequently treated with a compound or composition of the present invention, and with another chemotherapeutic agent, including, but not limited to, cisplatin, and carboplatin. In other embodiments, the compound or composition of the present invention is administered contemporaneously or before administering the anti-angiogenic agent. In one embodiment of these combination methods of treatment using an angiogenesis inhibitor, the method is used to treat breast cancer.

Non-limiting examples of anti angiogenic agents include, without limitation, angiostatin, an agent that inhibits or otherwise antagonizes the action of VEGF, batimastat, captopril, cartilage derived inhibitors, genistein, endostatin, interleukin, lavendustin A, medroxyprogesterone acetate, recombinant human platelet factor 4, taxol, tecogalan, thalidomide, thrombospondin, TNP-470, and avastin. Other useful angiogenesis inhibitors useful for the combination therapies provided by the present treatment methods include Cox-2 inhibitors like celecoxib (Celebrex), diclofenac (Voltaren), etodolac (Lodine), fenoprofen (Nalfon), indomethacin (Indocin), ketoprofen (Orudis, Oruvail), ketorolac (Toradol), oxaprozin (Daypro), nabumetone (Relafen), sulindac (Clinoril), tolmetin (Tolectin), rofecoxib (Vioxx), ibuprofen (Advil), naproxen (Aleve, Naprosyn), aspirin, and acetaminophen (Tylenol).

In another embodiment, a compound or composition of the present invention is administered with an anti cancer agent that acts, either directly or indirectly, to inhibit the epidermal growth factor or EGFR receptor. EGFR inhibitors suitable for coadministration with a compound or composition of the present invention of the invention include gefitinib and erlotonib.

In another embodiment, a compound or composition of the present invention is administered in accordance with the present treatment methods with an anti cancer agent that acts, either directly or indirectly, to inhibit hypoxia-inducible factor 1 alpha (HIF1α) or to inhibit a protein or enzyme, such as a glucose transporter or VEGF, whose expression or activity is increased upon increased HIF1α levels. HIF1α inhibitors suitable for use in this embodiment of the methods and compositions described herein include P1 3 kinase inhibitors; LY294002; rapamycin; histone deacetylase inhibitors such as [(E)-(1S,4S,10S,21R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-I) inhibitors such as PD98059 (2'-ammo-3'-methoxyflavone); PX-12 (1-methylpropyl 2-imidazolyl disulfide); pleurotin PX-478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; and topotecan, irinotecan, or camptothecin derivatives other than those provided herein.

Alkylators useful in the practice of the present treatment methods include, but are not limited to, busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), mechlorethamine, temozolamide (Temodar), carmustirie, streptozocin, bendamustin, busulfan, thiotepa, cisplatin, carboplatin, and oxaliplatin. In accordance with the methods described herein, a compound or composition of the present invention is coadministered with an alkylator to treat cancer. In one embodiment, the compounds are compositions of the present invention are co-administered with TH-302. In one embodiment, the cancer is chronic myelogenous leukemia, multiple myeloma, or anaplastic astrocytoma.

Nitrosoureas useful in the practice of the present treatment methods described herein include, but are not limited to, procarbazine (Matulane), lomustine (CCNU), carmustine (BCNU, and Gliadel Wafer), and estramustine (Emcyt). In accordance with the methods described herein, a compound or composition of the present invention is coadministered with a nitrosourea to treat cancer. In one embodiment, the cancer is prostate cancer or glioblastoma, including recurrent glioblastoma multiforme.

In one embodiment, the present invention provides a method of treating cancer by coadministering a compound or composition of the present invention with at least the alkylator cyclophosphamide, in the treatment of Stages III and IV malignant lymphomas, multiple myeloma, leukemia, mycosis fungoides, neuroblastoma, ovarian adenocarcinoma, retinoblastoma, and carcinoma of the breast.

In one embodiment, the present invention provides a method of treating cancer or another hyperproliferative disease by administering a compound or composition of the present invention with a cancer treatment regimen using at least the alkylator ifosfamide. Ifosfamide is used to treat pediatric and adult sarcomas, carcinomas of cervix and lung, and in combination with other drugs for germ cell testicular cancer. Ifosfamide is used as part of the ICE (ifosfamide, carboplatin, and etoposide) ans RICE (rituxan and ICE) regimens for treating lymphomas (see Hardman et al., supra).

In one embodiment, the present invention provides a method of treating cancer or another hyperproliferative disease by administering a compound or composition of the invention with a cancer treatment regimen using at least the alkylator glufosfamide. Glufosfamide can be used for treating pancreatic cancer or Gemzar resistant pancreatic cancer, breast cancer, Morbus Hodgkin, gastrointestinal tract cancer, or as part of the GCE (glufosfamide, carboplatin, and etoposide) or RGCE (rituxan and GCE) regimen, lymphomas. (See, e.g., U.S. Pat. No. 5,622,936 and PCT Pat. Pub. No. WO 2005/076888, each of which is incorporated in their entirety herein by reference).

In one embodiment, the present invention provides a method of treating cancer or another hyperproliferative disease by administering a compound or composition of the present invention of the invention with a cancer treatment regimen using at least a platinum coordination complex alkylator. In one embodiment, the platinum coordination complex alkylator is cisplatin. Cisplatin can be used to treat cancer of bladder, head and neck, endometrium, small cell carcinoma of the lung, and some neoplasms of childhood. Cisplatin alone or with cyclophosphamide is used to treat advanced ovarian cancer. Combination chemotherapy of cisplatin with bleomycin, etoposide, and vinblastine is used to treat advanced testicular cancer; and with one of paclitaxel, cyclophosphamide, or doxorubicin to treat ovarian carcinoma.

In another embodiment, the cancer is metastatic testicular cancer, metastatic ovarian cancer, ovarian carcinoma, and transitional cell bladder cancer. As one example, cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50-70 mg/m$^2$ once every three to four weeks. In accordance with the methods described herein, a compound or composition of the present invention is coadministered with cisplatin administered at these doses (or at lower doses). One or more additional anti cancer agents can be coadministered with the platinum compound and a compound or composition of the present invention. As one example, platinol, blenoxane, and velbam can be coadministered with a compound or composition of the present invention. As another example, platinol and adriamycin can be coadministered with a compound or composition of the present invention.

Anthracyclines useful in the practice of the present treatment methods include, but are not limited to, doxorubicin (Adriamycin, Doxil, Rubex), mitoxantrone (Novantrone), idarubicin (Idamycin), valrubicin (Valstar), and epirubicin (Ellence). In accordance with the methods described herein, a compound or composition of the present invention is coadministered with an anthracycline to treat cancer. In one embodiment, the cancer is acute nonlymphocytic leukemia, Kaposi's sarcoma, prostate cancer, bladder cancer, metastatic carcinoma of the ovary, or breast cancer.

Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 30-75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the methods described herein, a compound or composition of the present invention is coadministered starting prior to and continuing after the administration of doxorubicin at such doses (or at lower doses).

Antibiotics useful in the practice of the present treatment methods include, but are not limited to, dactinomycin, actinomycin D (Cosmegen), bleomycin (Blenoxane), daunorubicin (Cerubidine, DanuoXome). In accordance with the methods described herein, a compound or composition of the present invention is coadministered with an antibiotic to treat cancer. In one embodiment, the cancer is a cancer selected from the group consisting of acute lymphocytic leukemia, other leukemias, and Kaposi's sarcoma.

Aromatase inhibitors useful in the practice of the present treatment methods include, but are not limited to, anastrozole (Arimidex) and letrozole (Femara). In accordance with the methods described herein, a compound of the present invention is coadministered with an aromatase inhibitor to treat cancer. In one embodiment, the cancer is breast cancer.

Bisphosphonate inhibitors useful in the practice of the present treatment methods include, but are not limited to, zoledronate (Zometa). In accordance with the methods described herein, a compound or composition of the present invention is coadministered with a biphosphonate inhibitor to treat cancer. In one embodiment, the cancer is a cancer selected from the group consisting of multiple myeloma, bone metastases from solid tumors, and prostate cancer. Osteoclast inhibitors useful in the practice of the methods described herein include, but are not limited to, pamidronate (Aredia). In accordance with the methods described herein, a compound or composition of the present invention is coadministered with an osteoclast inhibitor to treat cancer. In one embodiment, the cancer is osteolytic bone metastases of breast cancer, and one or more additional anti cancer agents are also coadministered with a compound of the present invention.

Cyclooxygenase inhibitors useful in the practice of the present treatment methods include, but are not limited to, celecoxib (Celebrex). In accordance with the methods described herein, a compound or composition of the present invention is coadministered with a cyclo-oxygenase inhibitor to treat cancer. In one embodiment, the cancer is colon cancer or a precancerous condition known as familial adenomatous polyposis.

Estrogen receptor modulators useful in the practice of the present treatment methods include, but are not limited to, tamoxifen (Nolvadex) and fulvestrant (Faslodex). In accordance with the methods described herein, a compound or composition of the present invention is coadministered with an estrogen receptor modulator to treat cancer. In one embodiment, the cancer is breast cancer or the treatment is administered to prevent the occurrence or reoccurrence of breast cancer.

Folate antagonists useful in the practice of the present treatment methods include, but are not limited to, methotrexate, pemetrexed (alimta), and trimetrexate. In accordance with the methods described herein, a compound or composition of the present invention is co-administered with a folate antagonist to treat cancer. In one embodiment, the cancer is osteosarcoma.

Methotrexate, an antifolate drug, has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. Methotrexate is administered as follows.

For choriocarcinoma, intramuscular injections of doses of 15 to 30 mg are administered daily for a five-day course, such courses repeated as needed with rest period of one or more weeks interposed between courses of therapy. For leukemias, twice weekly intramuscular injections are administered in doses of 30 mg/m$^2$. For mycosis fungoides, weekly intramuscular injections of doses of 50 mg or, alternatively, of 25 mg are administered twice weekly. In accordance with the methods described herein, a compound or composition of the present invention is coadministered with methotrexate administered at such doses (or at lower doses). Trimetrexate is another antifolate drug that can be coadministered with a compound of the present invention.

Inorganic arsenates useful in the practice of the present treatment methods include, but are not limited to, arsenic trioxide (Trisenox). In accordance with the methods described herein, a compound or composition of the present invention is coadministered with an inorganic arsenate to treat cancer. In one embodiment, the cancer is refractory acute promyelocytic leukemia (APL).

Microtubule inhibitors (as used herein, a microtubule inhibitor is any agent that interferes with the assembly or disassembly of microtubules) useful in the practice of the methods described herein include, but are not limited to, vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. In accordance with the methods described herein, a compound or composition of the present invention is coadministered with a microtubule inhibitor to treat cancer. In one embodiment, the cancer is ovarian cancer, breast cancer, non-small cell lung cancer, Kaposi's sarcoma, and metastatic cancer of breast or ovary origin. As one example, vincristine is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 mg/m$^2$ for children and 1.4 mg/m$^2$ for adults. In accordance with the methods described herein, a compound or composition of the present invention is coadministered with vincristine administered at such doses. In one embodiment, a compound or composition of the present invention is not administered prior to treatment with a microtubule inhibitor, such as a taxane, but rather, administration of a compound or composition of the present invention is administered simultaneously with or within a few days to a week after initiation of treatment with a microtubule inhibitor. In another embodiment, a compound or composition of the present invention is administered prior to treatment with a microtubule inhibitor.

Modifiers useful in the practice of the present treatment methods include, but are not limited to, leucovorin (Wellcovorin), which is used with other drugs such as 5-fluorouracil to treat colorectal cancer. In accordance with the methods described herein, a compound or composition of the present invention is coadministered with a modifier and another anti cancer agent to treat cancer. In one embodiment, the cancer is colon cancer. In one embodiment, the modifier is N-hydroxyurea. In another such embodiment, a compound or composition of the present invention is coadministered with nitric oxide or a nitric oxide precursor, such as an organic nitrite or a spermineNONOate, to treat cancer, as the latter compounds stimulate the uptake of glucose.

Nucleoside analogs useful in the practice of the present treatment methods include, but are not limited to, mercaptopurine (6-MP, Purinethol), fluorouracil (5-FU, Adrucil), thioguanine, (6-TG, Thioguanine), cytarabine (Cytosar-U, DepoCyt), floxuridine (FUDR), fludarabine (Fludara), azacytidine (Vidaza), pentostatin (Nipent), cladribine (Leustatin, 2-CdA), gemcitabine (Gemzar), and capecitabine (Xeloda). In accordance with the methods described herein, a compound or composition of the present invention is coadministered with a nucleoside analog to treat cancer. In one embodiment, the cancer is B-cell lymphocytic leukemia (CLL), hairy cell leukemia, adenocarcinoma of the pancreas, metastatic breast cancer, non-small cell lung cancer, or metastatic colorectal carcinoma. As one example, 5-fluorouracil is an antimetabolite nucleoside analog effective in the palliative management of carcinoma of the colon, rectum, breast, stomach, and pancreas in patients who are considered incurable by surgical therapy or by other means. 5-Fluorouracil is administered in initial therapy in doses of 12 mg/m$^2$ given intravenously once daily for 4 successive days with the daily dose not exceeding 800 mg. In accordance with the methods described herein, a compound or composition of the present invention is coadministered with 5-FU administered at such doses or with the drug form xeloda with correspondingly adjusted doses. As another example, 6-thioguanine, is a nucleoside analog effective in the therapy of acute non-lymphocytic leukemias. 6-Thioguanine is orally administered in doses of about 2 mg/kg of body weight per day. The total daily dose can be given at one time. If after four weeks of dosage at this level there is no improvement, the dosage can be cautiously increased to 3 mg/kg/day. In accordance with the methods described herein, a compound or composition of the present invention is coadministered with 6-TG administered at such doses (or at lower doses).

Retinoids useful in the practice of the present treatment methods include, but are not limited to, tretinoin, ATRA (Vesanoid), alitretinoin (Panretin), and bexarotene (Targretin). In accordance with the methods described herein, a compound or composition of the present invention is coadministered with a retinoid to treat cancer. In one embodiment, the cancer is a cancer selected from the group consisting of APL, Kaposi's sarcoma, and T-cell lymphoma.

Topoisomerase 1 inhibitors useful in the practice of the present treatment methods include, but are not limited to, topotecan (Hycamtin) and irinotecan (Camptostar). In accordance with the methods described herein, a compound or composition of the present invention is coadministered with a topoisomerase 1 inhibitor to treat cancer. In one embodiment, the cancer is metastatic carcinoma of the ovary, colon, or rectum, or small cell lung cancer. In certain embodiments of the treatment methods described herein, administration of a compound or composition of the present invention precedes and/or follows the administration of a topoisomerase 1 inhibitor, but is not administered concurrently therewith. In another embodiment, the other agent and the compound or composition of the present invention are administered concurrently.

Topoisomerase 2 inhibitors useful in the practice of the present treatment methods include, but are not limited to, etoposide, VP-16 (Vepesid), teniposide, VM-26 (Vumon), and etoposide phosphate (Etopophos). In accordance with the methods described herein, a compound or composition of the present invention is coadministered with a topoisomerase 2 inhibitor to treat cancer. In one embodiment, the cancer is a cancer selected from the group consisting of refractory testicular tumors, refractory acute lymphoblastic leukemia (ALL), and small cell lung cancer. In certain embodiments of the treatment methods described herein, administration of a compound or composition of the present invention precedes and/or follows the administration of a topoisomerase 2 inhibitor, but is not administered concurrently therewith. In another embodiment, the other agent and the compound or composition of the present invention are administered concurrently.

Tyrosine kinase inhibitors useful in the practice of the present treatment methods include, but are not limited to, imatinib (Gleevec). In accordance with the methods described herein, a compound or composition of the present invention is coadministered with a tyrosine kinase inhibitor to treat cancer. In one embodiment, the cancer is CML or a metastatic or unresectable malignant gastrointestinal stromal tumor. In another embodiment, the other agent is a multiple kinase inhibitor such as sorefenib. In another embodiment, the cancer treated is liver cancer.

In some embodiments of the present invention, a compound or composition of the present invention is administered to treat a hyperproliferative disease other than cancer selected from the group consisting of psoriasis, multiple sclerosis, rheumatoid arthritis, restenosis, and benign prostatic hyperplasia. In one embodiment, the hyperproliferative disease treated is psoriasis, a disease characterized by the cellular hyperproliferation of keratinocytes which builds up on the skin to form elevated, scaly lesions. In another embodiment, the hyperproliferative disease treated is multiple sclerosis, a disease characterized by progressive demyelination in the brain. In another embodiment, the hyperproliferative diseases treated is rheumatoid arthritis, a multisystem chronic, relapsing, inflammatory disease that can lead to destruction and ankylosis of joints affected. In another embodiment, the compounds or compositions of the present invention are administered to prevent a hyperproliferative disease resulting from cellular proliferation on a prosthesis implanted in a subject by coating the prosthesis with a composition containing a compound of the present invention or 14-nitro-20-acetoxycamptothecin. In another embodiment, the hyperproliferative disease treated is benign prostatic hyperplasia, a disease in which prostate epithelial cells grow abnormally and thereby block urine flow.

The various aspects and embodiments of the present invention having been described in summary and in detail, are illustrated and not limited by the examples below.

EXAMPLES

Example 1

Synthetic Methods

1.A. Synthesis of Compounds TH1317, TH1320, TH1332 and TH1338

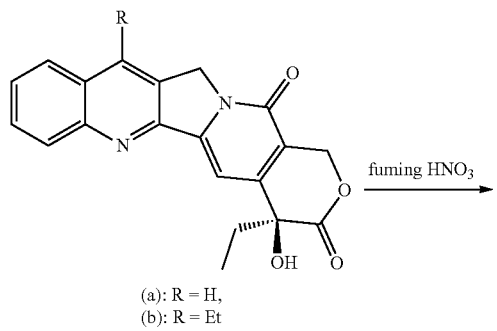

(a): R = H,
(b): R = Et

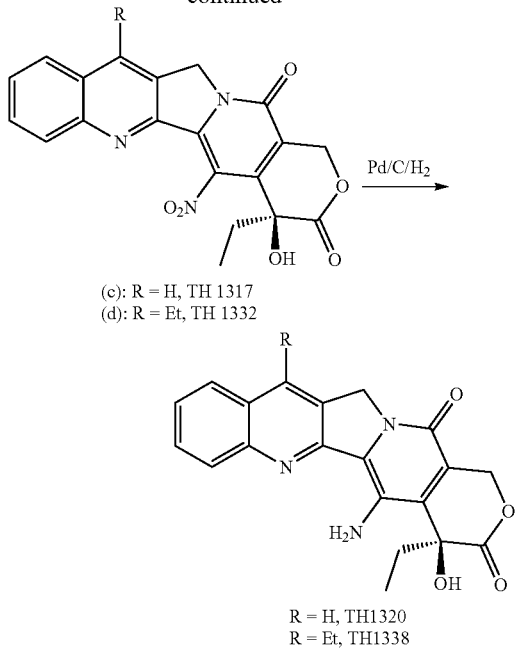

(c): R = H, TH 1317
(d): R = Et, TH 1332

R = H, TH1320
R = Et, TH1338

Camptothecin (Compound (a), 10 g, 28.7 mmole) was added to fuming nitric acid (90%, 100 mL) at room temperature. The mixture was stirred at room temperature overnight. The reaction mixture was poured into ice-water (500 mL) and stirred for 30 min. The precipitate was collected by filtration under reduced pressure and washed with water (200 mL), methanol (50 mL), and ethyl ether (Ether, 50 mL) to produce Compound (c) (TH1317) (7.0 g, yield: 62%). $^1$HNMR (DMSO-$d_6$) δ 8.76 (s, 1H), 8.16 (d, J=8.0 Hz, 1H), 8.05 (d, J=8.4 Hz, 1H), 7.88 (t, J=8.0 Hz, 1H), 7.76 (t, J=7.4 Hz, 1H), 6.74 (s, 1H), 5.46 (s, 2H), 5.31 (s, 2H), 2.00-2.16 (m, 2H), 0.93 (t, J=7.2 Hz, 1H). Compound (d) (TH1332) was obtained from Compound (b) via the nitration method above. The yield of Compound (d) was 2 g (65%). $^1$HNMR (DMSO-$d_6$) δ 8.31 (d, J=8.4 Hz, 1H), 8.04 (d, J=8.4 Hz, 1H), 7.87 (t, J=7.6 Hz, 1H), 7.78 (t, J=7.6 Hz, 1H), 6.72 (s, 1H), 5.47 (d, J=2.4 Hz, 2H), 5.35 (d, J=6.0 Hz, 2H), 3.24 (m, 2H), 2.00-2.16 (m, 2H), 1.30 (t, J=7.4 Hz, 3H), 0.93 (t, J=7.4 Hz, 3H).

1.0 g of 10% Pd/C was added to a suspension of 3.2 g of Compound (c) in MeOH/dichloromethane (DCM) (300 mL/100 mL). The air inside the reaction vessel was purged thrice with hydrogen, and the reaction mixture was stirred under hydrogen at room temperature overnight and then filtered. The filtrate was concentrated under reduced pressure, and the residue was dissolved in DCM and purified by column chromatography (DCM:MeOH=10:1(volume/volume or v/v)) to yield 1.4 g of TH1320. $^1$HNMR (CDCl$_3$) δ 8.19 (s, 1H), 8.10 (d, J=8.4 Hz, 1H), 7.82 (d, J=8.4 Hz, 1H), 7.75 (t, J=6.4 Hz, 1H), 7.57 (t, J=6.4 Hz, 1H), 6.51 (s, 2H), 5.77 (d, J=16.8 Hz, 1H), 5.25 (d, J=16.8 Hz, 1H), 5.24 (s, 2H), 4.35 (s, 1H), 2.12-2.24 (m, 1H), 1.90-2.00 (m, 1H), 1.08 (t, J=7.4 Hz, 3H).

TH1338 was obtained from Compound (d) via the reduction method above. The yield was 140 mg (62%). $^1$HNMR (CDCl$_3$) δ 8.11 (d, J=8.4 Hz, 1H), 8.04 (d, J=8.4 Hz, 1H), 7.73 (t, J=7.6 Hz, 1H), 7.58 (t, J=7.6 Hz, 1H), 6.48 (br, s, 2H), 5.78 (d, J=16.8 Hz, 1H), 5.26 (d, J=16.8 Hz, 1H), 5.22 (s, 2H), 3.13 (q, J=7.6 Hz, 1H), 2.12-2.24 (m, 1H), 1.90-2.00 (m, 1H), 1.38 (t, J=7.6 Hz, 3H), 1.08 (t, J=7.4 Hz, 3H).

1.B. Synthesis of Compound TH1339

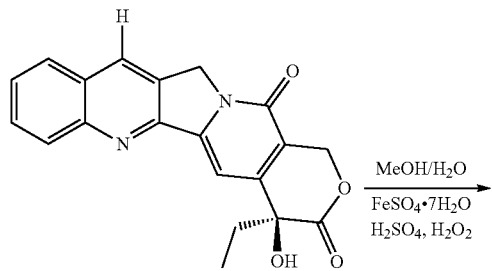

(a): R = H

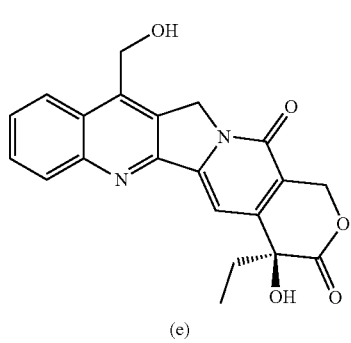

(e)

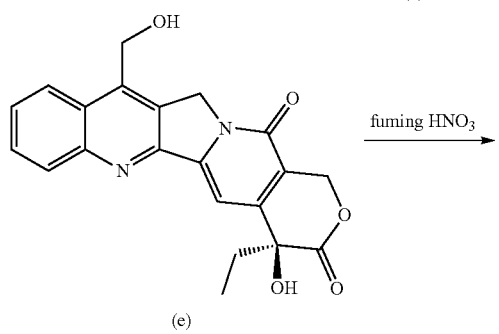

(e)

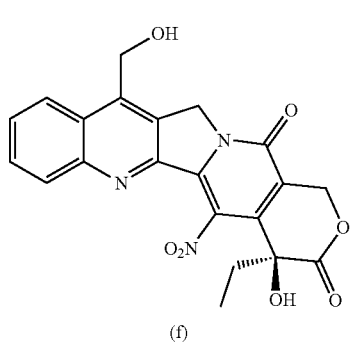

(f)

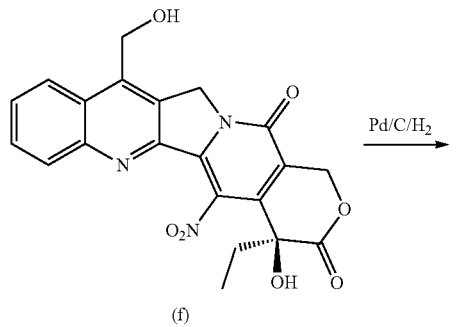

(f)

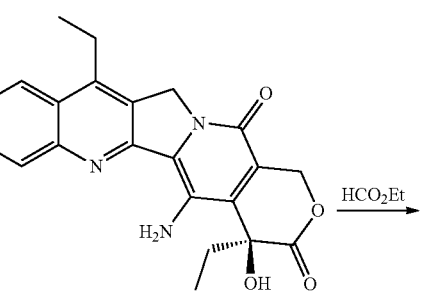

TH1339

Sulfuric acid (96%, 140 mL) was added slowly to a suspension of camptothecin (Compound (a), 15 g) in MeOH/H$_2$O (410 mL/330 mL) at 0° C. over 40 min. FeSO$_4$.7H$_2$O (13 g) was then added, and the reaction mixture was cooled to −10° C. H$_2$O$_2$ (40 mL) was slowly added to the reaction mixture. The stirred reaction mixture was allowed to warm to room temperature and was stirred overnight. The reaction mixture was filtered, and the solid was washed with water (300 mL), MeOH (50 mL) and Ether (50 mL) to yield 10.8 g of Compound (e). The filtrate was concentrated under reduced pressure. The residue was poured into ice-water (400 mL) to obtain an additional 1.6 g of Compound (e). The total yield of Compound (e) was 76%. $^1$HNMR (DMSO-d$_6$) δ 8.18 (m, 2H), 7.85 (t, J=7.2 Hz, 1H), 7.70 (t, J=7.6 Hz, 1H), 6.52 (s, 1H), 5.80 (s, br, 1H), 5.42 (d, J=3.6 Hz, 4H), 5.28, s, 2H), 1.87 (m, 2H), 0.88 (t, J=7.2 Hz, 1H).

Compound (f) was obtained from compound (e) via the nitration method employed for the synthesis of Compound (c) from Compound (a). The yield was 1 g (59%). $^1$HNMR (CDCl$_3$+MeOD-d3) δ 8.13 (d, J=8.8 1H), 7.90 (d, J=8.4 1H), 7.72 (t, J=7.6 Hz, 1H), 7.60 (t, J=7.6 Hz, 1H), 5.62 (d, J=16.4 Hz, 1H), 5.48 (s, 2H), 5.33 (s, 2H), 5.20 (d, J=16.8 Hz, 1H), 2.21 (m, 1H), 1.89 (m, 1H), 0.98 (t, J=7.4 Hz, 3H).

15 mg of 10% Pd/C were added to a suspension of 38 mg of Compound (f) in MeOH (30 mL). The air in the reaction vessel was purged thrice with hydrogen, and the reaction mixture was stirred under hydrogen at room temperature (rt) for 3 hrs and then filtered. The filtrate was concentrated under reduced pressure, and the residue was purified by silica gel column chromatography (DCM:MeOH=10:1(v/v)) to yield 10 mg of TH1339. $^1$HNMR (DMSO-d$_6$) δ 8.16 (d, J=8.4 Hz, 1H), 8.05 (d, J=8.4 Hz, 1H), 7.79 (t, J=7.2 Hz, 1H), 7.64 (t, J=7.2 Hz, 1H), 7.01 (s, 1H), 6.51 (br, s, 1H), 5.45 (d, J=17.2 Hz, 2H), 5.33 (d, J=17.2 Hz, 2H), 5.23 (s, 2H), 2.72 (s, 3H), 2.04-2.11 (m, 2H), 0.92 (t, J=7.4 Hz, 3H).

1.C. Synthesis of TH1408

TH1338

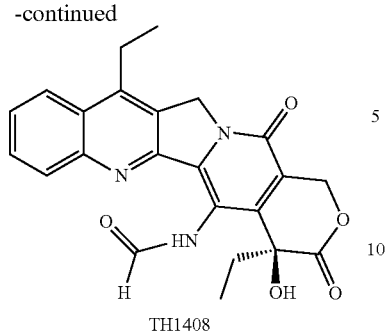

TH1408

A suspension of TH1338 (500 mg) in ethyl formate (25 mL) was heated under reflux for 24 hrs. The solvent was removed under reduced pressure. The residue was washed with diethyl ether to yield 420 mg of TH1408.

1.D. Synthesis of Compound TH1785

Compound TH1785 was synthesized as follows.

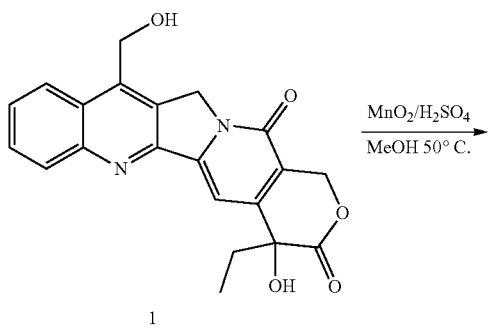

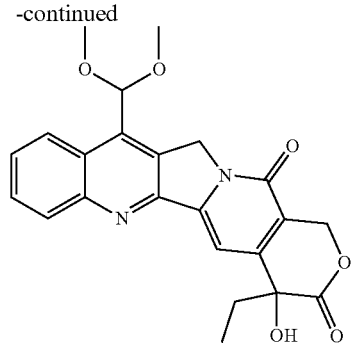

A mixture of compound 1 (1 g, 2.64 mmol), manganese dioxide (1.2 g, 5.2 mmol), 6 mL of 96% sulfuric acid in 40 mL of methanol was heated at 50° C. for overnight. After filtration, water (100 mL) was added to the solution and was extracted by DCM (70 mL×2). The organic phase was dried over $Na_2SO_4$ and concentrated under reduced pressure. The residue was chromatographed on silica gel (DCM: MeOH=95:5) to give 850 mg of compound 2. $^1$HNMR (CDCl$_3$) δ 8.31 (d, J=8.4 1H), 8.25 (d, J=8.4 1H), 7.83 (t, J=7.6 Hz, 1H), 7.68 (m, 2H), 6.27 (s, 1H), 5.77 (d, J=16.4 Hz, 1H), 5.50 (s, 2H), 5.32 (d, J=16.8 Hz, 1H), 3.42 (s, 3H), 3.41 (s, 3H), 1.89 (m, 2H), 1.05 (t, J=7.4 Hz, 3H).

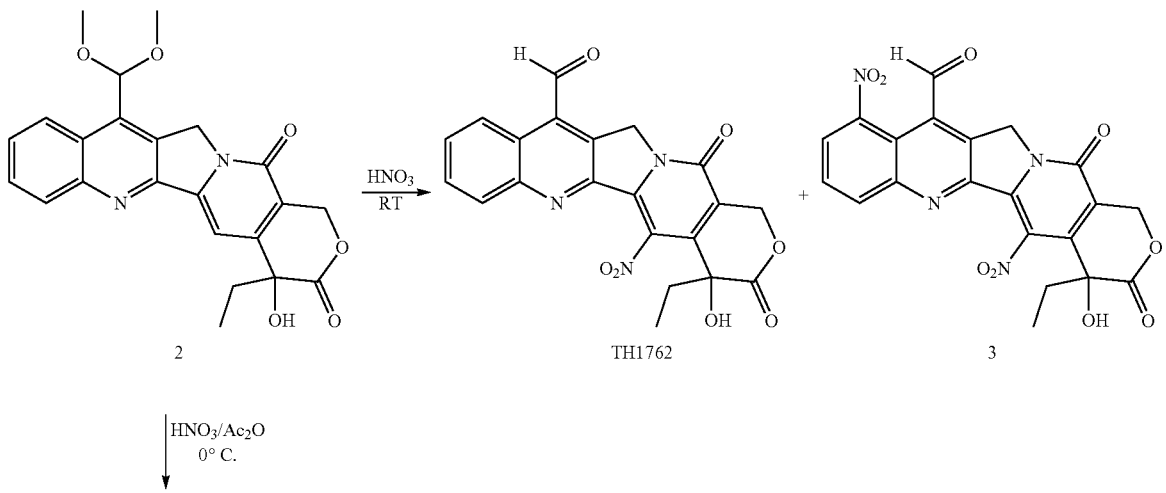

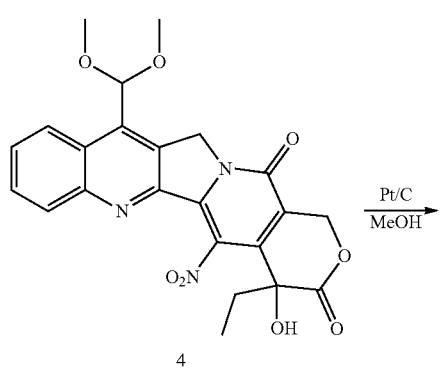
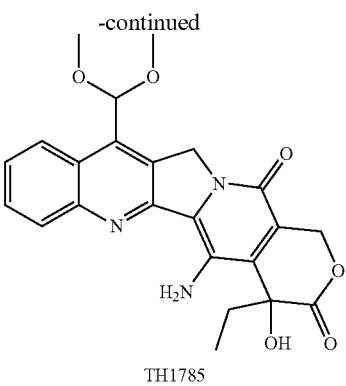

Compound 2 (1.16 g) was added to a solution of nitric acid (90%, 20 mL) at room temperature. The mixture was stirred at room temperature for overnight. The mixture was poured into ice-water (100 mL) and stirred for 30 min. The solution was extracted by DCM (150 mL×2). The organic phase was dried over $Na_2SO_4$ and concentrated under reduced pressure. The residue was chromatographed on silica gel (Hex: AcOEt=20:80) to give 250 mg of Compound 3 and 150 mg of TH1762. $^1$HNMR for TH1762 ($CDCl_3$) δ 11.24 (s, 1H), 8.75 (d, J=8.4 Hz, 1H), 8.43 (d, J=8.0 Hz, 1H), 7.958 (m, 2H), 5.79 (d, J=16.8 Hz, 1H), 5.64 (s, 2H), 5.30 (d, J=16.8 Hz, 1H), 3.97 (s, 1H), 2.35 (m, 1H), 1.95 (m, 1H), 1.08 (t, J=7.2 Hz, 1H).

A solution of nitric acid (90%, 0.9 mL) was slowly added to a suspension of compound 2 (3.0 g) in acetic anhydride (150 mL) at 0° C. for 3 hrs. The mixture was poured into ice-water (500 mL) and was extracted by AcOEt (150 mL×3). The organic phase was dried over $Na_2SO_4$ and concentrated under reduced pressure. The residue was chromatographed on silica gel (Hex: AcOEt=50:50) to give 1.2 g of compound 4. $^1$HNMR ($CDCl_3$) δ 8.27 (m, 2H), 7.82 (t, J=7.2 Hz, 1H), 7.71 (t, J=7.2 Hz, 1H), 6.26 (s, 1H), 5.77 (d, J=16.4 Hz, 1H), 5.50 (s, 2H), 5.28 (d, J=16.8 Hz, 1H), 3.98 (s, 1H), 3.40 (s, 3H), 3.38 (s, 3H), 2.33 (m, 1H), 1.94 (m, 1 h), 0.92 (t, J=7.4 Hz, 3H).

15 mg of 10% Pd/C was added to a suspension of 200 mg of compound 4 in MeOH (50 mL), purged with hydrogen thrice, stirred under hydrogen at rt for overnight and filtered. The filtrate was concentrated reduced pressure, the residue was purified by column to yield 60 mg of TH1785 (Hex: AcOEt=30:70 (V/V)). $^1$HNMR ($CDCl_3$) δ 8.21 (d, J=8.4 Hz, 1H), 8.10 (d, J=8.0 Hz, 1H), 7.74 (t, J=7.2 Hz, 1H), 7.58 (t, J=7.2 Hz, 1H), 6.57 (s, br, 2H), 6.21 (s, 1H), 5.80 (d, J=16.8 Hz, 1H), 5.44 (s, 2H), 5.26 (d, J=16.8 Hz, 1H), 4.32 (s, 1H), 3.43 (s, 3H), 3.35 (s, 3H), 2.15 (m, 1H), 1.95 (m, 1 h), 1.08 (t, J=7.6 Hz, 3H).

1.E. Synthesis of Compounds TH1522, TH1524, TH1762, TH1781, TH1784, and TH1786

The following reaction scheme was used to produce the compounds shown.

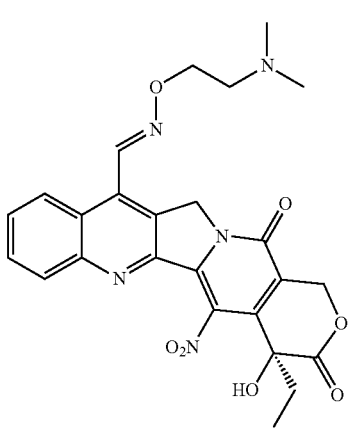
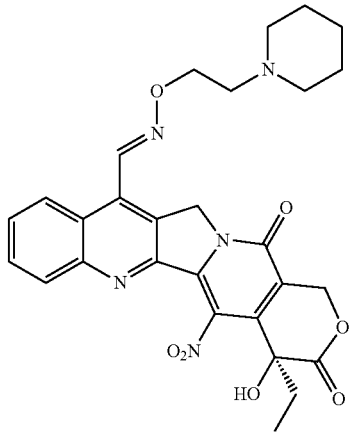

-continued

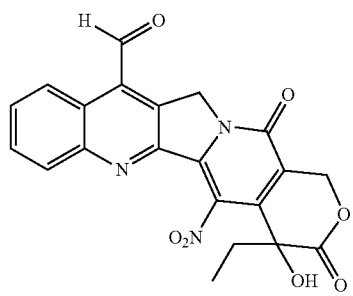
TH1762

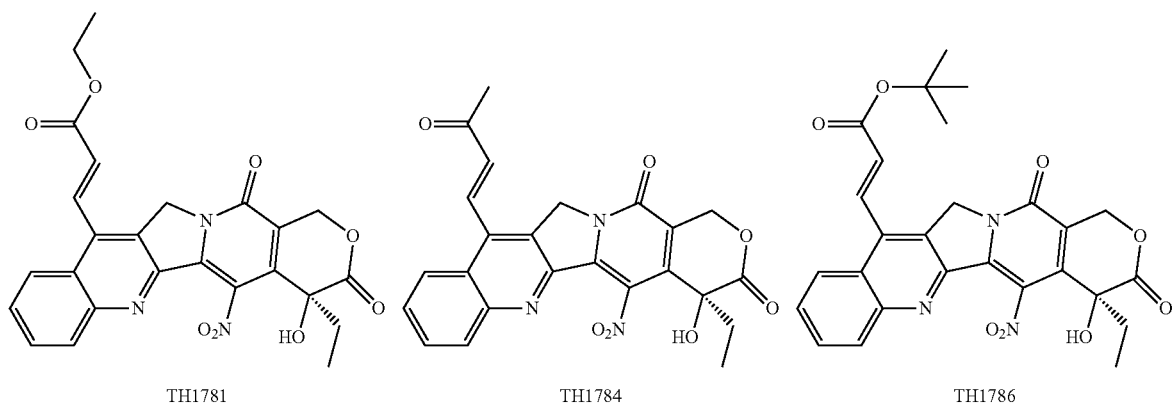
TH1781      TH1784      TH1786

To prepare compound TH1522, a solution of TH1762 (70 mg) and O-(2-dimethylaminoethyl)-hydroxylamine (23 mg) in 20 mL of acetic acid was heated at 80° C. overnight. After solvent was removed under reduced pressure, chromatography of the residue on silica gel gave 10 mg of TH1522. TH1524 (12 mg) was obtained via similar methodology with TH1522 from TH1762 (70 mg).

To prepare compounds TH1781, T H1784 and TH1786, a solution of TH1762 (160 mg), Ethoxycarbonylmethylene triphenylphosphorane (140 mg) in chloroform (50 mL) was refluxed for 4 hrs. After removing solvent under reduced pressure, chromatography of the residue on silica gel gave 50 mg of TH1781. $^1$HNMR (CDCl$_3$) δ 8.34 (d, J=16.4 Hz, 1H), 8.28 (d, J=8.4 Hz, 1H), 8.18 (d, J=8.4 Hz, 1H), 7.87 (t, J=7.6 Hz, 1H), 7.76 (t, J=7.6 Hz, 1H), 6.57 (d, J=16.4 Hz, 1H), 5.78 (d, J=16.8 Hz, 1H), 5.37 (s, 2H), 5.29 (d, J=16.8 Hz, 1H), 4.40 (m, 2H), 3.99 (s, 1H), 2.33 (m, 1H), 1.95 (m, 1H), 1.44 (t, J=7.6 Hz, 3H), 1.08 (t, J=7.6 Hz, 3H).

TH1784 (28 mg) was obtained via similar methodology with TH1781 from TH1762 (84 mg) and acetylmethylene triphenylphosphorane (65 mg). $^1$HNMR (CDCl$_3$) δ 8.29 (d, J=8.4 Hz, 1H), 8.17 (m, 2H), 7.87 (t, J=7.6 Hz, 1H), 7.76 (t, J=7.6 Hz, 1H), 6.83 (d, J=16.4 Hz, 1H), 5.76 (d, J=16.8 Hz, 1H), 5.36 (s, 2H), 5.29 (d, J=16.8 Hz, 1H), 4.40 (m, 2H), 3.99 (s, 1H), 2.55 (s, 3H), 2.33 (m, 1H), 1.95 (m, 1H), 1.08 (t, J=7.6 Hz, 3H).

TH1786 (30 mg) was obtained via similar methodology with TH1781 from TH1762 (84 mg) and tert-butoxycarbonylmethylene triphenylphosphorane (76 mg). $^1$HNMR (CDCl$_3$) δ 8.28 (d, J=8.4 Hz, 1H), 8.26 (d, J=16.4 Hz, 1H), 8.19 (d, J=8.4 Hz 1H), 7.87 (t, J=7.6 Hz, 1H), 7.75 (t, J=7.2 Hz, 1H), 6.49 (d, J=16.4 Hz, 1H), 5.78 (d, J=16.8 Hz, 1H), 5.37 (s, 2H), 5.30 (d, J=16.8 Hz, 1H), 3.99 (s, 1H), 2.33 (m, 1H), 1.95 (m, 1H), 1.63 (s, 9H), 1.08 (t, J=7.6 Hz, 3H).

1.F. Synthesis of Compounds TH1523 and TH1525

The following reaction scheme was used to produce the compounds shown.

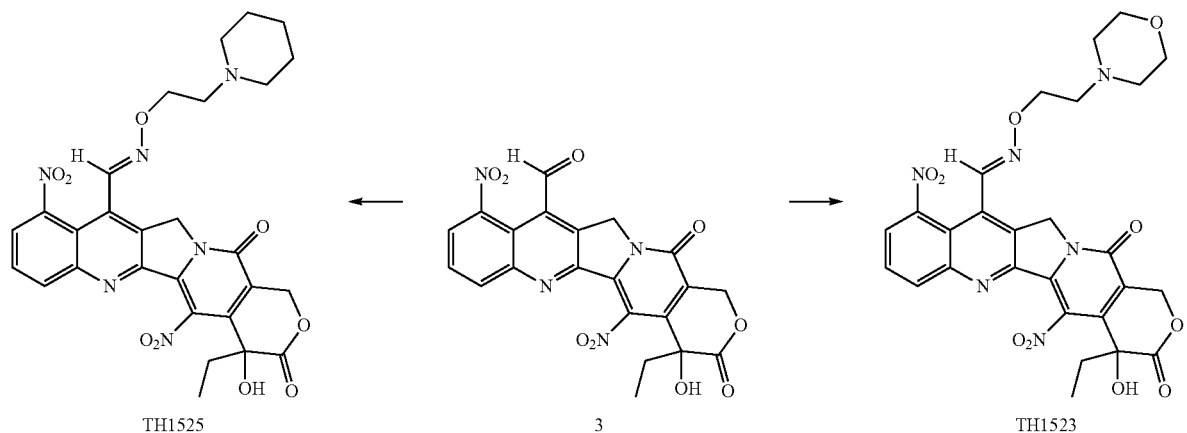

TH1523 (9 mg) was obtained via similar methodology used to produce TH1522 from compound 3 (70 mg) with O-(2-morpholin-4-yl-ethyl)-hydroxylamine (30 mg). (CDCl$_3$) δ 9.06 (s, 1H), 8.39 (d, J=8.8 Hz, 1H), 8.06 (d, J=7.2 Hz, 1H), 7.78 (t, J=8.0 Hz, 1H), 5.70 (d, J=16.8 Hz, 1H), 5.46 (d, J=3.6 Hz, 2H), 5.25 (d, J=16.8 Hz, 1H), 4.62 (t, J=5.6 Hz, 2H), 3.79 (t, J=4.4 Hz, 4H), 2.88 (t, J=5.6 Hz, 2H), 2.63 (s, 4H), 2.26 (m, 1H), 1.91 (m, 1H), 1.03 (t, J=7.6 Hz, 3H).

TH1525 (12 mg) was obtained via similar methodology used to produce TH1522 from compound 3 (70 mg) with O-(2-piperidin-1-yl-ethyl)-hydroxylamine (30 mg).

1.G. Synthesis of Compounds TH1787 and TH1789

The following reaction scheme was used to produce the compounds shown.

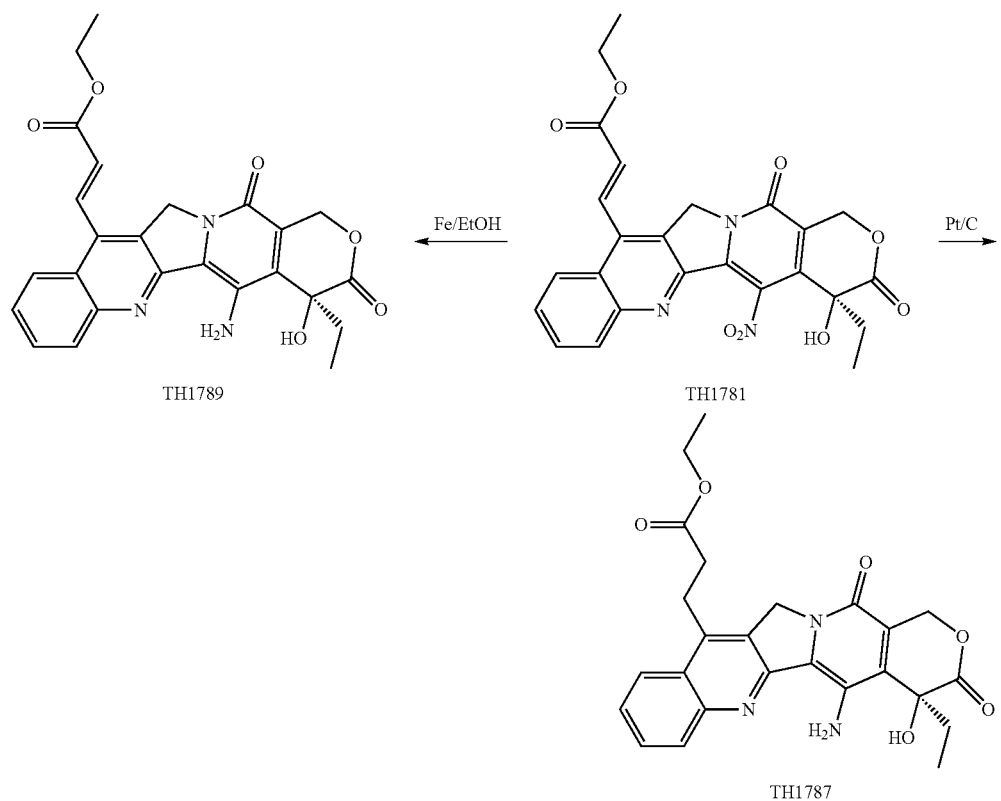

To prepare TH1787, 10 mg of 10% Pd/C were added to a solution of 20 mg of TH1781 in MeOH (10 mL), purged with hydrogen thrice, stirred under hydrogen at rt for overnight and filtered. The filtrate was concentrated reduced pressure, the residue was purified by column to yield 10 mg of TH1787 (DCM:MeOH=90:10 (V/V)). (CDCl₃) δ 8.11 (d, J=8.4 Hz, 1H), 8.00 (d, J=8.4 Hz, 1H), 7.74 (t, J=7.6 Hz, 1H), 7.59 (t, J=7.6 Hz, 1H), 6.48 (d, br, 2H), 5.78 (d, J=16.8 Hz, 1H), 5.31 (s, 2H), 5.26 (d, J=16.8 Hz, 1H), 4.32 (s, 1H), 4.12 (q, J=7.6 Hz, 2H), 3.42 (t, J=7.6 Hz, 2H), 2.76 (t, J=7.6 Hz, 2H), 2.15 (m, 1H), 1.95 (m, 1H), 1.22 (t, J=7.2 Hz, 3H), 1.07 (t, J=7.6 Hz, 3H).

To prepare TH1789, 10 mg of iron were added to a solution of 20 mg of TH1781 in EtOH (10 mL) following addition of 1 drop of HCl. The reaction mixture was heated at 80° C. for two hrs and filtered. The filtrate was concentrated reduced pressure, the residue was purified by column to yield 10 mg of TH1789 (DCM:MeOH=95:5 (V/V)). ¹HNMR (CDCl₃) δ 8.32 (d, J=16.4 Hz, 1H), 8.13 (m, 2H), 7.79 (t, J=7.6 Hz, 1H), 7.63 (t, J=7.6 Hz, 1H), 6.55 (m, 3H), 5.80 (d, J=16.8 Hz, 1H), 5.33 (s, 2H), 5.28 (d, J=16.8 Hz, 1H), 4.38 (q, J=7.2 Hz, 2H), 4.33 (s, 1H), 2.18 (m, 1H), 1.95 (m, 1H), 1.43 (t, J=7.2 Hz, 3H), 1.09 (t, J=7.6 Hz, 3H).

1.H. Synthesis of Compound TH1790

The following reaction scheme was used to produce TH1790.

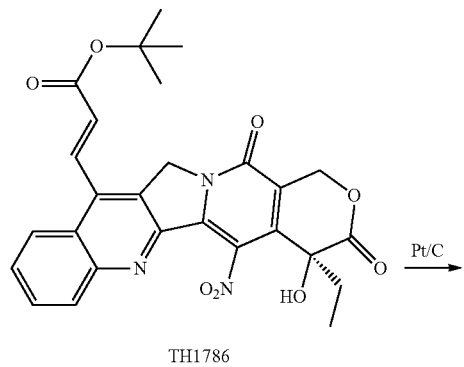

TH1786

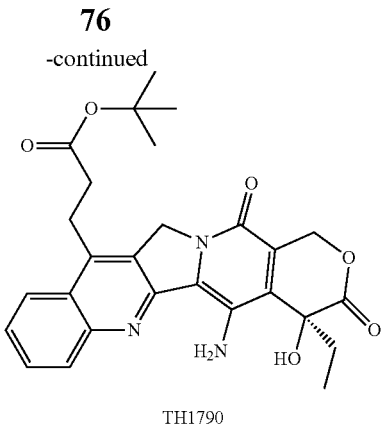

TH1790

To prepare TH1790, 10 mg of 10% Pd/C was added to a solution of 20 mg of TH1786 in MeOH (10 mL), purged with hydrogen thrice, stirred under hydrogen at rt for 2 hrs and filtered. The filtrate was concentrated reduced pressure, the residue was purified by column to yield 10 mg of TH1790 (Hexane:AcOEt=50:50 (v/v). (CDCl₃) δ 8.13 (d, J=8.0 Hz, 1H), 8.03 (d, J=8.0 Hz, 1H), 7.75 (t, J=7.6 Hz, 1H), 7.60 (t, J=7.6 Hz, 1H), 6.50 (s, 2H), 5.81 (d, J=17.2 Hz, 1H), 5.33 (s, 2H), 5.28 (d, J=16.8 Hz, 1H), 4.29 (s, 1H), 3.40 (t, J=7.6 Hz, 2H), 2.68 (t, J=7.6 Hz, 2H), 2.15 (m, 1H), 1.95 (m, 1H), 1.43 (s, 9H), 1.09 (t, J=7.6 Hz, 3H).

1.I. Synthesis of Compounds TH1598, TH1599, and TH1605

The following reaction scheme was used to produce the compounds shown.

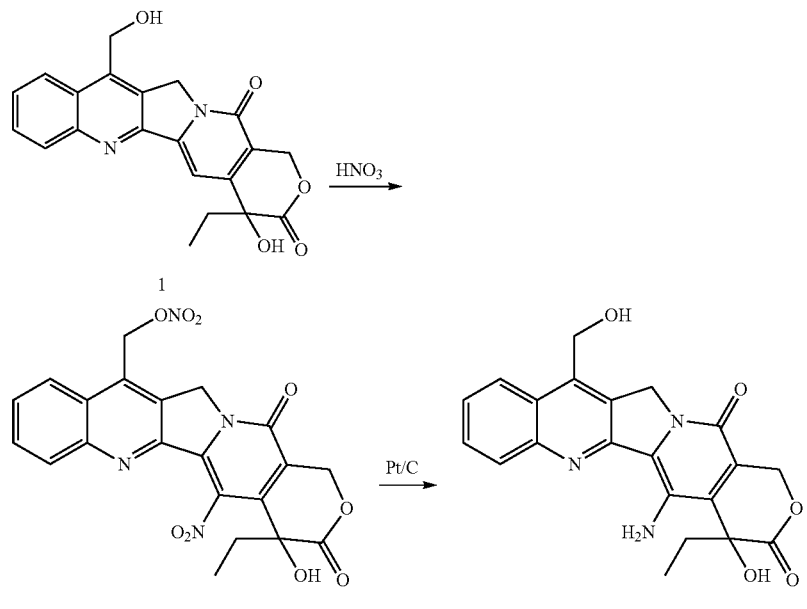

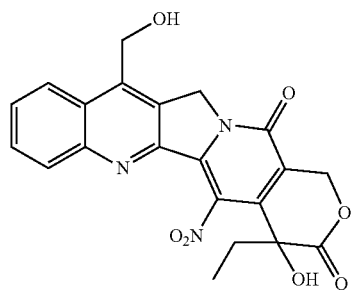

TH1605

To prepare TH1598, compound 1 (1.0 g) was added to a solution of nitric acid (90%, 10 mL) at room temperature. The mixture was stirred at room temperature overnight. The mixture was poured into ice-water (300 mL) and stirred for 30 min. The filtrate was collected under reduced pressure and washed with water (200 mL), methanol (20 mL), ethyl ether (20 mL). TH1598 was obtained (0.7 g). $^1$HNMR (DMSO-$d_6$) δ 8.40 (d, J=8.0 Hz, 1H), 8.08 (d, J=8.0 Hz, 1H), 7.91 (t, J=7.6 Hz, 1H), 7.84 (t, J=7.6 Hz, 1H), 6.71 (s, 1H), 6.26 (s, 2H), 5.45 (s, 4H), 2.05 (m, 2H), 0.91 (t, J=7.6 Hz, 3H).

To prepare TH1599, 50 mg of 10% Pd/C was added to a solution of 500 mg of TH1598 in MeOH/DCM: (200 mL/50 mL), purged with hydrogen thrice, stirred under hydrogen at rt overnight and filtered. The filtrate was concentrated reduced pressure, the residue was purified by column to yield 90 mg of TH1599 (DCM:MeOH=80:20 (v/v)). $^1$HNMR (CDCl$_3$+MeOD-$d_3$) δ 8.03 (d, J=8.4 Hz, 1H), 7.91 (d, J=8.0 Hz, 1H), 7.67 (t, J=7.6 Hz, 1H), 7.51 (t, J=7.6 Hz, 1H), 5.63 (d, J=16.8 Hz, 1H), 5.39 (s, 2H), 5.26 (s, 2H), 5.18 (d, J=16.8 Hz, 1H), 2.12 (m, 1H), 1.95 (m, 1H), 0.98 (t, J=7.6 Hz, 3H).

To prepare TH1605, a suspension of TH1598 (1.05 g) in HOAC/H$_2$O (80 mL/20 mL) was heated at 80° C. overnight. After removing solvents, the residue was recrystallized from MeOH/DCM to give 800 mg of TH1605. $^1$HNMR (CDCl$_3$+MeOD-$d_3$) δ 8.13 (d, J=8.8 Hz, 1H), 7.90 (d, J=8.4 Hz, 1H), 7.72 (t, J=7.6 Hz, 1H), 7.60 (t, J=7.6 Hz, 1H), 5.62 (d, J=16.8 Hz, 1H), 5.48 (s, 2H), 5.33 (s, 2H), 5.20 (d, J=16.8 Hz, 1H), 2.22 (m, 1H), 1.95 (m, 1H), 0.98 (t, J=7.6 Hz, 3H).

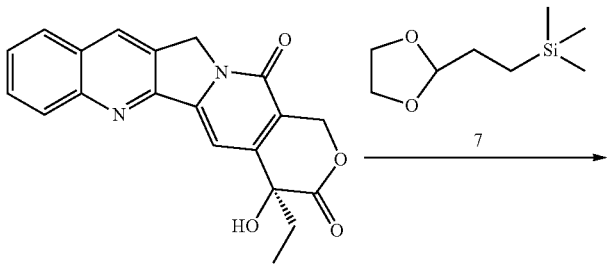

6

1.J. Synthesis of Compound TH1636

The following reaction scheme was used to produce TH1636.

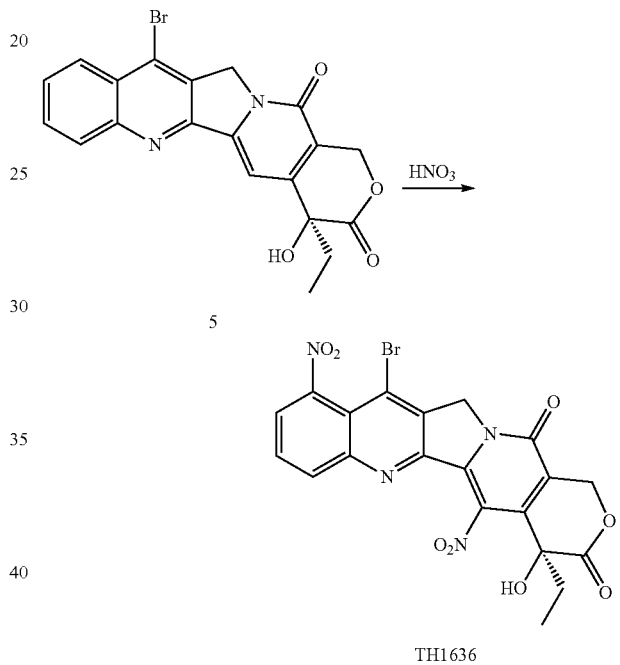

TH1636

To prepare compound TH1636, compound 5 (0.2 g) was added to a solution of nitric acid (90%, 3 mL) at room temperature. The mixture was stirred overnight at room temperature. The mixture was poured into ice-water (100 mL). The precipitated solid was collected by filtration under reduced pressure, and washed with water (10 mL), methanol (10 mL), and ethyl ether (10 mL). Only TH1636 was obtained (0.12 g).

1.K. Synthesis of Compounds TH1626, TH1627, TH1628, and TH1631

The following reaction scheme was used to produce the compounds shown.

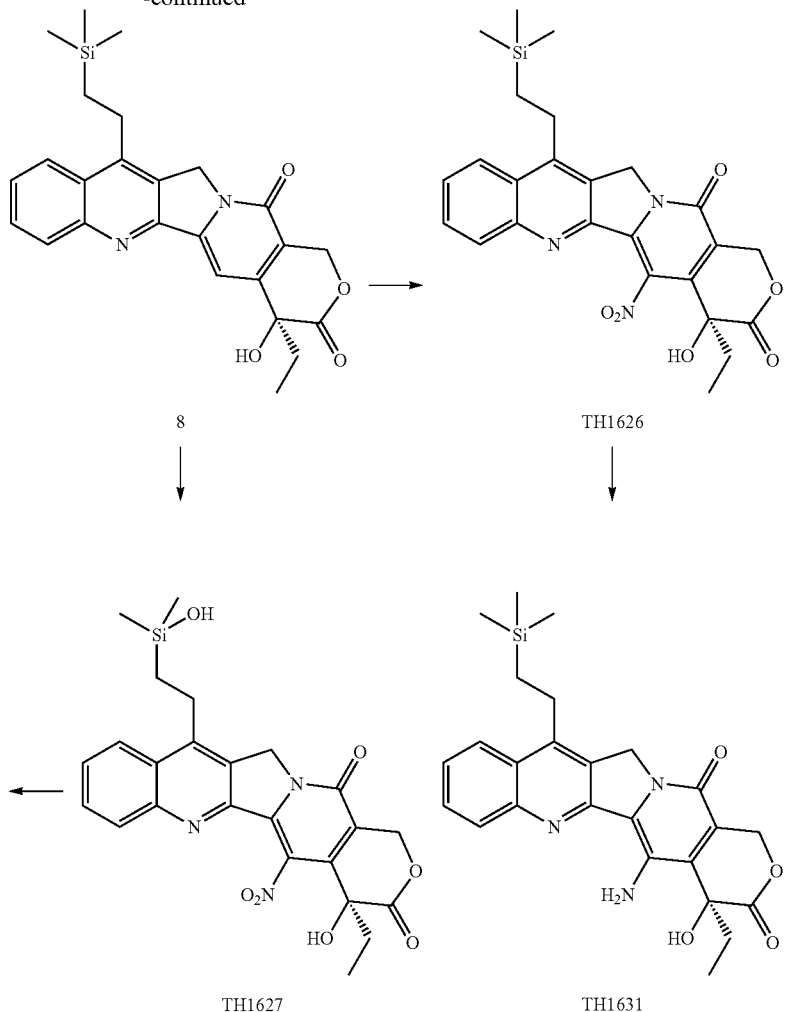

Compound 8 was first prepared as follows. Ferrous sulfate heptahydrate (FeSO$_4$.7H$_2$O 1.3 g) was added to a solution of compound 6 (1.3 g) in 78 mL of 30% sulfuric acid at 0° C. After a solution of compound 7 in 26 mL of tert-Butanol was added, 1.5 mL of 30% hydrogen peroxide was slowly added. The mixture was stirred and allowed to rise overnight from 0° C. to room temperature, poured into ice-water (500 mL), and extracted with DCM (70 mL×3). The organic phase was dried over Na$_2$SO$_4$ and concentrated under reduced pressure. The residue was chromatographed on silica gel (Hexane:AcOEt=50:50) to give 1.0 g of Compound 8. (CDCl$_3$) δ 8.25 (d, J=8.4 Hz, 1H), 8.06 (d, J=8.4 Hz, 1H), 7.82 (t, J=7.6 Hz, 1H), 7.68 (m, 2H), 5.77 (d, J=16.0 Hz, 1H), 5.32 (d, J=16.0 Hz, 1H), 5.26 (s, 2H), 3.12 (m, 2H), 1.91 (m, 2H), 1.05 (t, J=7.6 Hz, 3H), 0.94 (m, 2H), 0.19 (s, 9H).

TH1626 and TH1627 were prepared from Compound 8 as follows. Compound 8 (450 mg) was added to 10 mL of 90% nitric acid at room temperature overnight. The mixture was poured into ice-water (300 mL). DCM (50 mL×3) extracted. The organic phase was dried over Na$_2$SO$_4$ and concentrated under reduced pressure. The residue was chromatographed on silica gel (Hex: AcOEt=50:50) to give 50 mg of TH1626 and 80 mg of TH1627. $^1$HNMR for TH1626 (CDCl$_3$) δ 8.23 (d, J=8.4 Hz, 1H), 8.00 (d, J=8.4 Hz, 1H), 7.79 (t, J=7.6 Hz, 1H), 7.69 (t, J=7.6 Hz, 1H), 5.76 (d, J=16.8 Hz, 1H), 5.28 (d, J=16.8 Hz, 1H), 5.22 (s, 2H), 4.00 (s, 1H), 3.09 (m, 2H), 2.35 (m, 1H), 1.95 (m, 1H), 1.07 (t, J=7.6 Hz, 3H), 0.89 (m, 2H), 0.19 (s, 6H). $^1$HNMR for TH1627 (CDCl$_3$) δ 8.16 (d, J=8.4 Hz, 1H), 8.02 (d, J=8.4 Hz, 1H), 7.75 (t, J=7.6 Hz, 1H), 7.64 (t, J=7.6 Hz, 1H), 5.79 (d, J=16.8 Hz, 1H), 5.24 (d, J=16.8 Hz, 1H), 5.22 (s, 2H), 4.11 (s, 1H), 3.19 (m, 2H), 2.30 (m, 1H), 1.95 (m, 1H), 1.05 (m, 5H), 0.27 (s, 6H).

To prepare TH1628, 10 mg of 10% Pd/C were added to a solution of 40 mg of TH1627 in MeOH (5 mL), purged with hydrogen thrice, stirred under hydrogen at rt for overnight and filtered. The filtrate was concentrated reduced pressure, the residue was purified by column to yield 25 mg of TH1628 (DCM:MeOH=90:10 (V/V)). (CDCl$_3$) δ 8.04 (d, J=8.4 Hz, 1H), 7.91 (d, J=8.0 Hz, 1H), 7.68 (t, J=7.6 Hz, 1H), 7.49 (t, J=7.6 Hz, 1H), 6.04 (s, br, 2H), 5.65 (d, J=16.8 Hz, 1H), 5.18 (d, J=16.8 Hz, 1H), 5.14 (s, 2H), 4.50 (s, br, 1H), 2.98 (m, 2H), 2.13 (m, 1H), 1.91 (m, 1H), 1.04 (t, J=7.2 Hz, 3H), 0.98 (m, 2H), 0.26 (d, J=6.4 Hz, 6H).

TH1631 (10 mg) was obtained via a similar method as used for making TH1628 from TH1626. (CDCl$_3$) δ 8.10 (d, J=8.4 Hz, 1H), 7.95 (d, J=8.4 Hz, 1H), 7.72 (t, J=7.6 Hz, 1H), 7.57 (t, J=7.6 Hz, 1H), 6.48 (s, br, 2H), 5.78 (d, J=16.8 Hz, 1H), 5.26 (d, J=16.0 Hz, 1H), 5.19 (s, 2H), 3.02 (m, 2H), 2.15 (m, 1H), 1.91 (m, 1H), 1.07 (t, J=7.6 Hz, 3H), 0.84 (m, 2H), 0.17 (s, 9H).

1.L. Synthesis of Compounds TH1643, TH1644, TH1650, and TH1651

The following reaction scheme was used to produce the compounds shown.

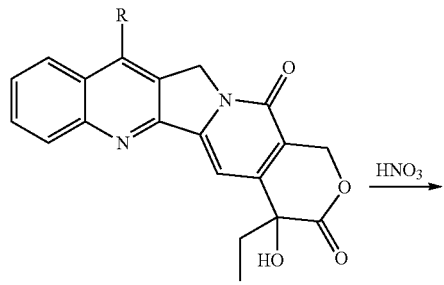

9 R = n-Pr
10 R = neopentyl

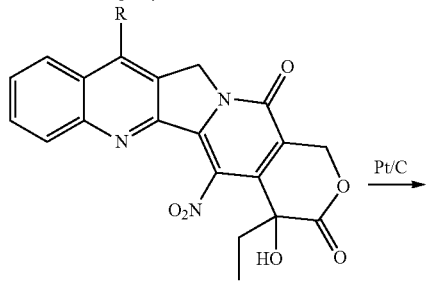

TH1650 R = n-Pr
TH1644 R = neopentyl

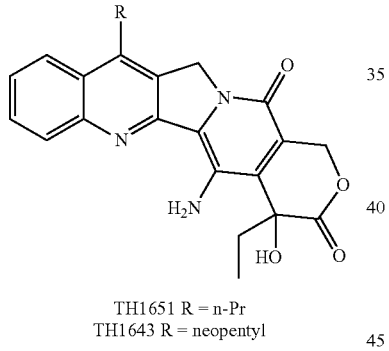

TH1651 R = n-Pr
TH1643 R = neopentyl

To prepare TH1644, Compound 10 (50 mg) was added to a solution of nitric acid (90%, 1.5 mL) at room temperature. The mixture was stirred at room temperature for 3 hrs. The mixture was poured into ice-water (50 mL). The filtrate was collected under reduced pressure and washed with water (10 mL), methanol (5 mL), ethyl ether (5 mL). TH1644 was obtained (20 mg). (CDCl$_3$) δ 8.20 (d, J=8.4 Hz, 1H), 8.14 (d, J=8.8 Hz, 1H), 7.77 (t, J=7.6 Hz, 1H), 7.64 (t, J=7.6 Hz, 1H), 5.74 (d, J=16.8 Hz, 1H), 5.27 (d, J=16.8 Hz, 1H), 5.27 (s, 2H), 4.06 (s, 1H), 3.13 (m, 2H), 2.03 (m, 1H), 1.95 (m, 1H), 1.07 (m, 12H).

TH1650 (450 mg) was obtained via similar methodology used to produce TH1644 from Compound 9 (1.1 g) with 15 mL of 90% nitric acid. $^1$HNMR (DMSO-d$_6$) δ 8.30 (d, 1H), 8.02 (d, 1H), 7.85 (t, 1H), 7.76 (t, 1H), 6.71 (s, 1H), 5.45 (d, 2H), 5.32 (d, 2H), 3.20 (m, 2H), 2.07 (m, 2H), 1.71 (m, 2H), 1.02 (t, 3H), 0.90 (t, 3H).

To prepare TH1643, 20 mg of 10% Pd/C were added to a solution of 15 mg of TH1644 in MeOH (7 mL), purged with hydrogen thrice, stirred under hydrogen at room temperature (rt) for 3 hrs and filtered. The filtrate was concentrated reduced pressure, the residue was purified by column to yield 10 mg of TH1643 (Hex:AcOEt=50:50 (v/v)). (CDCl$_3$) δ 8.08 (m, 2H), 7.71 (t, J=7.6 Hz, 1H), 7.53 (t, J=7.6 Hz, 1H), 6.51 (s, br, 2H), 5.76 (d, J=17.2 Hz, 1H), 5.23 (m, 3H), 4.40 (s, 1H), 3.05 (m, 2H), 2.17 (m, 1H), 1.95 (m, 1H), 1.05 (m, 12H).

TH1651 (200 mg) was obtained by similar methodology used to produce TH1543 from TH1650 (300 mg). $^1$HNMR (CDCl$_3$) δ 8.11 (d, 1H), 8.04 (d, 1H), 7.73 (t, 1H), 7.58 (t, 1H), 5.79 (d, 1H), 5.27 (d, 2H), 5.23 (s, 2H), 3.09 (m, 2H), 2.17 (m, 1H), 1.96 (m, 1H), 1.81 (m, 2H), 1.08 (t, 6H).

1.M. Synthesis of Compounds TH1766, TH1767, TH1768, TH1769, TH1770, TH1771, TH1775, TH1776, TH1777, TH1778, TH1780, TH1783, TH1791, TH1793, TH1794, TH1796, TH1797, TH1798, and TH1799

The following reaction scheme was used to produce intermediate compound D, which was used to produce various other compounds of the invention.

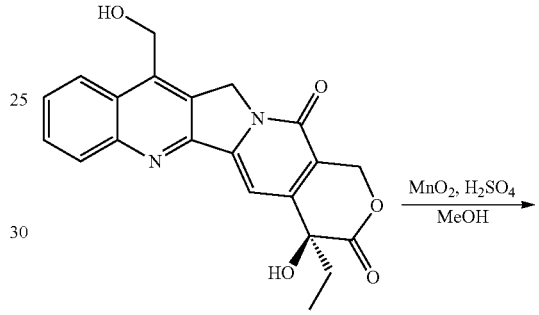

A

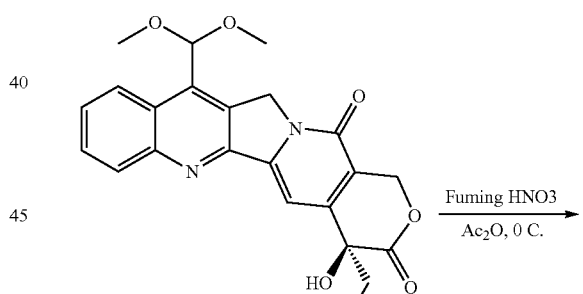

B

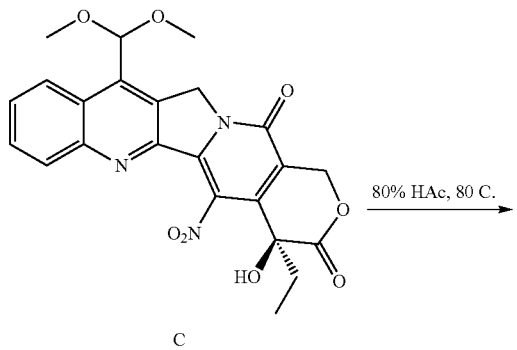

C

-continued

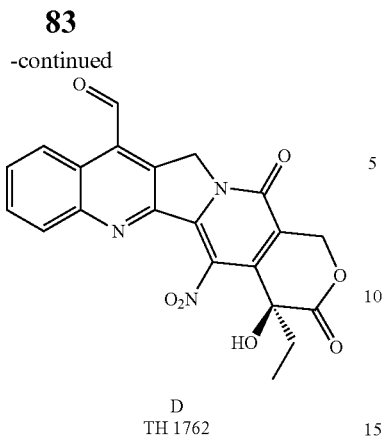

D
TH 1762

-continued

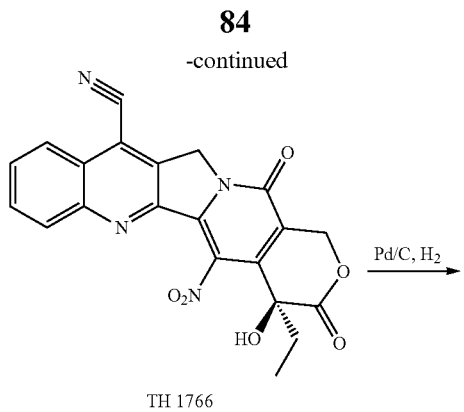

TH 1766

Compound B was prepared as follows. A 500 mL round bottom flask was charged with compound A (4.0 g, 10.56 mmol), MeOH (150 mL), sulfuric acid (96%, 20 mL) and manganese dioxide (4.8 g, 55.17 mmol). The mixture was stirred at 50° C. overnight and then filtered through filter paper. The filtrate was applied on a rotovap to remove MeOH, and the residue was poured into ice-water (300 mL). The resultant yellow precipitate was filtered and dried in the air to afford compound B (3.0 g, 67%).

Compound C was then prepared as follows. A 500 mL round bottom flask was charged with compound B (3.0 g, 7.1 mmol) and acetic anhydride (120 mL). The mixture was cooled in an ice-water bath and then fuming nitric acid (1.5 mL) was added slowly. The mixture was stirred at the same temperature for 0.5 h before it was poured into ice-water (300 mL) and then extracted with EtOAc (3×100 mL). The combined organic layers were washed with 1 M $Na_2CO_3$, brine and dried over $Na_2SO_4$. The solution was filtered, concentrated under reduced pressure, and then purified via flash chromatography (40 g of silica gel column, 0-100% EtOAc/Hexane eluting) to afford compound C as a yellow solid (1.5 g, 45%)

TH1762 (compound D) was prepared as follows. A 250 mL round bottom flask was charged with compound C (1.5 g, 3.2 mmol) and acetic acid (80% aqueous solution, 50 mL). The mixture was stirred at 80 C for 4 h and concentrated under reduced pressure. The residue was purified via flash chromatography (40 g of silica gel, 0-100% EtOAc/Hexane eluting) to afford compound D as a yellow solid (1.0 g, 74%).

TH1766 was prepared from compound D (TH1762), and TH1769 was prepared from TH1766 using the following reaction scheme.

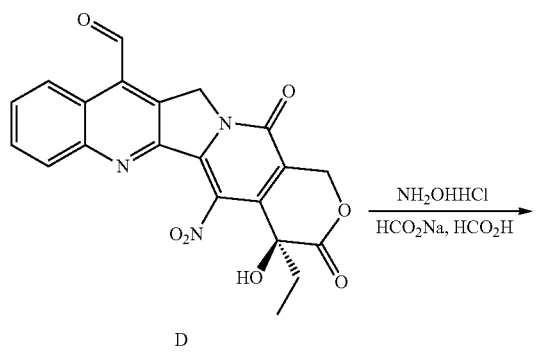

D

NH$_2$OHHCl
HCO$_2$Na, HCO$_2$H

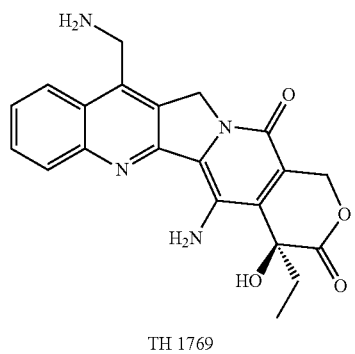

TH 1769

Compound TH1766 was prepared as follows. A 25 mL round bottom flask was charged with compound D (TH1762) (104 mg, 0.25 mmol), formic acid (8 mL), hydroxylamine hydrochloride (45 mg, 0.64 mmol) and sodium formate (226 mg, 3.32 mmol). The mixture was refluxed overnight and then the solvent was removed under reduced pressure. The residue was purified via flash chromatography (12 g of silica gel, 0-100% EtOAc/Hexane eluting) to afford TH1766 as a yellow solid (52 mg, 50%). $^1$H NMR (400 MHz, CDCl$_3$) δ: 8.40 (d, J=8.0 Hz, 1H), 8.31 (d, J=8.0 Hz, 1H), 8.01-7.94 (m, 2H), 5.78 (d, J=16.8 Hz, 1H), 5.51 (s, 2H), 5.32 (d, J=16.8 Hz, 1H), 1.97-1.94 (m, 2H), 1.08 (t, J=7.6 Hz, 3H).

Compound TH1769 was prepared as follows. A 25 mL round bottom flask was charged with TH1766 (40 mg, 0.096 mmol), EtOAc (10 mL) and 10% Pd/C (20 mg). The reaction vessel was purged with hydrogen three times and then the mixture was stirred under hydrogen (balloon) at room temperature overnight. The catalyst was filtered and the filtrate was concentrated under reduced pressure. The residue was purified via flash chromatography (12 g of silica gel, 0-10% MeOH/DCM eluting) to afford TH1769 as a yellow solid (8 mg, 21%).

Compounds TH1767, TH1768, TH1770, and TH1771 were prepared from TH1762 (compound D in the scheme) using the following reaction scheme.

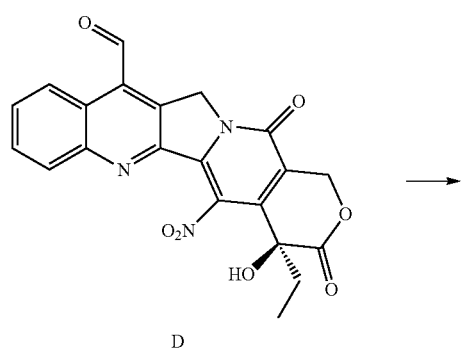

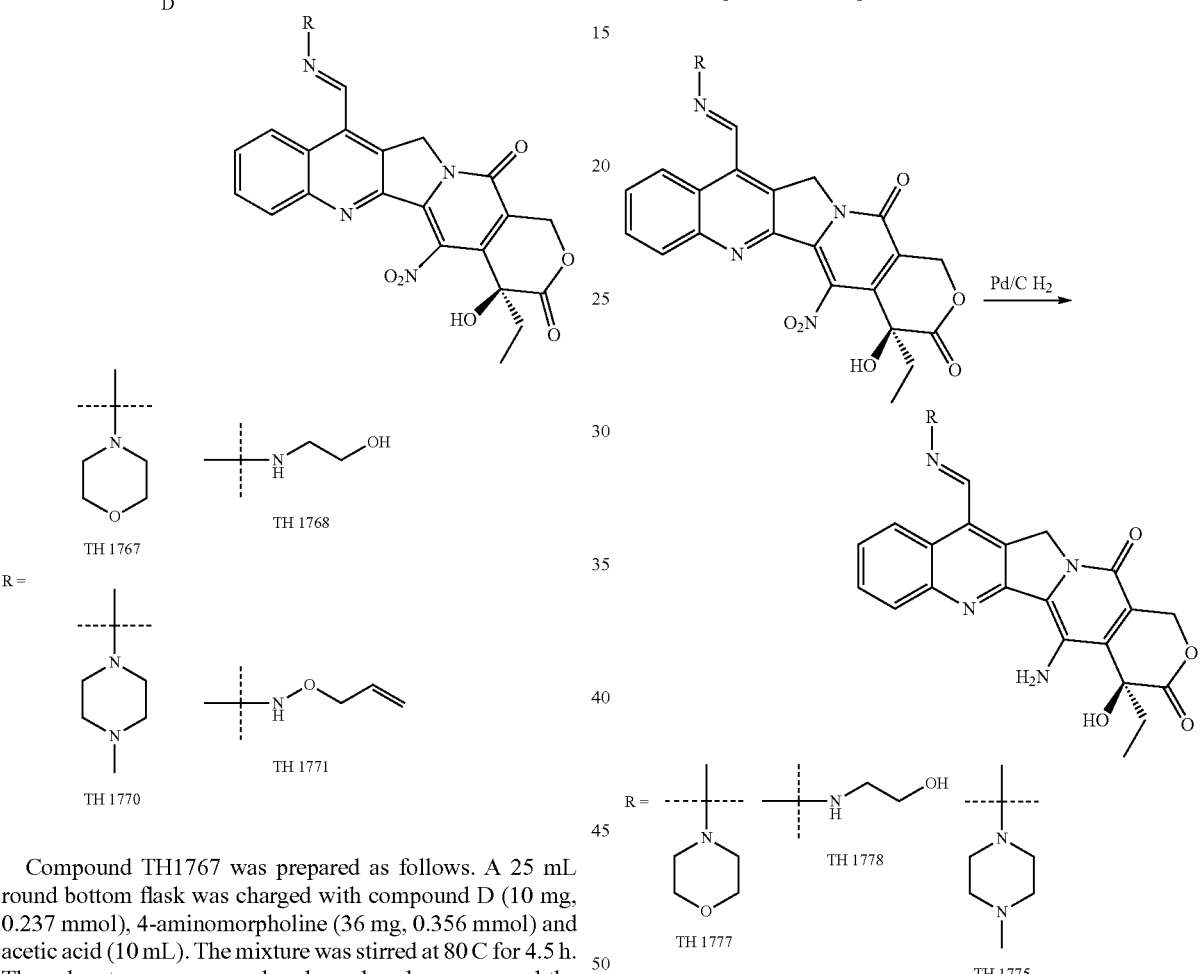

Compound TH1767 was prepared as follows. A 25 mL round bottom flask was charged with compound D (10 mg, 0.237 mmol), 4-aminomorpholine (36 mg, 0.356 mmol) and acetic acid (10 mL). The mixture was stirred at 80 C for 4.5 h. The solvents were removed under reduced pressure and the residue was purified via flash chromatography (12 g of silica gel, 0-100% EtOAc/Hexane eluting) to afford TH1767 as a yellow solid (41 mg, 34%). $^1$H NMR (400 MHz, CDCl$_3$) δ: 8.31 (s, 1H), 8.22 (d, J=8.4 Hz, 2H), 7.86 (t, J=7.2 Hz, 1H), 7.65 (t, J=7.2 Hz, 1H), 5.76 (d, J=16.4 Hz, 1H), 5.44 (s, 2H), 5.28 (d, J=16.4 Hz, 1H), 3.99-3.97 (m, 4H), 3.51-3.48 (m, 4H), 2.35-2.32 (m, 1H), 1.97-1.94 (m, 1H), 1.10-1.06 (m, 3H).

Compound TH1768 was synthesized in the same manner as TH1767. $^1$H NMR (400 MHz, CDCl$_3$) δ: 8.42 (s, 1H), 8.21 (t, J=8.0 Hz, 2H), 7.78 (t, J=7.2 Hz, 1H), 7.66 (t, J=7.2 Hz, 1H), 5.75 (d, J=16.8 Hz, 1H), 5.44 (s, 2H), 5.28 (d, J=16.8 Hz, 1H), 4.03-4.01 (m, 2H), 3.68-3.66 (m, 2H), 2.35-2.33 (m, 1H), 1.96-1.94 (m, 1H), 1.08 (t, J=7.2 Hz, 3H).

Compound TH1770 was synthesized in the same manner as TH1767. $^1$H NMR (400 MHz, CDCl$_3$) δ: 8.26-8.22 (m, 3H), 7.79 (t, J=7.2 Hz, 1H), 7.67 (t, J=7.2 Hz, 1H), 5.76 (d, J=16.4 Hz, 1H), 5.48 (s, 2H), 5.28 (d, J=16.4 Hz, 1H), 5.53 (s, 4H), 2.70 (s, 4H), 2.42 (s, 3H), 2.35-2.32 (m, 1H), 1.98-1.96 (m, 1H), 1.07 (t, J=7.2 Hz, 3H).

Compound TH1771 was synthesized in the same manner as TH1767. $^1$H NMR (400 MHz, CDCl$_3$) δ: 9.09 (s, 1H), 8.31 (d, J=8.4 Hz, 1H), 8.20 (d, J=8.4 Hz, 1H), 7.84 (t, J=7.6 Hz, 1H), 7.76 (t, J=7.6 Hz, 1H), 6.12-6.09 (m, 1H), 5.78 (d, J=16.0 Hz, 1H), 5.50 (d, J=17.2 Hz, 1H), 5.43 (s, 2H), 5.41 (d, J=14.8 Hz, 1H), 5.29 (d, J=16.0 Hz, 1H), 4.90 (d, J=6.0 Hz, 2H), 2.36-2.33 (m, 1H), 1.98-1.95 (m, 1H), 1.08 (t, J=7.2 Hz, 3H).

Compounds TH1775, TH1777, and TH1778 were synthesized using the following reaction scheme.

TH1777 was prepared as follows. A 25 mL round bottom flask was charged with compound TH1767 (30 mg, 0.059 mmol), MeOH (5 mL) and 10% Pd/C (10 mg). The reaction vessel was purged with hydrogen three times and then the mixture was stirred under hydrogen (using a hydrogen balloon) at room temperature for 3 h. The catalyst was filtered and the filtrate was concentrated under reduced pressure. The residue was purified via flash chromatography (12 g of silica gel, 0-10% MeOH/DCM eluting) to afford TH1777 as a yellow solid (10 mg, 36%). $^1$H NMR (400 MHz, CDCl$_3$) δ: 8.28 (s, 1H), 8.18 (d, J=8.4 Hz, 1H), 8.09 (d, J=8.8 Hz, 1H), 7.72 (t, J=8.0 Hz, 1H), 7.55 (t, J=8.0 Hz, 1H), 5.76 (d, J=16.8 Hz, 1H), 5.39 (s, 2H), 5.25 (d, J=16.8 Hz, 1H), 3.97-3.95 (m, 4H), 3.45-3.42 (m, 4H), 2.17-2.15 (m, 1H), 1.97-1.93 (m, 1H), 1.69 (br, 2H), 1.06 (t, J=7.2 Hz, 3H).

TH1778 was synthesized in the same manner as TH1777.
TH1775 was synthesized in the same manner as TH1777.
¹H NMR (400 MHz, CDCl₃) δ: 8.13 (s, 1H), 8.12 (d, J=7.2 Hz, 1H), 8.03 (d, J=8.4 Hz, 1H), 7.67 (t, J=7.2 Hz, 1H), 7.50 (t, J=7.2 Hz, 1H), 5.75 (d, J=16.8 Hz, 1H), 5.32 (s, 2H), 5.23 (t, J=16.8 Hz, 1H), 3.48-3.46 (m, 4H), 2.70-2.67 (m, 4H), 2.19-2.16 (m, 1H), 1.96-1.93 (m, 1H), 1.06 (t, J=7.6 Hz, 1H).

Compound TH1776 was made from TH1771 using the following reaction scheme.

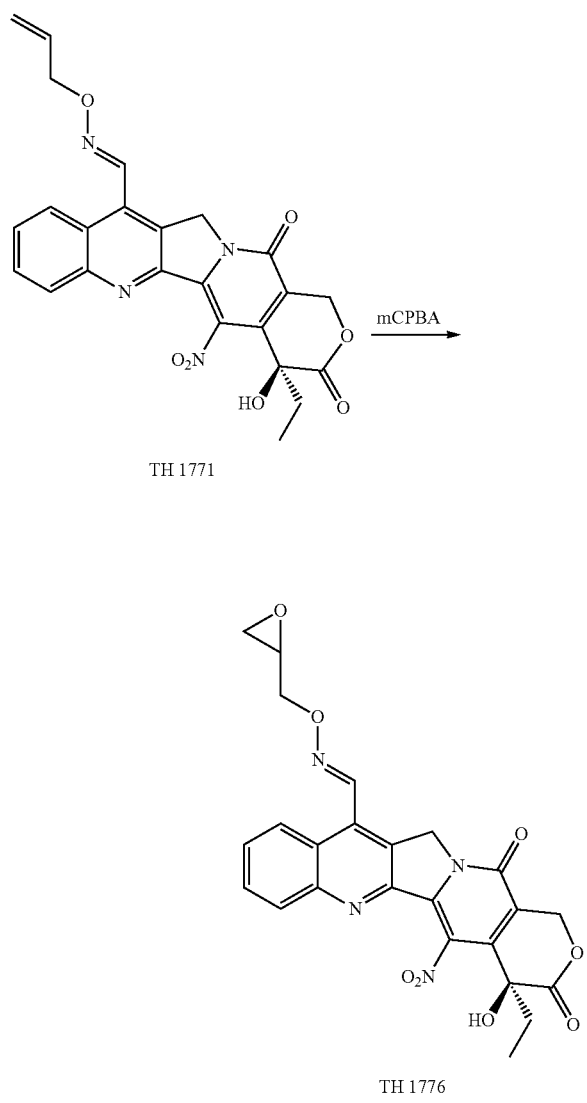

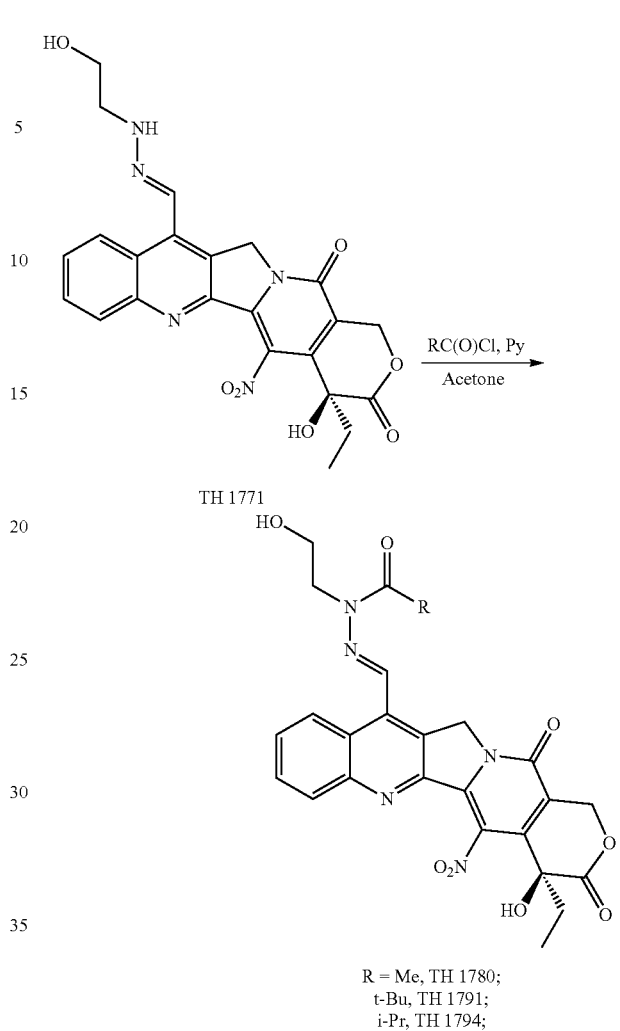

To prepare TH1776, a 25 mL round bottom flask was charged with compound TH1771 (10 mg, 0.021 mmol), m-CPBA (77%, 10 mg, 0.042 mmol) and DCM (4 mL). The mixture was stirred at room temperature for 2 h and then purified via flash chromatography (12 g of silica gel, 0-100% EtOAc/Hexane eluting) to afford TH1776 as a yellow solid (3 mg, 61%).

Compounds TH1780, TH1791, TH1794, and TH1797 were made from TH1771 using the following reaction scheme.

To prepare TH1780, a 25 mL round bottom flask was charged with compound TH1771 (10 mg, 0.021 mmol), pyridine (50 mg, 0.63 mmol) and acetone (4 mL). The mixture was cooled in an ice-water bath and acetyl chloride (40 mg, 0.51 mmol) was added to it. The mixture was stirred at 0° C. for 2 h, and then purified by flash chromatography (12 g of silica gel, 0-100% EtOAc/Hexane eluting) to afford TH1780 as a yellow solid (40 mg, 92%). ¹H NMR (400 MHz, CDCl₃) δ: 9.09 (s, 1H), 8.57 (d, J=8.8 Hz, 1H), 8.33 (d, J=8.0 Hz, 1H), 7.89-7.82 (m, 2H), 5.75 (d, J=16.4 Hz, 1H), 5.49 (s, 2H), 5.29 (d, J=16.4 Hz, 1H), 4.42-4.40 (m, 2H), 4.34-4.32 (m, 2H), 2.36-2.32 (m, 1H), 2.12 (s, 3H), 1.96-1.94 (m, 1H), 1.07 (t, J=7.2 Hz, 3H).

TH1791 was synthesized in the same manner as TH1780. ¹H NMR (400 MHz, CDCl₃) δ: 8.23-8.21 (m, 2H), 7.83 (s, 1H), 7.78 (t, J=8.4 Hz, 1H), 7.65 (t, J=8.4 Hz, 1H), 5.76 (d, J=16.8 Hz, 1H), 5.44 (s, 2H), 5.28 (d, J=16.8 Hz, 1H), 4.34 (t, J=6.4 Hz, 2H), 3.63 (t, J=6.4 Hz, 2H), 2.35-2.33 (m, 1H), 1.97-1.96 (m, 1H), 1.56 (s, 9H), 1.07 (t, J=7.6 Hz, 3H).

TH1794 was synthesized in the same manner as TH1780. ¹H NMR (400 MHz, CDCl₃) δ: 8.39 (s, 1H), 8.25-8.22 (m, 2H), 7.83-7.78 (m, 1H), 7.67-7.64 (m, 1H), 5.78 (d, J=16.8 Hz, 1H), 5.45 (s, 2H), 5.29 (d, J=16.8 Hz, 1H), 4.37-4.34 (m, 2H), 3.68-3.64 (m, 3H), 2.38-2.34 (m, 1H), 1.97-1.94 (m, 1H), 1.26-1.19 (m, 6H), 1.08 (t, J=7.6 Hz, 3H).

TH1797 was synthesized in the same manner as TH1780. ¹H NMR (400 MHz, CDCl₃) δ: 9.12 (s, 1H), 8.42 (d, J=8.4 Hz, 1H), 8.23 (d, J=8.8 Hz, 1H), 8.11-8.04 (m, 4H), 7.82-7.79 (m, 1H), 7.66-07.33 (m, 4H), 5.70 (d, J=16.8 Hz, 1H), 5.30 (s, 2H), 5.22 (d, J=16.8 Hz, 1H), 4.67-4.62 (m, 2H), 4.15-4.11 (m, 2H), 2.32-2.27 (m, 1H), 1.96-1.89 (m, 1H), 1.07 (t, J=7.6 Hz, 3H).

Compounds TH1783, TH1793, and TH1796 were synthesized using the following reaction scheme using methods similar to that described above for the synthesis of TH1777.

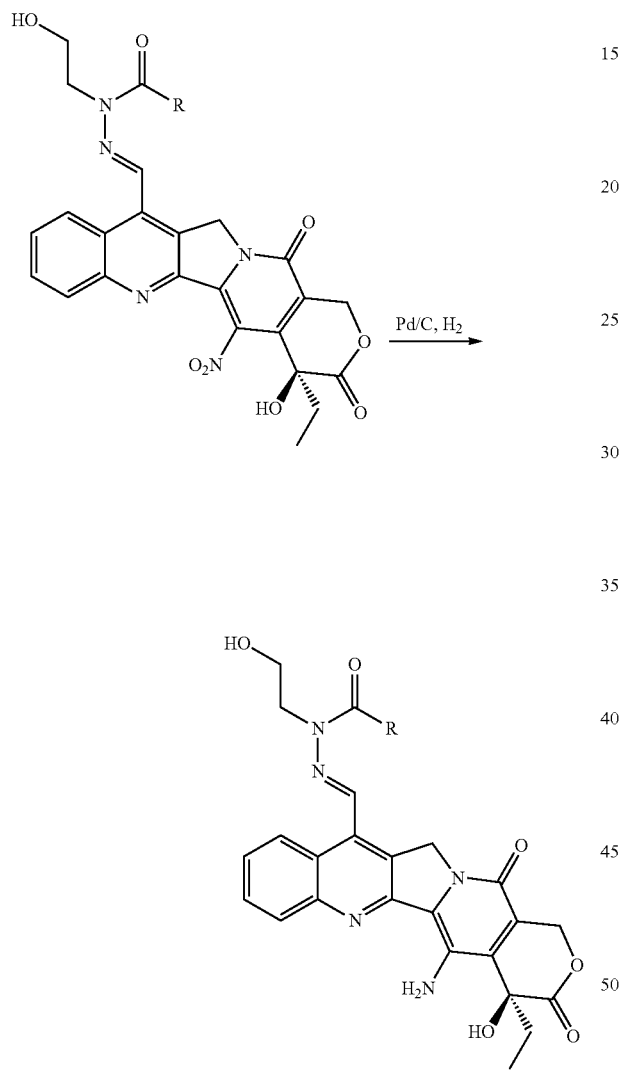

R = Me, TH 1783;
t-Bu, TH 1793;
i-Pr, TH 1796.

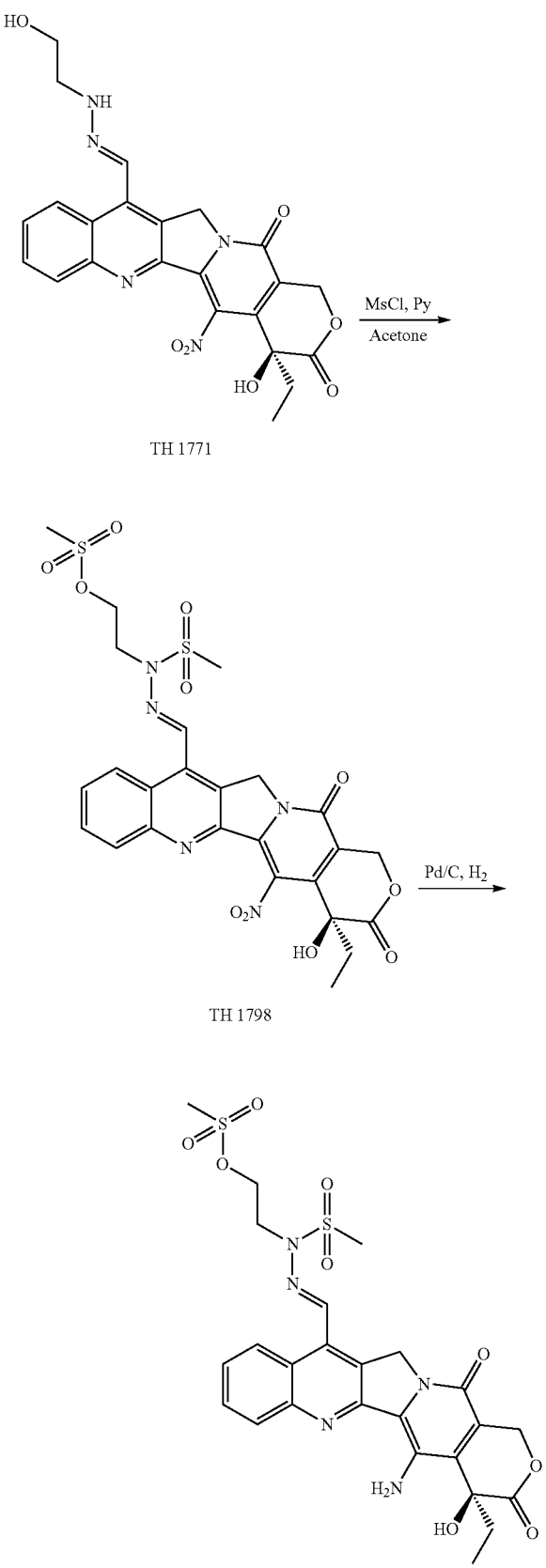

Compounds TH1798 and TH1799 were synthesized using the following reaction scheme using methodology similar to that described above for TH1780 and TH1777.

TH1803 was prepared as follows.

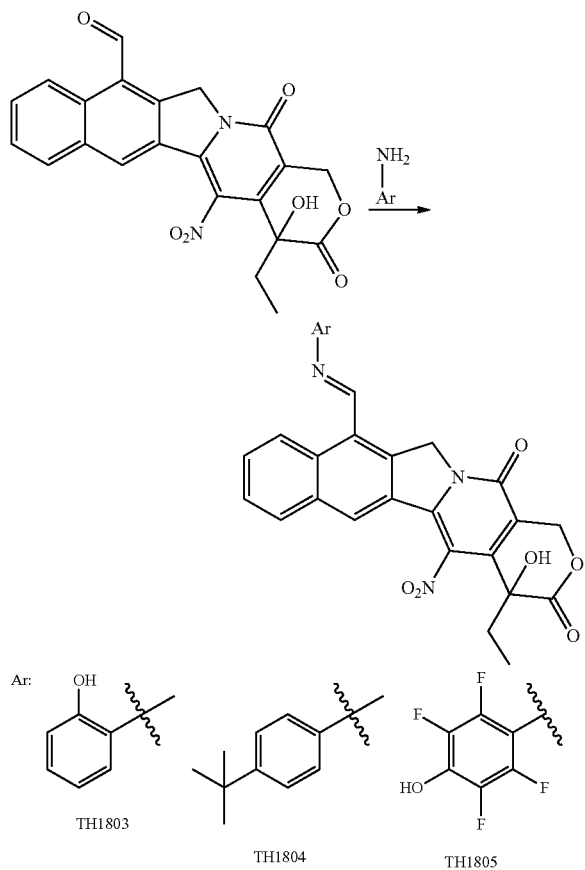

To a suspension of the 7-formyl-14-nitro camptothecin (TH1762) (100 mg, 0.25 mmol) in 7 ml anhydrous DCM was added 2-aminophenol (82 mg, 0.75 mmol) and trifluoromethanesulfonic acid Ytterbium (III) (16 mg, 0.03 mmol) at room temperature. The resulting mixture was stirred for three hours until the reaction was complete. Solvent was removed and the residue was purified with flash chromatography on silica gel (MeOH on DCM from 0 to 8%) and then recrystallized from MeOH to give pure product (85 mg, 66% yield). $^1$H NMR (CDCl$_3$) δ: 9.60 (s, 1H), 8.43 (d, 1H, J=8.0 Hz), 8.25 (d, 1H, J=7.6 Hz), 7.79 (t, 1H, J=7.6 Hz), 7.73 (t, 1H, J=7.6 Hz), 7.31 (d, 1H, J=7.6 Hz), 7.22 (t, 1H, J=7.6 Hz), 7.0 (d, 1H, J=8.0 Hz), 6.93 (t, 1H, J=7.6 Hz), 5.65 (dd, 2H, J=20.5 Hz and 21.0 Hz), 5.62 (d, 1H, J=16.8 Hz), 5.21 (d, 1H, J=16.8 Hz), 2.30 (m, 1H), 1.98 (m, 1H), and 1.0 (m, 3H).

The same procedure used to synthesize TH1803 was used to synthesize TH1804, TH1805 and TH1809.

TH1804: (yield 77%) $^1$H NMR (CDCl$_3$) δ: 9.40 (s, 1H), 8.38 (d, 1H, J=8.4 Hz), 8.03 (d, 1H, J=8.4 Hz), 7.70 (t, 1H, J=7.2 Hz), 7.64 (t, 1H, J=7.6 Hz), 7.53 (d, 2H, J=7.6 Hz), 7.40 (d, 2H, J=7.6 Hz), 5.51 (dd, 2H, J=20.5 Hz and 21.0 Hz), 5.64 (d, 1H, J=16.8 Hz), 5.21 (d, 1H, J=16.8 Hz), 2.27 (m, 1H), 1.98 (m, 1H), and 1.04 (t, 3H, J=7.2 Hz)

TH1805: (yield 55%). $^1$H NMR (DMSO-d$_6$) δ: 10.0 (s, 1H), 8.88 (d, 1H, J=8.0 Hz), 8.10 (d, 1H, J=8.0 Hz), 7.98 (m, 2H), 6.88 (s, 1H), 5.55 (m, 4H), 2.30 (m, 1H), 2.05 (m, 1H), and 1.0 (t, 3H, J=7.2 Hz).

TH1809 (yield 38%). $^1$H NMR (CDCl$_3$) δ: 9.41 (s, 1H), 8.40 (d, 1H, J=8.4 Hz), 8.15 (d, 1H, J=8.4 Hz), 7.75 (t, 1H, J=7.2 Hz), 7.63 (t, 1H, J=7.6 Hz), 7.52 (d, 2H, J=7.6 Hz), 7.38 (d, 2H, J=7.6 Hz), 6.52 (bs, 2H), 5.6 (s, 2H), 5.80 (d, 1H, J=16.8 Hz), 5.25 (d, 1H, J=16.8 Hz), 2.18 (m, 1H), 1.95 (m, 1H), and 1.08 (t, 3H, J=7.2 Hz)

TH1814 was prepared as follows. To a suspension of the 7-formyl-14-nitro camptothecin (TH1762) (20 mg, 0.05 mmol) in 2 ml anhydrous DCM was added an excess of neopentyl amine (50 microliters) and trifluoromethanesulfonic acid Ytterbium (III) (5 mg, 0.01 mmol) at room temperature with approximately 50 mg of activated 4A molecular sieves. The resulting mixture was stirred for three days. The reaction was diluted with DCM, filtered to remove the sieves and extracted with saturated sodium bicarbonate, and the DCM layer was dried with Na$_2$SO$_4$ and dried under reduced pressure. The residue was dissolved in 2 ml of methanol-ethyl acetate (¼) and 10 mg of 10 Pd/C were added. The flask was flushed with H$_2$ gas and stirred overnight at room temperature, filtered and concentrated. The mixture was purified by preparative thin layer chromatography (5% MeOH/DCM as the eluant) to yield 1 mg of product. $^1$H NMR (CDCl$_3$) δ: 8.20 (d, 1H, J=8.4 Hz), 8.10 (d, 1H, J=8.4 Hz), 7.73 (t, 1H, J=7.2 Hz), 7.58 (t, 1H, J=7.6 Hz), 6.50 (bs, 2H), 5.74 (d, 1H, J=16.8 Hz), 5.34 (s, 2H), 5.24 (d, 1H, J=16.8 Hz), 4.31 (bs, 2H), 2.45 (s, 2H), 2.16 (m, 1H), 1.95 (m, 1H), 1.07 (t, 3H, J=7.2 Hz), and 0.89 (s, 9H)

Example 2

In Vitro Testing

2. A. Demonstration of Antiproliferative Activity

The data below demonstrate that the compounds of the present invention have antitumor activity against lung carcinoma, prostate carcinoma, colon carcinoma, melanoma, and a variety of other cancer cell types. The compounds were screened for cytotoxicity using human non small cell lung cancer cell line H460. Cells were treated with test compounds at various concentrations under air for 72 hrs, and then cell viability and proliferation were assessed by Alamar Blue staining. The IC$_{50}$ values for the inhibition of proliferation for the tested compounds are shown in the following table.

TABLE 2

| Compound # | IC$_{50}$ (nM) | TH comp. | IC$_{50}$ (nM) | TH comp. | IC$_{50}$ (nM) | TH comp. | IC$_{50}$ (nM) |
|---|---|---|---|---|---|---|---|
| Camptothecin | 14 | TH1525 | >1000 | TH1768 | 6600 | TH1791 | 4000 |
| Topotecan | 45 | TH1589 | 59 | TH1769 | 330 | TH1793 | 19 |
| TH1317 | >1000 | TH1598 | 89 | TH1770 | 9100 | TH1794 | 2300 |
| TH1320 | 18 | TH1599 | 4.3 | TH1771 | >10000 | TH1796 | 12 |
| TH1332 | 66 | TH1626 | >1000 | TH1775 | 26 | TH1797 | 40000 |
| TH1338 | 7.2 | TH1627 | >1000 | TH1776 | 3200 | TH1798 | 2500 |
| TH1339 | 1.8 | TH1628 | 62 | TH1777 | 16 | TH1799 | 8.1 |
| TH1385 | >1000 | TH1631 | 7.4 | TH1778 | 270 | TH1800 | 220 |
| TH1386 | 71 | TH1636 | 6200 | TH1780 | 28000 | TH1801 | 23 |

TABLE 2-continued

| Compound # | IC$_{50}$ (nM) | TH comp. | IC$_{50}$ (nM) | TH comp. | IC$_{50}$ (nM) | TH comp. | IC$_{50}$ (nM) |
|---|---|---|---|---|---|---|---|
| TH1408 | 66 | TH1637 | 4558 | TH1781 | 28000 | TH1803 | 3600 |
| TH1431 | 800 | TH1643 | 43 | TH1783 | 460 | TH1804 | >50000 |
| TH1333 | >1000 | TH1644 | 800 | TH1784 | 4900 | TH1805 | 49000 |
| TH1446 | 850 | TH1650 | 685 | TH1785 | 39 | TH1809 | 1400 |
| TH1499 | 19 | TH1651 | 6.2 | TH1786 | 21000 | TH1811 | 14 |
| TH1522 | >1000 | TH1762 | 7200 | TH1787 | 12 | TH1812 | 2800 |
| TH1523 | 830 | TH1766 | >1000 | TH1789 | 31 | TH1814 | 15 |
| TH1524 | >1000 | TH1767 | 6000 | TH1790 | 46 | TH1816 | 23 |

SN-38, the active toxin derived from the marketed drug irinotecan was also tested in H460 and had an IC$_{50}$ of 54 nM. The low potency (high IC$_{50}$ values) for the 14-nitro camptothecin derivatives of the present invention are consistent with their usefulness as hypoxically activated drugs, i.e., as prodrugs. The selective hypoxic activation of the nitro compounds of the invention to the amino compounds of the invention is demonstrated below. The greater cytotoxicity of the 14-amino derivatives produced is evidenced by the lower (nanomolar) IC$_{50}$s for the amino compounds of the invention, which are similar to the IC$_{50}$s for the camptothecin derivatives topotecan and SN-38.

Certain compounds of the present invention, along with positive controls, were also screened for cytotoxicity using 10 different cancer cell lines: mouse melanoma cell line B-16-F10, human melanoma cell lines: SKMEL-28, SKMEL2, A375 and MAMLE-3M, human prostate cancer cell lines PC-3, LNCap, and DU145, human colon cancer cell line HT-29, and human ovarian cancer cell line IGROV-1. Cells were treated with test compounds at various concentrations under air for 72 hrs, and then cell viability and proliferation were assessed by Alamar Blue staining. The IC$_{50}$ values (nM) for the inhibition of proliferation for the tested compounds are shown in Table 3.

TABLE 3

| Comp. # | B16-F10 IC$_{50}$ | PC3 IC$_{50}$ | HT29 IC$_{50}$ | SKMEL-2 IC$_{50}$ | SKMEL-28 IC$_{50}$ | A375 IC$_{50}$ | MAMLE-3M IC$_{50}$ | DU145 IC$_{50}$ | LNCaP IC$_{50}$ | IGROV-1 IC$_{50}$ |
|---|---|---|---|---|---|---|---|---|---|---|
| TH1320 | 950 | 43 | 229 | 170 | 3000 | 22 | 776 | 50 | 110 | 120 |
| TH1338 |  | 24 | 302 | 130 | >10,000 | 7 | 1200 | 18 | 120 | 20 |
| TH1339 | 690 | 9 | 69 | 50 | >10,000 | 3 | 220 | 2.5 | 23 | 10 |
| TH1390 | 950 | 26 | 177 |  |  |  |  |  |  |  |
| TH1431 | 720 | 29 | 288 |  |  |  |  |  |  |  |
| TH1495 |  | 4 | 33 |  |  |  |  |  |  |  |
| TH1553 |  | 14 | 224 |  |  |  |  |  |  |  |
| Topotecan |  | 45 | >1000 | 140 | >10,000 | 13 | 1000 | 30 | 9 | 160 |
| SN-38 |  | 4 | 224 | 100 | 10,000 | 4 | 200 | 4 | 9 | 30 |

2. B. Compounds of the Invention Overcome Efflux Pump Mediated Drug Resistance

The data below shows the anti-proliferative effect of camptothecin derivatives (including certain compounds of the invention) on cell lines over-expressing certain drug resistance efflux pumps. Cellular drug resistance was determined using the antiproliferation assay described above.

The camptothecin derivatives were tested in the Messa ovarian carcinoma cell line and the isogenic line, DX5, which over expresses the MDR 1 efflux pump. Compounds of this invention are generally not substantially effluxed by MDR 1. The results are tabulated in Table 4.

To test their susceptibility to the MRP1 (multidrug resistance protein 1) efflux pump, the camptothecin derivatives were also tested in H69 small cell lung cancer line and the isogenic MRP1 over expressing H69AR line. The results are tabulated in Table 5. The results demonstrate that the cell lines expressing this resistance-conferring protein were up to about 40 fold more resistant to camptothecin and the other known derivatives tested in this assay, Topotecan and SN-38 (SN-38 being the active toxin derived from the clinically utilized Irinotecan), than cells not expressing the resistance-conferring protein. In marked contrast, cells expressing this resistance-conferring protein demonstrated much lower resistance to the compounds of this invention.

The camptothecin derivatives were also tested in pcDNA and the isogenic line BCRP, which over expressed the breast cancer resistance protein, a known efflux pump. The results are tabulated in Table 6. The overexpressing line was resistant to Topotecan and SN-38. The cytotoxicities of the compounds of this invention were only marginally diminished in the overexpressing line compared to the corresponding parent line. Certain 14-nitro derivatives of the present invention, which demonstrate somewhat high IC$_{50}$s, were incubated for 5 days, while the more potent 14-amino derivatives were incubated for 3 days. The ratio of the IC$_{50}$s for the efflux pump over expressing line versus the parent line are typically near 1 for the compounds of the present invention, demonstrating the lack of resistance to the compounds of the present invention conferred by over expression of these clinically relevant efflux pumps.

In contrast, topotecan, camptothecin, and SN-38 demonstrated the following resistance profile. Topotecan, camptothecin, and SN-38 demonstrated a resistance ratio for MDR 1 over-expression, versus the parent cell line, of 7.5, 0.9 and 2.2 respectively. Against the MRP1 over expressing line, the ratio versus the parent cell line was >47, >250 and 11. Against the BCRP over expressing line, the ratio versus the parent cell line was 51, 1.6 and >220 respectively. These resistance profiles demonstrate the susceptibility of the known camptothecin derivatives to known drug resistance mechanisms.

TABLE 4

| TH no. | Air 3d MESSA prol. IC$_{50}$ nM | Air 3d DX5 MESSA prol. IC$_{50}$ nM | 3d DX5/ MESSA | Air 5d MESSA prol. IC$_{50}$ nM | Air 5d DX5 prol. IC$_{50}$ nM | 5d DX5/ MESSA |
|---|---|---|---|---|---|---|
| 1317 | | | | >500 | >500 | |
| 1320 | 58 | 60 | 1.034 | | | |
| 1332 | 5300 | 6300 | 1.2 | 2332 | 2742 | 1.17 |
| 1333 | 15000 | 34000 | 2.3 | | | |
| 1338 | 4.3 | 12 | 2.791 | | | |
| 1339 | 8.5 | 6.7 | 0.788 | | | |
| 1386 | 52 | 28 | 0.538 | | | |
| 1408 | 81 | 40 | 0.5 | | | |
| 1431 | 2692 | 1122 | 0.4 | 255 | 515 | 2.0196 |
| 1431 | 3300 | 4900 | 1.5 | | | |
| 1446 | | | | 4454 | 4961 | 1.113 |
| 1499 | 9 | 5 | 0.556 | | | |
| 1553 | 20 | 18 | 0.9 | | | |

TABLE 5

| TH no. | Air 3d H69 prol. IC$_{50}$ nM | Air 3d H69ar (MRP1) prol. IC$_{50}$ nM | 3d H69AR/H69 | Air 5d H69 prol. IC$_{50}$ nM | Air 5d H69ar (MRP1) prol. IC$_{50}$ nM | 5d H69AR/H69 |
|---|---|---|---|---|---|---|
| 1317 | | | | 933 | 1317 | 1.4116 |
| 1320 | 91 | 91 | | | | |
| 1332 | | | | 4221 | 8709 | 2.0633 |
| 1333 | | | | | | |
| 1338 | 110 | 240 | 2.1818 | | | |
| 1339 | 13 | 28 | 2.1538 | | | |
| 1386 | 141 | 195 | 1.383 | | | |
| 1408 | 242 | 285 | 1.1777 | | | |
| 1431 | 3789 | >10000 | >2.6 | 354 | 838 | 2.36 |
| 1431 | | | | | | |
| 1446 | | | | 2742 | 8506 | 3.1 |
| 1499 | 217 | 463 | 2.1336 | | | |
| 1553 | 175 | 1781 | 1.177 | | | |

TABLE 6

| TH no. | Air 3d pcDNA prol. IC$_{50}$ nM | Air 3d BCRP (MRP1) prol. IC$_{50}$ nM | 3d BCRP/ pcDNA | Air 5d pcDNA prol. IC$_{50}$ nM | Air 5d BCRP (MRP1) prol. IC$_{50}$ nM | 5d BCRP/ pcDNA |
|---|---|---|---|---|---|---|
| 1317 | | | | 57 | 82 | 1.4386 |
| 1320 | 7.4 | 14 | 1.8919 | | | |
| 1332 | 1800 | 2300 | 1.3 | 24 | 21 | 0.875 |
| 1333 | 3900 | 7800 | 2 | | | |
| 1338 | 4.3 | 4.9 | 1.1395 | | | |
| 1339 | 2.3 | 2.1 | 0.913 | | | |
| 1386 | 5.6 | 26.6 | 4.75 | | | |
| 1408 | 9.5 | 7.3 | 0.7684 | | | |
| 1431 | 461 | 488 | 1.0586 | 67 | 78 | 1.1642 |
| 1431 | 900 | 3100 | 3.4 | | | |
| 1446 | 574 | 2742 | 4.777 | | | |
| 1499 | 3.2 | 3.4 | 1.0625 | | | |
| 1553 | 1.9 | 15 | 7.8947 | | | |

2. C. Assessment of Bone Marrow Toxicity

Camptothecin derivatives previously reported are known to demonstrate severe marrow toxicity in humans, and that toxicity can be determined by the bone marrow progenitor cell clonogenic assay. A clonogenic assay was performed using bone marrow progenitor cells derived from the blood of mice and humans. IC$_{50}$s and IC$_{90}$s of various camptothecin derivatives were determined for cells of both species and are tabulated below. The known camptothecin derivatives, topotecan, SN-38 and 9-amino camptothecin, all showed low nanomolar IC$_{50}$s against human bone marrow progenitor cells. The compounds of the invention were generally far less toxic.

TABLE 7

| compound | Mouse CFU-GM (IC$_{50}$ nM) THLD | Human CFU-GM (IC$_{50}$ nM) THLD | Ratio | Mouse CFU-GM (IC$_{90}$ nM) THLD | Human CFU-GM (IC$_{90}$ nM) THLD | Ratio |
|---|---|---|---|---|---|---|
| TH1320 | 710 | 130 | 6 | 4800 | 1100 | 4 |
| TH1332 | >10000 | >1000 | nd | >10,000 | >100 | nd |
| TH1338 | 620 | 100 | 6 | 4500 | 650 | 7 |
| TH1339 | 560 | 10 | 56 | 2200 | 100 | 22 |
| TH1386 | 680 | 30 | 23 | 3500 | 210 | 17 |
| TH1408 | 700 | 90 | 8 | 5000 | 650 | 8 |
| TH1589 | 920 | 110 | 8 | 6200 | 680 | 9 |
| TH1600 | 90 | 1.2 | 75 | 700 | 8 | 88 |
| Topotecan | 130 | 8 | 16 | 700 | 50 | 14 |
| SN-38 | 110 | 1.3 | 85 | 800 | 8 | 100 |
| 9-amino camptothecin | 90 | 1.2 | 75 | 700 | 8 | 88 |

2. D. Demonstration of Selective Hypoxic Activation of TH1332 and TH1431 in Cell Culture H46O cells were grown to a confluent monolayer and then the 14-nitro TH1332 prodrug was added to the media at 5 micromolar concentration. Incubations were done for 24 hour either under air or nitrogen (hypoxia), media and cells were recovered, sonicated and soluble extracts were isolated by acetonitrile precipitation of proteins. The level of amino TH1338 active cytotoxin were quantitated by liquid chromotagraphy mass spectra analysis. The equivalent of 70 nanomolar TH1338 was produced under hypoxia with undetectable levels being produced under air (less than 5 nanomolar). This demonstrates the selective conversion under hypoxia of the less cytotoxic nitro prodrug TH1332 to the more cytotoxic amino active toxin TH1338.

The analogous experiment was preformed using 1 micromolar concentration of the 14-nitro derivative TH1431. After 24 hr, 180 nanomolar of the 14 amino TH1499 was produced under nitrogen with undetectable levels produced under air (less than 5 nanomolar). This demonstrates the selective conversion under hypoxia of the less cytotoxic nitro prodrug TH1431 to the cytotoxic 14-amino derivative TH1499.

Example 3

In Vivo Testing

3. A. Anti-Tumor Activity in Xenograft Models

The antitumor activity of certain compounds of the invention was demonstrated in four different xenograft models (human non small cell lung cancer H-460, human colon cancer HT-29, human prostate cancer PC-3 and ovarian cancer IGROV1) in nude mice. The first three models were produced by subcutaneous implantation of the appropriate number of cells into the flank of the animals. When tumor size was approximately 150 mm$^3$, animals were randomized into groups of 10 mice each for dosing. One arm was dosed with only vehicle and the results used for the efficacy calculations. The tested compounds along with the control compound topotecan were given orally (PO) for 5 days a week (QD×5/wk) for 2 or 4 weeks. Tumor growth inhibition (TGI) and maximum body weight loss (Max BWL) for each compound is listed in Table 8. TGI=(1−T/C) %. T/C ratio was calculated as T/C=(Tn−Ti)/(Cn−Ci), where Tn is tumor volume in treatment group on Day n, and Ti is the initial tumor volume in the treatment group. Cn is the tumor volume of the vehicle group on the last day of measurement. Ci is the initial tumor volume in the vehicle control group. Day n is the last measurement taken when all the animals in the vehicle group were not yet euthanized. Animals were euthanized when tumor volumes grew larger than 2000 mm$^3$. A TGI of 100 represents no tumor growth in the treated group at the day which the vehicle animals need to be sacrificed for ethical reasons due to large tumors (>2000 mm$^3$). A TGI greater than 100 results from tumor regression from the initial reading. A TGI of 50 represents that the treated tumor grew, on average, only to half the volume relative to the tumors of the average vehicle administered animals.

A xenograft model of metastatic ovarian cancer was set up by the intraperitoneal (i.p) injection of 3×10$^6$ IGROV1 human ovarian cancer cells in nude mice. Mice were evaluated twice a week for morbidity and mortality. Kaplan-Meier survival curves were plotted. Median survival times of treated mice divided by the median survival of vehicle treated mice times 100 are reported as the T/C. Therefore, treated animals living twice as long as the vehicle animals have a T/C of 200. In addition to the topotecan control, karenitecin, a camptothecin analog currently in clinical trials, was also tested at a 1.5 mg/kg dose and resulted in a T/C value of 182.

The results from the test compounds (Table 8(a)) and the control molecule, topotecan (Table 8(b)), are listed in the table below. These results demonstrate that TH1332, TH1338, and TH1320 were more efficacious and less toxic than topotecan.

CD-mice by dosing via oral gauvage using a 5% DMSO, 5% Tween 80 suspension in water as the formulation. The data normalized to a 50 mg/kg dose are shown below (compounds were dosed at either 25 or 50 mg/kg). All compounds showed enhanced exposure relative to a camptothecin control as evidenced by significant maximum concentration (Cmax) and area under the curve (AUC). Additionally, the less active 14-nitro prodrugs TH1332 and TH1431 showed very little conversion in vivo (less than 1%) to the respective cytotoxic, 14-amino derivatives, TH1338 and TH1499, again demonstrating that TH1332 and TH1431 are stable prodrugs under normoxic conditions.

TABLE 9

|  | Cmax (μg/mL) | AUC (μg-min/mL) | Half-Life (min) |
| --- | --- | --- | --- |
| TH1317 | 0 | 0 | Not calculated (NC) |
| TH1339 | 0.378 | 24.3 | NC |
| Camptothecin | 0.374 | 58.1 | 119 |
| TH1320 | 0.547 | 97 | 119 |
| TH1386 | 5.86 | 186 | 25.6 |
| TH1446 | 5.1 | 257 | 35.4 |
| TH1408 | 6.07 | 506 | 48.3 |
| TH1431 | 0.348 | 21.1 | NC |
| TH1332 | 0.38 | 109 | 375 |
| TH1338 | 0.25 | 64.2 | 250 |

TABLE 8(a)

| Comp. | Cell line | Schedule | Weeks | Route | Dose (mg/Kg) | TGI (%) | Max. BWL (%) | T/C |
| --- | --- | --- | --- | --- | --- | --- | --- | --- |
| TH1320 | H460 | QD × 5/wk | 2 | PO | 30 | 79.2 | 3.8 |  |
|  | HT29 | QD × 5/wk | 2 | PO | 30 | 44.3 | 3 |  |
|  | IGROV1 | QD × 5/wk | 4 | PO | 20 |  |  | 204 |
| TH1338 | H460 | QD × 5/wk | 2 | PO | 40 | 84.3 | 1.5 |  |
|  | HT29 | QD × 5/wk | 4 | PO | 40 | 100.7 | 2.9 |  |
|  | IGROV1 | QD × 5/wk | 4 | PO | 40 |  |  | 221 |
|  | PC3 | QD × 5/wk | 2 | PO | 40 | 107 | 7 |  |
| TH1332 | H460 | QD × 5/wk | 2 | PO | 150 | 91.4 | 11.4 |  |
|  | HT29 | QD × 5/wk | 4 | PO | 150 | 62.8 | 0 |  |
|  | IGROV1 | QD × 5/wk | 4 | PO | 150 |  |  | 159 |
|  | PC3 | QD × 5/wk | 2 | PO | 150 | 103 | 1.8 |  |
| TH1339 | H460 | QD × 5/wk | 2 | PO | 15 | 46.1 | 0 |  |
|  | HT29 | QD × 5/wk | 2 | PO | 30 | 56.5 | 3 |  |
|  | IGROV1 | QD × 5/wk | 4 | PO | 20 |  |  | 280 |
| TH1446 | HT29 | QD × 5/wk | 2 | PO | 40 | 29.5 | 1.1 |  |
| TH1499 | HT29 | QD × 5/wk | 2 | PO | 25 | 4.7 | 1.8 |  |
| TH1431 | HT29 | QD × 5/wk | 2 | PO | 25 | 34.6 | 1.6 |  |
| TH1650 | H460 | QD × 5/wk | 2 | PO | 40 | 85 | 6.7 |  |
| TH1651 | PC3 | QD × 5/wk | 2 | PO | 40 | 80 | 4.8 |  |
|  | H460 | QD × 5/wk | 2 | PO | 40 | 80 | 5.5 |  |
| TH1589 | PC3 | QD × 5/wk | 2 | PO | 40 | 80 | 0.1 |  |
|  | H460 | QD × 5/wk | 2 | PO | 30 | 76 | 10.4 |  |

TABLE 8(b)

| Comp. | Cell line | Schedule | Weeks | Route | Dose (mg/Kg) | TGI (%) | Max BWL (%) | T/C |
| --- | --- | --- | --- | --- | --- | --- | --- | --- |
| Topotecan | H460 | QD × 5/wk | 2 | PO | 2 | 46.1 | 8.9 |  |
|  | HT29 | QD × 5/wk | 4 | PO | 2 | 70.3 | 0 |  |
|  | IGROV1 (ip) | QD × 5/wk | 4 | PO | 2 |  |  | 186 |
|  | PC3 | QD × 5/wk | 2 | PO | 2 | 79 | 1.3 |  |

3. B. Pharmacokinetics

The in vivo pharmacokinetics of several 14-nitro and 14-amino camptothecins of the invention were determined in C. Brain Penetration Certain compounds of the invention were assessed for brain penetration by comparing the AUC for plasma exposure versus the AUC in brain. TH1320 showed brain levels that were 115% of plasma levels. TH1332, TH1338, and TH1431 showed brain levels relative to plasma of 18%, 70% and 12% respectively. Topotecan is used clinically for brain metastases and shows brain levels in mice which are about 30% that of plasma levels. These results demonstrate that certain compounds of this invention have superior brain penetration relative to topotecan, the current standard for the brain penetration of a camptothecin derivative.

3. D. Oral Bioavailability

Rats are often a useful species for predicting oral bioavailablity in humans. In Sprague-Dawley rats, the bioavailability of TH1338 was high (88.9%), indicating that the compound is orally bioavailable.

While certain embodiments have been illustrated and described in the foregoing examples, it will be understood that changes and modifications can be made in the foregoing processes to make and use the compounds of the invention in accordance with ordinary skill in the art without departing from the present technology in its broader aspects as defined in the following claims.

The invention claimed is:

1. A compound of Formula I:

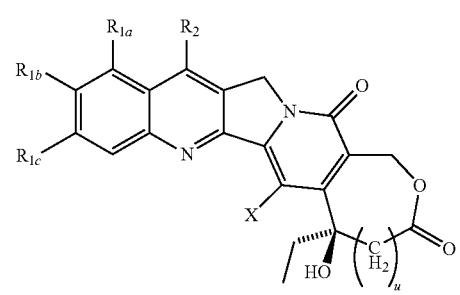

Formula I wherein u is 0 or 1;

$R_{1a}$, $R_{1b}$, and $R_{1c}$ independently are H, halogen, hydroxyl, nitrile, amino, substituted amino, nitro, carboxyl ester, aminocarbonyl, substituted sulfonyl, aminosulfonyl, substituted or unsubstituted $C_1$-$C_6$ alkyl, substituted or unsubstituted $C_2$-$C_6$ alkynyl, substituted or unsubstituted $C_2$-$C_6$ alkenyl, substituted or unsubstituted aryl, substituted or unsubstituted heteroaryl, substituted or unsubstituted heterocycloalkyl, or substituted or unsubstituted $C_1$-$C_6$ alkoxy group, or $R_{1a}$ and $R_{1b}$ together with the carbon atoms to which they are bonded form a 5-7 membered heterocycle, or $R_{1b}$ and $R_{1c}$ together with the carbon atoms to which they are bonded form a 5-7 membered heterocycle;

$R_2$ is H, halogen, nitrile, formyl, oxime, hydrazone, imine, substituted or unsubstituted $C_1$-$C_6$ alkyl, substituted or unsubstituted aryl, substituted or unsubstituted heteroaryl, substituted or unsubstituted heterocyclyl, substituted or unsubstituted $C_2$-$C_6$ alkenyl, or substituted or unsubstituted $C_2$-$C_6$ alkynyl group; or $R_2$ and $R_{1a}$ together with the carbon atoms to which they are attached form a 5-7 membered substituted cycloalkyl ring;

X is nitro or —$NR_3R_4$;

each $R_3$ and $R_4$ are independently H, substituted or unsubstituted $C_1$-$C_6$ alkyl, —$CO_2R_5$, or —$COR_6$;

$R_5$ is substituted or unsubstituted $C_1$-$C_6$ alkyl, substituted or unsubstituted aryl, or substituted or unsubstituted heteroaryl;

$R_6$ is H, substituted or unsubstituted $C_1$-$C_6$ alkyl, substituted or unsubstituted aryl, or substituted or unsubstituted heteroaryl;

or a carboxyl ester or a pharmaceutically acceptable salt thereof, provided however that the compound is not 14-nitro-20-acetoxycamptothecin.

2. The compound of claim 1, wherein $R_{1a}$, $R_{1b}$, and $R_{1c}$ independently are H, OH, methyl, fluoro, dimethylaminomethyl, —$NH_2$, —$NO_2$,

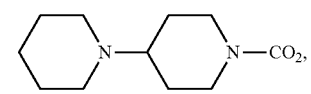

or $R_2$ and $R_{1a}$ together are

or $R_{1b}$ and $R_{1c}$ together are

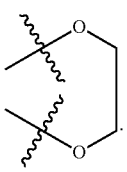

3. The compound of claim 1 or 2, wherein $R_{1a}$, $R_{1b}$, and $R_{1c}$ are H.

4. The compound of claim 1, wherein X is —$NO_2$, —$NH_2$, or —NHCHO.

5. The compound of claim 1, wherein u is 0.

6. The compound of claim 1 that is a compound of Formula III:

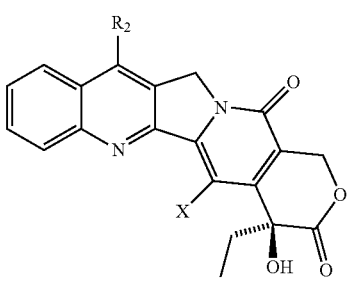

Formula III wherein $R_2$ is halo, cyano, substituted or unsubstituted $C_1$-$C_6$ alkyl, substituted or unsubstituted heteroaryl, substituted or unsubstituted heterocyclyl group, or —CH=$Y_1$;

$Y_1$ is O, N—$R_{10}$, or $CR_{11}R_{12}$;

$R_{10}$ is —$OR_{13}$, —$NR_{14}R_{15}$, or substituted or unsubstituted aryl or heteroaryl group;

$R_{11}$ is H or substituted or unsubstituted $C_1$-$C_3$ alkyl;

$R_{12}$ is H, —$COR_{16}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{13}$ is H, substituted or unsubstituted $C_1$-$C_6$ alkyl, substituted or unsubstituted $C_1$-$C_6$ alkenyl, substituted or unsubstituted $C_3$-$C_8$ cycloalkyl, substituted or unsubstituted heterocyclyl, substituted or unsubstituted aryl, or substituted or unsubstituted heteroaryl group;

$R_{14}$ and $R_{15}$ independently are H, —$SO_2R_{17}$, —$COR_{18}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group, or $R_{14}$ and $R_{15}$ together with the nitrogen atom to which they are bonded form a 5-7 membered heterocycle;

$R_{16}$ is —OH, —$OR_{19}$, —$NR_{26}R_{27}$, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{17}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{18}$ is H or substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{19}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group; and $R_{26}$ and $R_{27}$ independently are H, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group, or $R_{26}$ and $R_{27}$ together with the carbon atom to which they are bonded form a 5-7 membered heterocycle.

7. The compound of claim 1, wherein $R_2$ is unsubstituted $C_1$-$C_6$ alkyl.

8. The compound of claim 1 that is a compound of Formula IVA:

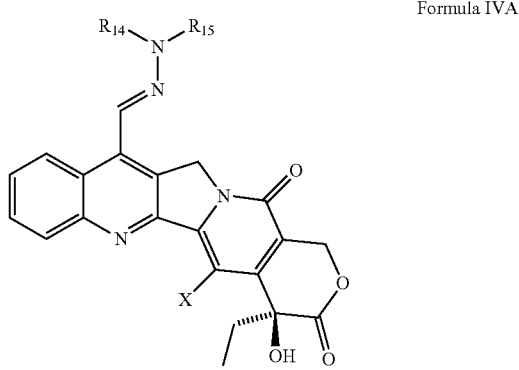

Formula IVA wherein $R_{14}$ is H, $SO_2R_{17}$, or $COR_{18}$;

$R_{17}$ is a substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{18}$ is H or a substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group;

$R_{15}$ is -$L_2$-$Z_2$; or $R_{14}$ and $R_{15}$ together with the nitrogen atom to which they are bonded form a 5-7 membered heterocycle;

$L_2$ is substituted or unsubstituted $C_1$-$C_6$ alkylene;

$Z_2$ is H, —OH, —$NR_{22}R_{23}$, or a leaving group; and $R_{22}$ and $R_{23}$ independently are H, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group, or $R_{22}$ and $R_{23}$ together with the nitrogen atom to which they are bonded form a 5-7 membered heterocycle.

9. The compound of any one of claims 1-5, wherein $R_2$ is —$CH(OR_{20})_2$ or —CHO, wherein $R_{20}$ is substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl group, or the two $R_{20}$ groups together with the oxygen atoms to which they are bonded form a 5-6 membered heterocycle.

10. A compound prepared by the process comprising contacting a compound of Formula IX:

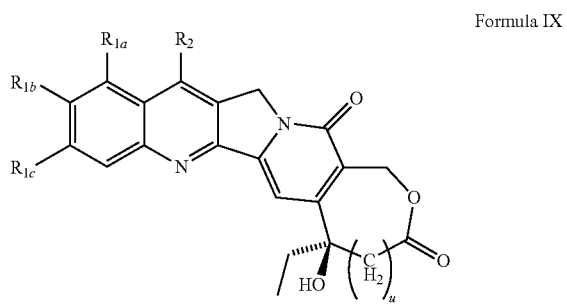

Formula IX wherein u is 0 or 1;

$R_{1a}$, $R_{1b}$, and $R_{1c}$ each independently are H, halogen, hydroxyl, amino, substituted amino, nitro, carboxyl ester, aminocarbonyl, substituted sulfonyl, aminosulfonyl, substituted or unsubstituted $C_1$-$C_6$ alkyl, substituted or unsubstituted $C_2$-$C_6$ alkynyl, substituted or unsubstituted $C_2$-$C_6$ alkenyl, substituted or unsubstituted aryl, substituted or unsubstituted heteroaryl, substituted or unsubstituted heterocyclyl, or substituted or unsubstituted $C_1$-$C_6$ alkoxy group, or $R_{1a}$ and $R_{1b}$ together with the carbon atoms to which they are bonded form a 5-7 membered heterocycle, or $R_{1b}$ and $R_{1c}$ together with the carbon atoms to which they are bonded form a 5-7 membered heterocycle; and $R_2$ is H, halogen, nitrile, formyl, oxime, hydrazone, imine, substituted or unsubstituted $C_1$-$C_6$ alkyl, substituted or unsubstituted aryl, substituted or unsubstituted heteroaryl, substituted or unsubstituted heterocyclyl, substituted or unsubstituted $C_2$-$C_6$ alkenyl, or substituted or unsubstituted $C_2$-$C_6$ alkynyl group; or $R_2$ and $R_{1a}$ together with the carbon atoms to which they are bonded form a 5-7 membered substituted cycloalkyl ring; or
a carboxyl ester or salt thereof
with fuming nitric acid, provided however that the compound prepared excludes 14-nitro-20-acetoxycamptothecin.
11. The compound of claim 1 selected from the group consisting of
TH1317
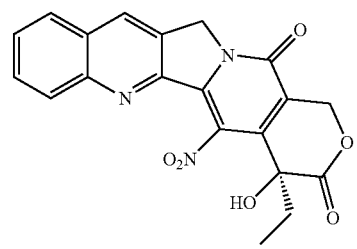
TH1320
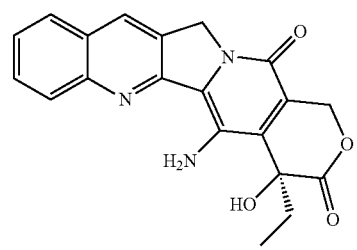 [SMILES: CC[C@@]1(O)C(=O)OCc2c1c([N+](=O)[O-])c1n(c2=O)Cc2cc3ccccc3nc2-1]
TH1446
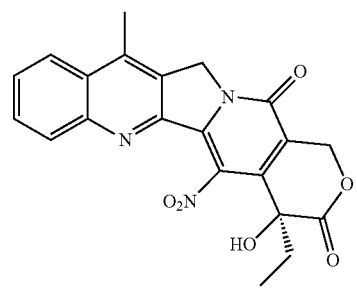 [SMILES: CC[C@@]1(O)C(=O)OCc2c1c(N)c1n(c2=O)Cc2c-1nc1ccccc1c2C]
TH1339
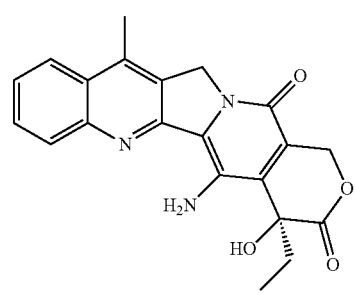
TH1332
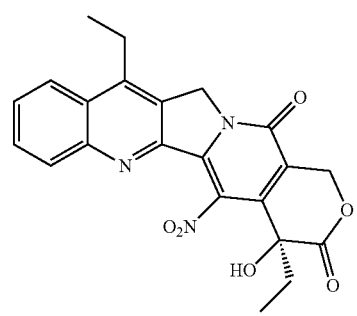 [SMILES: CCc1c2c(nc3ccccc13)-c1c([N+](=O)[O-])c3c(c(=O)n1C2)COC(=O)[C@]3(O)CC]
TH1338
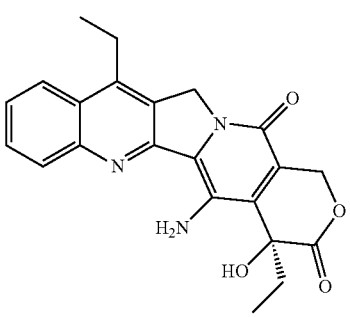
TH1386
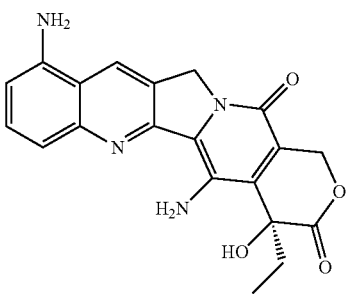 [SMILES: CC[C@@]1(O)C(=O)OCc2c1c([N+](=O)[O-])c1n(c2=O)Cc2cc3c([N+](=O)[O-])cccc3nc2-1]
TH1385
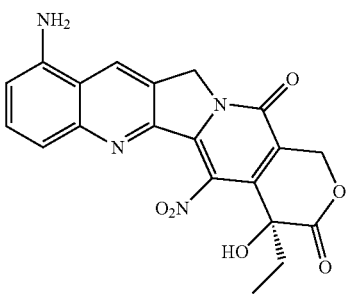
TH1408
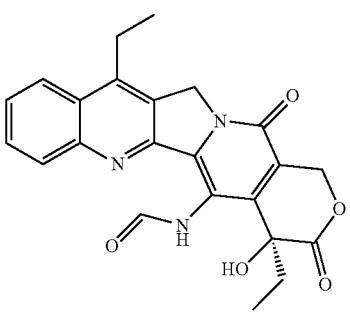 [SMILES: CCc1c2c(nc3ccccc13)-c1c(NC=O)c3c(c(=O)n1C2)COC(=O)[C@]3(O)CC]
TH1589

105
-continued
TH1431
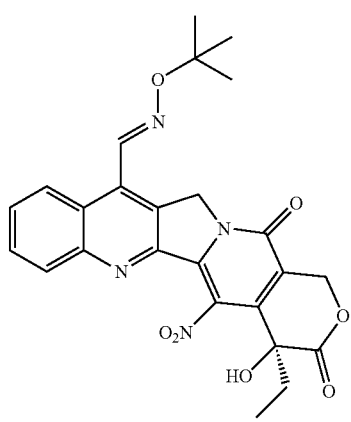 [SMILES: CC[C@@]1(O)C(=O)OCc2c1c([N+](=O)[O-])c1n(c2=O)Cc2c-1nc1ccccc1c2/C=N/OC(C)(C)C]
TH1499
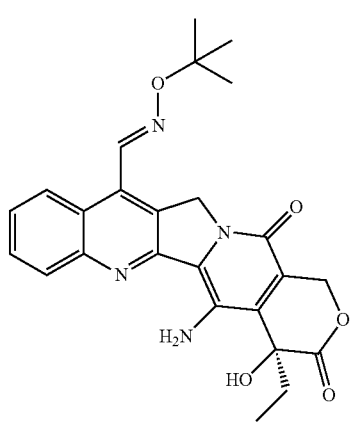 [SMILES: CC[C@@]1(O)C(=O)OCc2c1c(N)c1n(c2=O)Cc2c-1nc1ccccc1c2/C=N/OC(C)(C)C]
TH1522
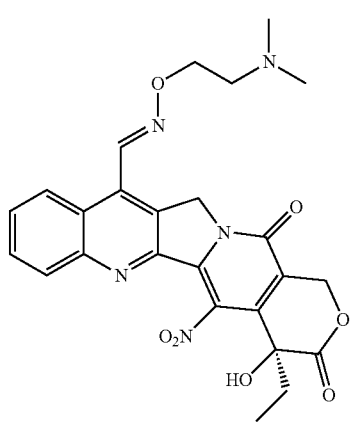 [SMILES: CC[C@@]1(O)C(=O)OCc2c1c([N+](=O)[O-])c1n(c2=O)Cc2c-1nc1ccccc1c2/C=N/OCCN(C)C]
106
-continued
TH1523
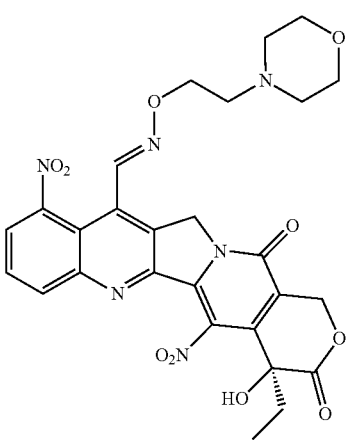 [SMILES: CC[C@@]1(O)C(=O)OCc2c1c([N+](=O)[O-])c1n(c2=O)Cc2c-1nc1cccc([N+](=O)[O-])c1c2/C=N/OCCN1CCOCC1]
TH1524
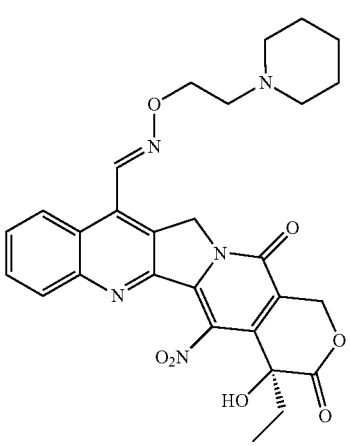 [SMILES: CC[C@@]1(O)C(=O)OCc2c1c([N+](=O)[O-])c1n(c2=O)Cc2c-1nc1ccccc1c2/C=N/OCCN1CCCCC1]
TH1525
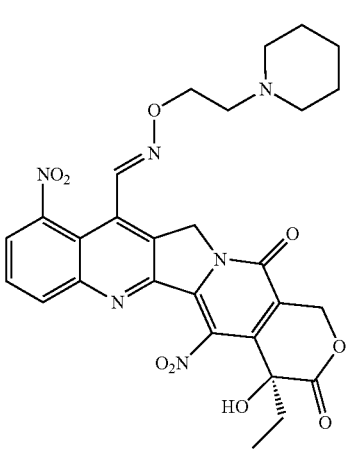
TH1598
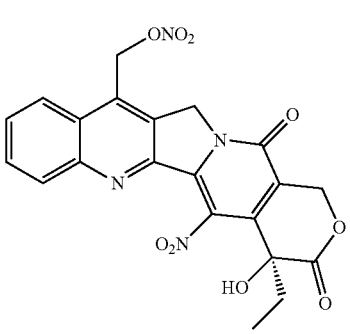

107
-continued
TH1599
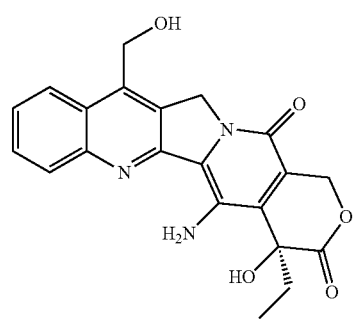
TH1333
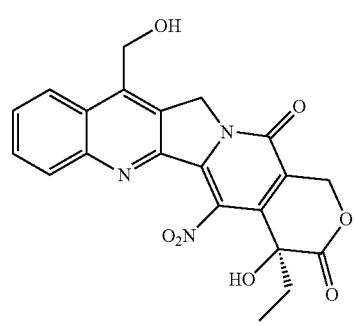 [SMILES: CC[C@@]1(O)C(=O)OCc2c1c(N)c1n(c2=O)Cc2c-1nc1ccccc1c2CO]
TH1626
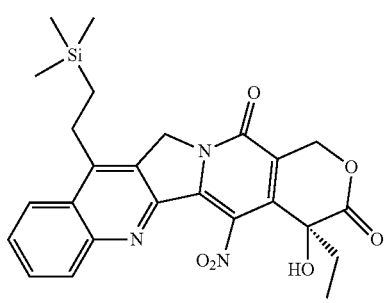
TH1627
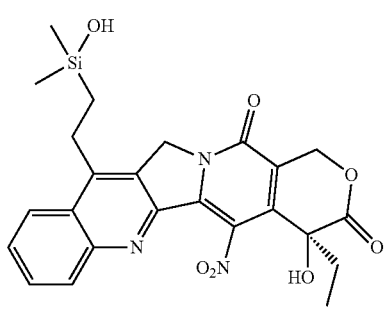
TH1628
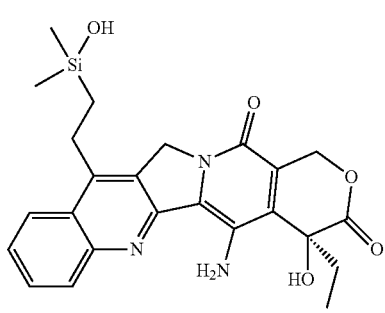 [SMILES: CC[C@@]1(O)C(=O)OCc2c1c(N)c1n(c2=O)Cc2c-1nc1ccccc1c2CC[Si](C)(C)O]
108
-continued
TH1631
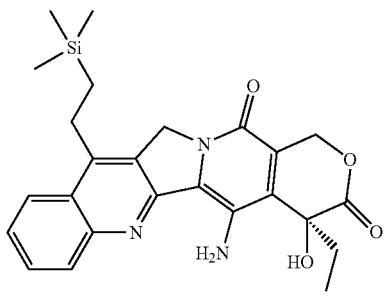 [SMILES: CC[C@@]1(O)C(=O)OCc2c1c(N)c1n(c2=O)Cc2c-1nc1ccccc1c2CC[Si](C)(C)C]
TH1636
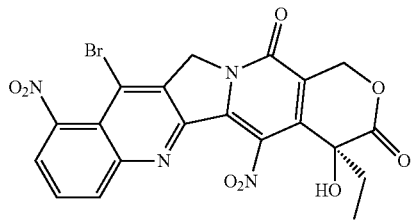 [SMILES: CC[C@@]1(O)C(=O)OCc2c1c([N+](=O)[O-])c1n(c2=O)Cc2c-1nc1cccc([N+](=O)[O-])c1c2Br]
TH1643
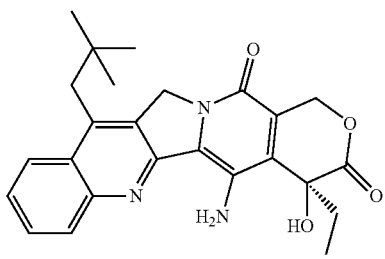 [SMILES: CC[C@@]1(O)C(=O)OCc2c1c(N)c1n(c2=O)Cc2c-1nc1ccccc1c2CC(C)(C)C]
TH1644
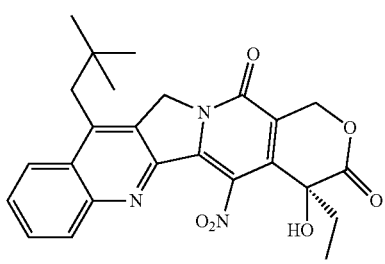
TH1650
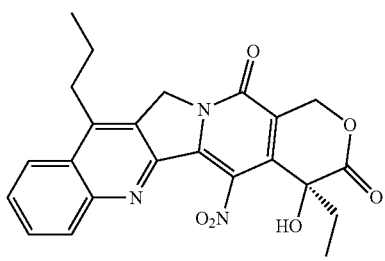 [SMILES: CCCc1c2c(nc3ccccc13)-c1c([N+](=O)[O-])c3c(c(=O)n1C2)COC(=O)[C@]3(O)CC]
TH1651
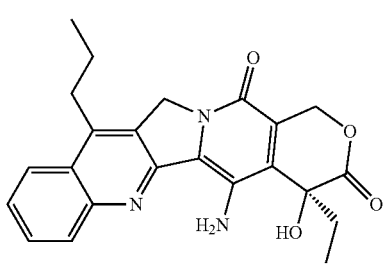

TH1762
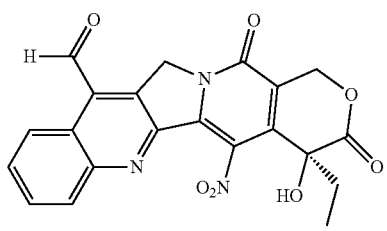 [SMILES: CC[C@@]1(O)C(=O)OCc2c1c([N+](=O)[O-])c1n(c2=O)Cc2c-1nc1ccccc1c2C=O]
TH1766
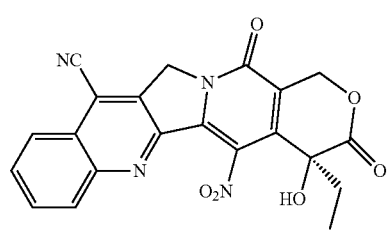 [SMILES: CC[C@@]1(O)C(=O)OCc2c1c([N+](=O)[O-])c1n(c2=O)Cc2c-1nc1ccccc1c2C#N]
TH1767
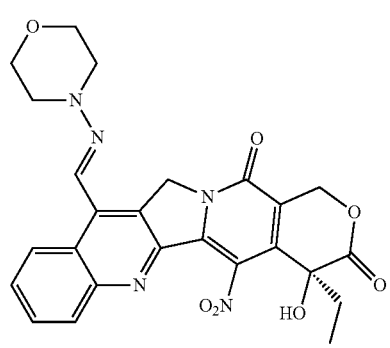 [SMILES: CC[C@@]1(O)C(=O)OCc2c1c([N+](=O)[O-])c1n(c2=O)Cc2c-1nc1ccccc1c2/C=N/N1CCOCC1]
TH1768
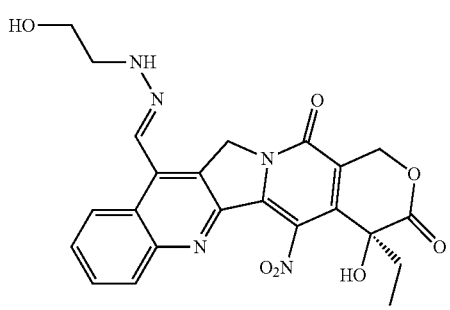 [SMILES: CC[C@@]1(O)C(=O)OCc2c1c([N+](=O)[O-])c1n(c2=O)Cc2c-1nc1ccccc1c2/C=N/NCCO]
TH1769
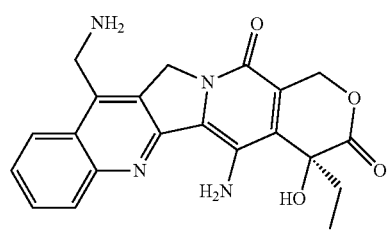 [SMILES: CC[C@@]1(O)C(=O)OCc2c1c(N)c1n(c2=O)Cc2c-1nc1ccccc1c2CN]
TH1770
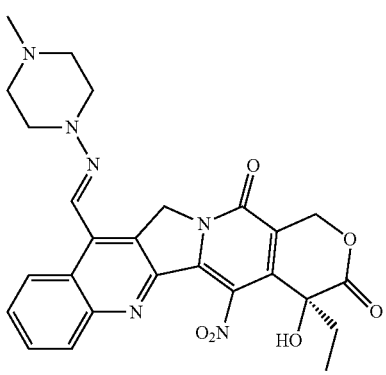 [SMILES: CC[C@@]1(O)C(=O)OCc2c1c([N+](=O)[O-])c1n(c2=O)Cc2c-1nc1ccccc1c2/C=C/N1CCN(C)CC1]
TH1771
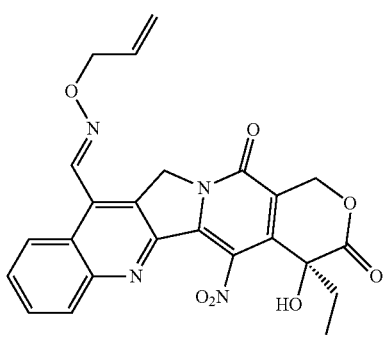 [SMILES: C=CCO/N=C/c1c2c(nc3ccccc13)-c1c([N+](=O)[O-])c3c(c(=O)n1C2)COC(=O)[C@]3(O)CC]
TH1775
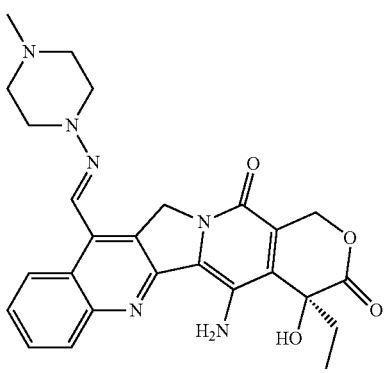 [SMILES: CC[C@@]1(O)C(=O)OCc2c1c(N)c1n(c2=O)Cc2c-1nc1ccccc1c2/C=N/N1CCN(C)CC1]
TH1776
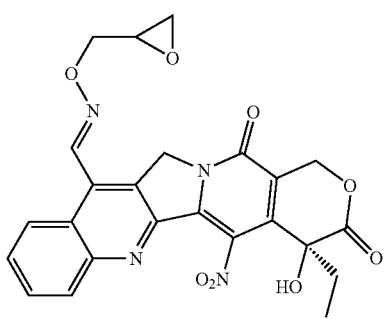 [SMILES: CC[C@@]1(O)C(=O)OCc2c1c([N+](=O)[O-])c1n(c2=O)Cc2c-1nc1ccccc1c2/C=N/OCC1CO1]

111
-continued
TH1777
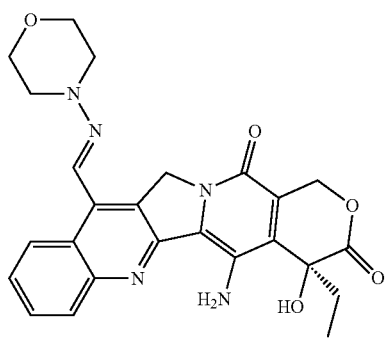 [SMILES: CC[C@@]1(O)C(=O)OCc2c1c(N)c1n(c2=O)Cc2c-1nc1ccccc1c2/C=N/N1CCOCC1]
TH1778
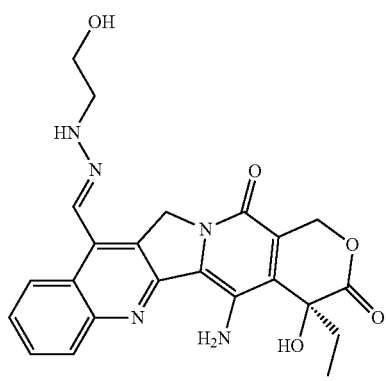 [SMILES: CC[C@@]1(O)C(=O)OCc2c1c(N)c1n(c2=O)Cc2c-1nc1ccccc1c2/C=N/NCCO]
TH1780
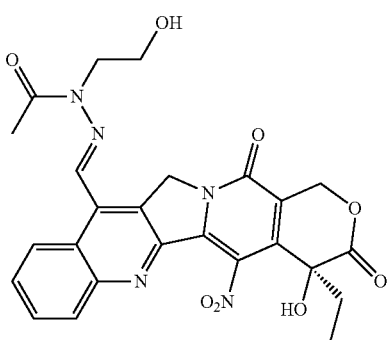 [SMILES: CC[C@@]1(O)C(=O)OCc2c1c([N+](=O)[O-])c1n(c2=O)Cc2c-1nc1ccccc1c2/C=N/N(CCO)C(C)=O]
TH1781
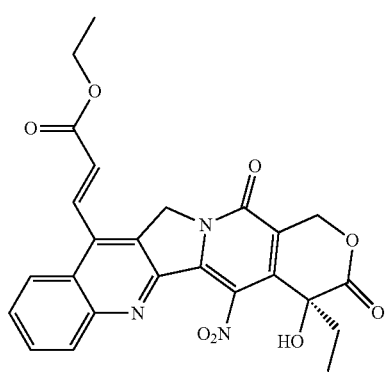 [SMILES: CCOC(=O)/C=C/c1c2c(nc3ccccc13)-c1c([N+](=O)[O-])c3c(c(=O)n1C2)COC(=O)[C@]3(O)CC]
112
-continued
TH1783
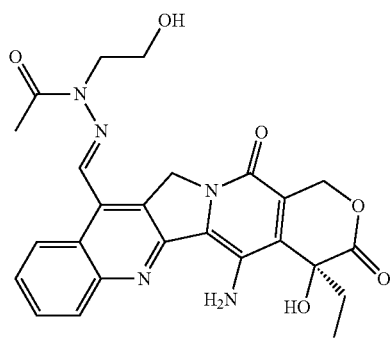
TH1784
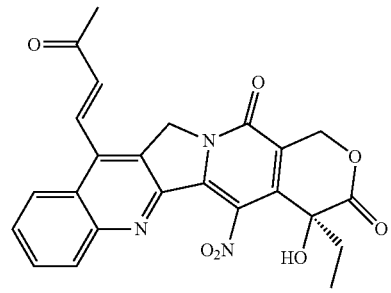 [SMILES: CC[C@@]1(O)C(=O)OCc2c1c([N+](=O)[O-])c1n(c2=O)Cc2c-1nc1ccccc1c2/C=C/C(C)=O]
TH1785
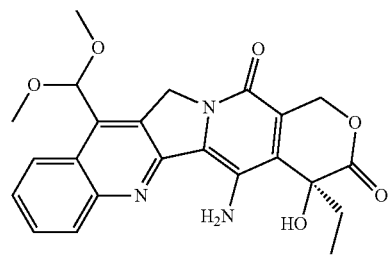 [SMILES: CC[C@@]1(O)C(=O)OCc2c1c(N)c1n(c2=O)Cc2c-1nc1ccccc1c2C(OC)OC]
TH1786
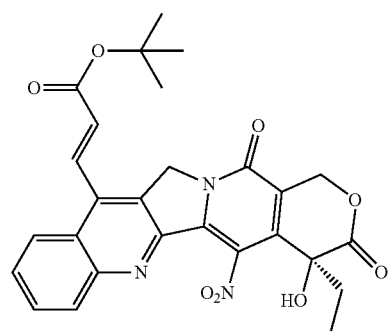 [SMILES: CC[C@@]1(O)C(=O)OCc2c1c([N+](=O)[O-])c1n(c2=O)Cc2c-1nc1ccccc1c2/C=C/C(=O)OC(C)(C)C]
TH1787
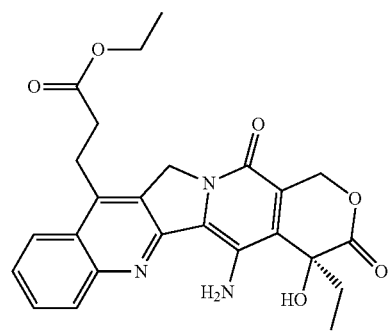 [SMILES: CCOC(=O)CCc1c2c(nc3ccccc13)-c1c(N)c3c(c(=O)n1C2)COC(=O)[C@]3(O)CC]

113
-continued
TH1789
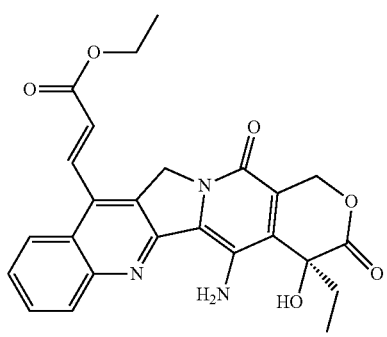 [SMILES: CCOC(=O)/C=C/c1c2c(nc3ccccc13)-c1c(N)c3c(c(=O)n1C2)COC(=O)[C@]3(O)CC]
TH1790
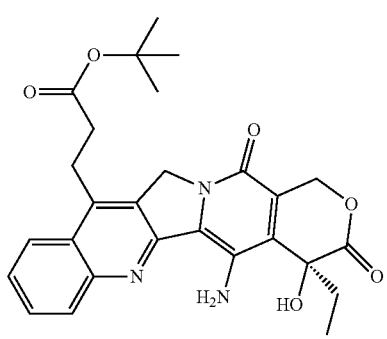 [SMILES: CC[C@@]1(O)C(=O)OCc2c1c(N)c1n(c2=O)Cc2c-1nc1ccccc1c2CCC(=O)OC(C)(C)C]
TH1791
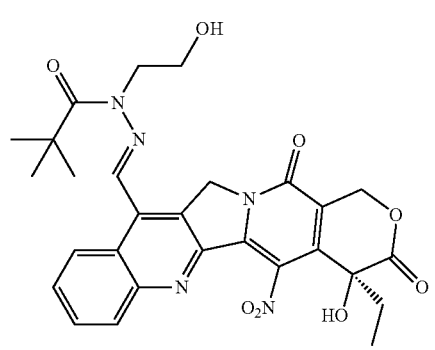 [SMILES: CC[C@@]1(O)C(=O)OCc2c1c([N+](=O)[O-])c1n(c2=O)Cc2c-1nc1ccccc1c2/C=N/N(CCO)C(=O)C(C)(C)C]
TH1793
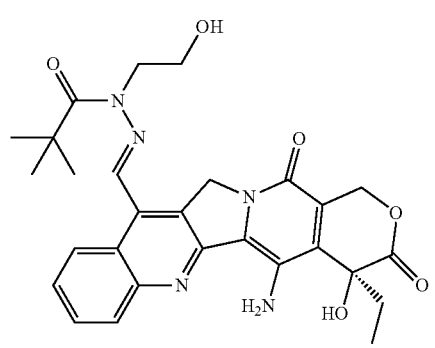 [SMILES: CC[C@@]1(O)C(=O)OCc2c1c(N)c1n(c2=O)Cc2c-1nc1ccccc1c2/C=N/N(CCO)C(=O)C(C)(C)C]
114
-continued
TH1794
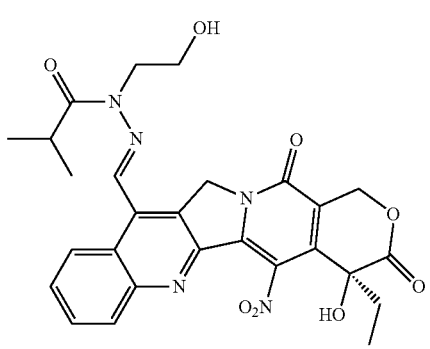
TH1796
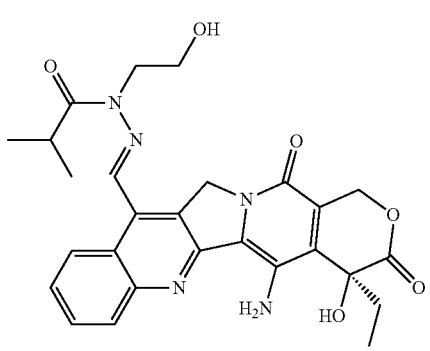 [SMILES: CC[C@@]1(O)C(=O)OCc2c1c(N)c1n(c2=O)Cc2c-1nc1ccccc1c2/C=N/N(CCO)C(=O)C(C)C]
TH1797
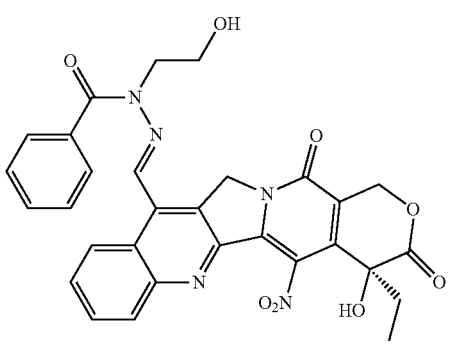 [SMILES: CC[C@@]1(O)C(=O)OCc2c1c([N+](=O)[O-])c1n(c2=O)Cc2c-1nc1ccccc1c2/C=N/N(CCO)C(=O)c1ccccc1]
TH1798
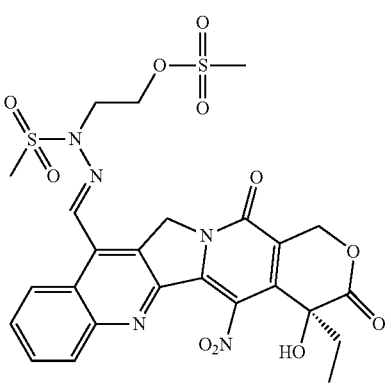 [SMILES: CC[C@@]1(O)C(=O)OCc2c1c([N+](=O)[O-])c1n(c2=O)Cc2c-1nc1ccccc1c2/C=N/N(CCOS(C)(=O)=O)S(C)(=O)=O]

115
-continued
TH1799
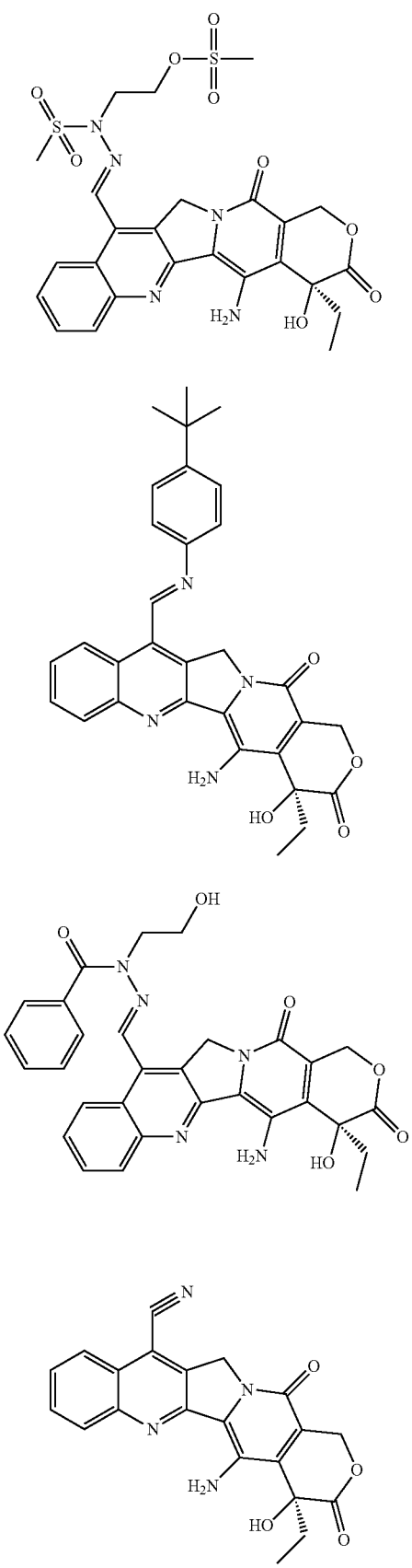
TH1809
TH1800
TH1801
116
-continued
TH1803
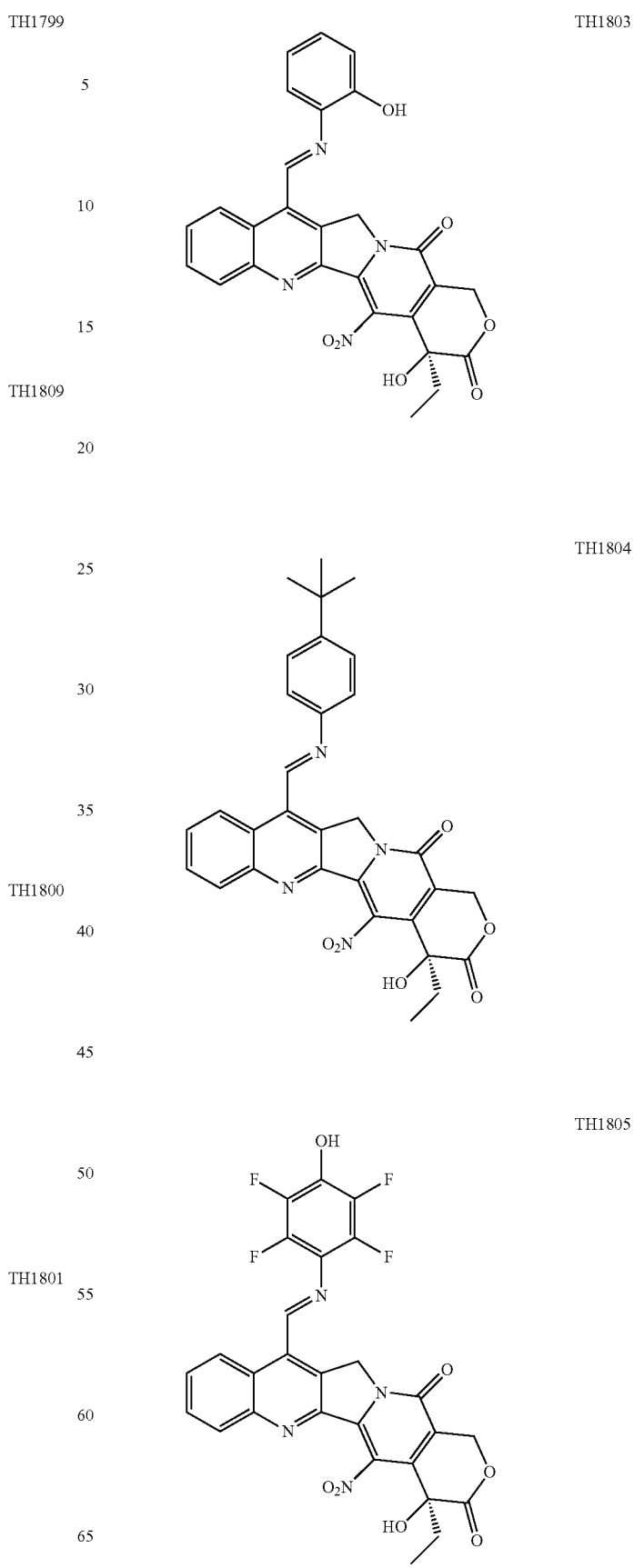
TH1804
TH1805

-continued
TH1812
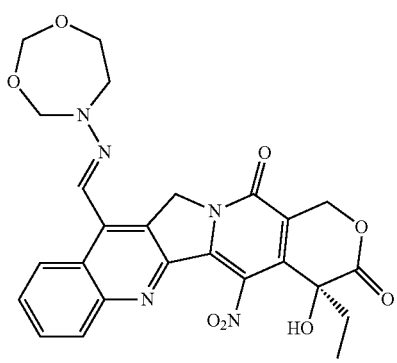 [SMILES: CC[C@@]1(O)C(=O)OCc2c1c([N+](=O)[O-])c1n(c2=O)Cc2c-1nc1ccccc1c2/C=N/N1CCOCOC1]
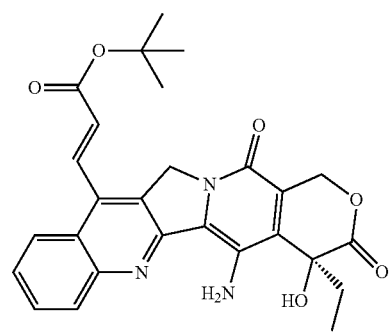
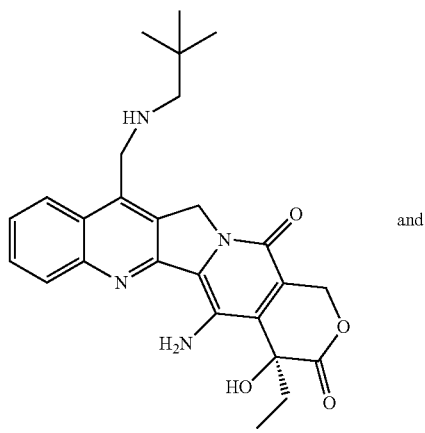
and
TH1816
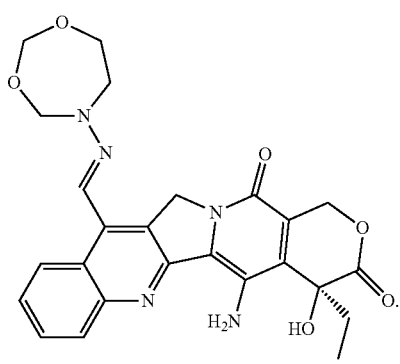
12. The compound of claim 11 selected from the group consisting of:
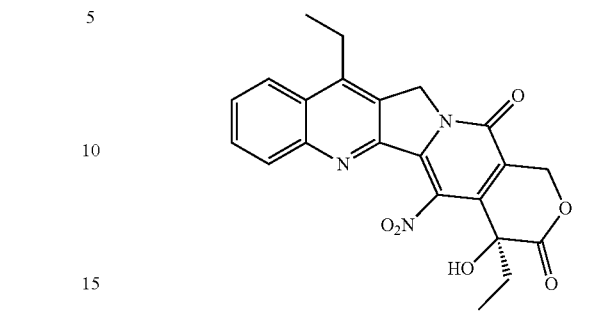
TH1811
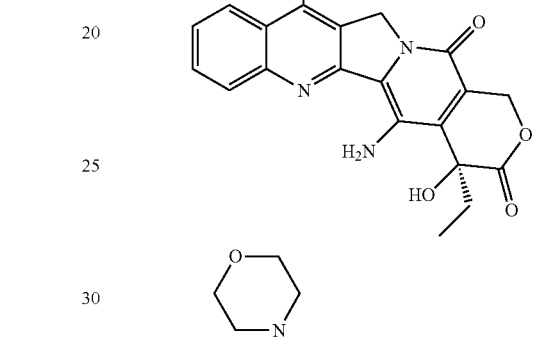
TH1814
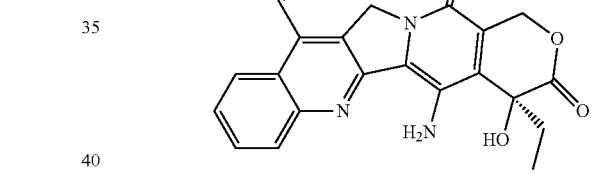
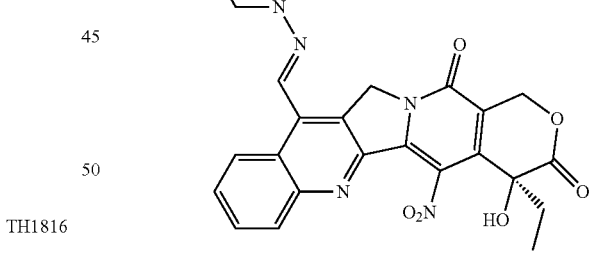
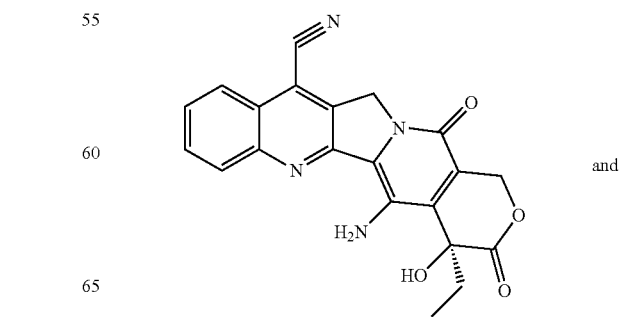
and

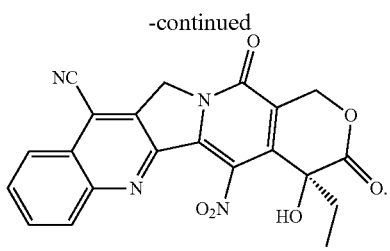

13. A method of synthesis comprising contacting a compound of Formula IX:

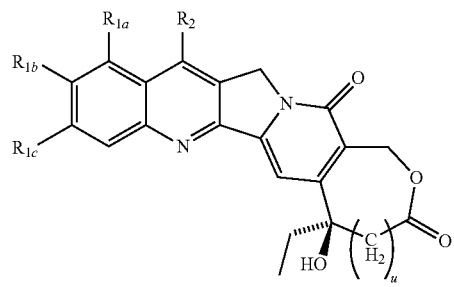

Formula IX wherein
u is 0 or 1;
$R_{1a}$, $R_{1b}$, and $R_{1c}$ independently are H, halogen, hydroxyl, amino, substituted amino, nitro, carboxyl ester, aminocarbonyl, substituted sulfonyl, aminosulfonyl, substituted or unsubstituted $C_1$-$C_6$ alkyl, substituted or unsubstituted $C_2$-$C_6$ alkynyl, substituted or unsubstituted $C_2$-$C_6$ alkenyl, substituted or unsubstituted aryl, substituted or unsubstituted heteroaryl, substituted or unsubstituted heterocyclyl, or substituted or unsubstituted $C_1$-$C_6$ alkoxy group, or $R_{1a}$ and $R_{1b}$ together with the carbon atoms to which they are bonded form a 5-7 membered heterocycle, or $R_{1b}$ and $R_{1c}$ together with the carbon atoms to which they are bonded form a 5-7 membered heterocycle; and
$R_2$ is H, halogen, nitrile, formyl, oxime, hydrazone, imine, substituted or unsubstituted $C_1$-$C_6$ alkyl, substituted or unsubstituted aryl, substituted or unsubstituted heteroaryl, substituted or unsubstituted heterocyclyl, substituted or unsubstituted $C_2$-$C_6$ alkenyl, or substituted or unsubstituted $C_2$-$C_6$ alkynyl group; or $R_2$ and $R_{1a}$ together with the carbon atoms to which they are bonded form a 5-7 membered substituted cycloalkyl ring; or
a carboxyl ester or a salt thereof
with fuming nitric acid to provide a compound of Formula IXA:

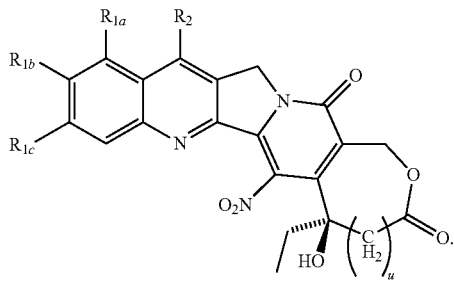

Formula IXA

14. The method of claim 13, wherein the contacting is performed in acetic anhydride.

15. A pharmaceutical composition comprising the compound of claim 1 or 14-nitro-20-acetoxycamptothecin and a pharmaceutically acceptable carrier, excipient, or diluent.

16. A method of inhibiting growth of a hyperproliferative cell comprising contacting the hyperproliferative cell with an effective amount of the compound of claim 1 or 14-nitro-20-acetoxycamptothecin, wherein the hyperproliferative cell is a cancer cell selected from lung cancer, melanoma, prostate cancer, colon cancer, and ovarian cancer.

17. A method of treating a cancer selected from lung cancer, melanoma, prostate cancer, colon cancer, and ovarian cancer comprising administering a therapeutically effective amount of the compound of claim 1 or 14-nitro-20-acetoxycamptothecin to a patient in need of such treatment thereby treating the cancer.

* * * * *